US008193160B2

(12) United States Patent
Naqvi et al.

(10) Patent No.: US 8,193,160 B2
(45) Date of Patent: Jun. 5, 2012

(54) **SYSTEM FOR INHIBITING PATHOGENICITY IN THE RICE-BLAST FUNGUS *MAGNAPORTHE GRISEA***

(75) Inventors: Naweed Isaak Naqvi, Singapore (SG); Chuan Bao Sun, Singapore (SG)

(73) Assignee: Temasek Life Sciences Laboratory, Singapore (SG)

( * ) Notice: Subject to any disclaimer, the term of this patent is extended or adjusted under 35 U.S.C. 154(b) by 698 days.

(21) Appl. No.: 12/293,240

(22) PCT Filed: Mar. 14, 2007

(86) PCT No.: PCT/SG2007/000071
§ 371 (c)(1),
(2), (4) Date: Sep. 16, 2008

(87) PCT Pub. No.: WO2007/106048
PCT Pub. Date: Sep. 20, 2007

(65) Prior Publication Data
US 2009/0099088 A1  Apr. 16, 2009

Related U.S. Application Data

(60) Provisional application No. 60/782,515, filed on Mar. 16, 2006.

(51) Int. Cl.
*A61K 48/00* (2006.01)
*C07H 21/02* (2006.01)
(52) U.S. Cl. ..................... 514/44 R; 536/23.1
(58) Field of Classification Search ............... 514/44 R; 536/23.1
See application file for complete search history.

(56) References Cited

OTHER PUBLICATIONS

Connors, T.D., Vann Raay, T.J., Petry, L.R., Klinger, K.W., Landes, G.M., Burn, T.C. (1997) The Cloning of a human abc gene(ABC3) mapping to chromosome 16p13.3. Genomics. 39: 231-234.*
Dean et al. Apr. 21, 2005; The genome sequence of the rice blast fungus Magnaporthe grisea. Nature 434:980-986.*
Tobin et al. 1997; Genes encoding multiple drug resistance-like proteins in *Aspergillus fumigatus* and *Aspergillus flavus*. Gene. 200:11-23.*
Database GenBank, Accession No. DQ156556, Aug. 28, 2005 abstract.
Sun, C.B., "A Multidrug Resistance Transporter in Magnaporthe is Required for Host Penetration and for Survival during Oxidative Stress", The Plant Cell, 18(12): 3686-3705 (Dec. 2006).
Lee, et al., "A novel ABC transporter gene ABC2 involved in multidrug susceptibility but not pathogenicity in rice blast fungus, Magnaporthe grisea" Pest. Biochem. and Phys. 81:13-23, 2005.
Thines, et al., "Fungal secondary metabolites as inhibitors of infection-related morphogenesis in phytopathogenic fungi" Mycol. Res. 108(1):14-25, 2004.
Urban, et al., "An ATP-driven efflux pump is a novel pathogenicity factor in rice blast disease" EMBO J. 18 (3):512-521, 1999.

* cited by examiner

*Primary Examiner* — Karen Carlson
(74) *Attorney, Agent, or Firm* — Rothwell, Figg, Ernst & Manbeck, P.C.

(57) ABSTRACT

In *Magnaporthe* species and other plant pathogenic fungal species, the appressoriu, (infection structure) is responsible for breaching the host plant cell wall and gaining entry into the host tissues. *Magnaporthe* ABC3 protein is an MDR transporter that plays an important role during host penetration and also is involved in regulating fungal response to intracellular oxidative stress. The insertional mutant abc3Δ, in which the ABC3 efflux pump function is blocked, lacks functional appressoria and is therefore incapable of causing disease in host plants. This invention provides the abc3 nucleic acid (gene) and ABC3 protein from *Magnaporthe* or from *Aspergillus, Ustilago* or *Fusarium* and describes methods for reducing plant pathogenicity for important rice pathogens.

8 Claims, 52 Drawing Sheets

```
MgABC3     1 ----------------------------------------------MTAATP
ScSTE6     1 ------------------------------------------------------
SpPMD1     1 MSLHSKKSTSTVKDNEHSLDLSIKSIPSNEKNFSTEKSENEASESHVVDVVKDPFEQYTP
ScPDR5     1 MPEAKLNNNVNDVTSYSSASSSTENAADLHNYNGFDEHTEARIQKLARTLPAQSMQNSTQ
CaCDR1     1 MSDSKMSSQDESKLEKAISQDSSSENHSINEYHGFDAHTSENIQNLARTFTHDSFKDDSS
MgABC1     1 MSQPVEDPSHDQARNDNAQTTTDTGNASMPKTNGHDQESSATGISSSPADTLMDKEKQAA

MgABC3     7 ADGEK-------------------------------------------------------
ScSTE6     1 ------------------------------------------------------------
SpPMD1    61 EEQEI-------------------------------------------------------
ScPDR5    61 SAPNKSDAQSIFSSGVEGVNPIFSDPEAPGYDPK---------------------------
CaCDR1    61 AGLLKYLTHMSEVPGVN------PYEHEEINNDQ---------------------------
MgABC1    61 PTPEPSTEKAAVPDPAASVASDTAEDEFFDDNDSEQRRRNEMVQQLARTYTSRSNASAAA

MgABC3    12 ------------------------------GFKLNPKHLLAIHNFKRILTYGTKWDKIV
ScSTE6     1 ------------------------------MNFLSFKTTKHYHIFRYVNIRNDYRLLMI
SpPMD1    66 ------------------------------LYKQINDTPAKLSGYPRILSYADKWDIML
ScPDR5    95 --------------------LDPNSENFSSAAWVKNMAHLSAADPDFYKPYSLGCAWKNLS
CaCDR1    89 --------------------LNPDSENFNAKFWVKNLRKLFESDPEYYKPSKLGIGYRNLR
MgABC1   121 DEYGNANPFLIASEDPDSPLNPSGNNFKAYAWAKAIAGMVAAEGGSFR--TIGICFQNMN

MgABC3    41 LGVSTVSSVATGLTIPLMVVVFARLIGIFTDFYRQGSTVTGAQFSSQVNQCVYNIIYLFV
ScSTE6    30 MIIGTVATGLVPAITSILTGRVFDLLSVFVANG------SHQGLYSQLVQRSMAVMALGA
SpPMD1    95 QLAGTITGIGAGLGMPLMSLVSGQLAQAFTDLASGKGASS---FQHTVDHFCLYFIYIAI
ScPDR5   136 ASGASADVAYQSTVVNIPYKILKSGLRKFQRSKETNTFQILKPMDGCLNPGELLVVLGRP
CaCDR1   130 AYGVANDSDYQPTVTNALWKLATEGFRHFQKDDDSRYFDILKSMDAIMRPGELTVVLGRP
MgABC1   179 VFGFGAATDFQKTVS-NVWLEAANMLRTAVGMGKTTRIDILRGFNGVVRNGEMLVVLGPP

MgABC3   101 ARIIFSYISNLGFRMFSLRISS--TIRTVYLRSLFALPISVIDAIPAGQTAAIVTGTASL
ScSTE6    84 ASVPVMWLSLTSWMHIGERQGFRIRSQILEAYLEEKPMEWYDNNEKLLGDFTQINRCVEE
SpPMD1   152 GVFGCSYIYTVTFIIAGERIAR--RIRQDYLHAILSQNIGYFDRLGAGEITPRITTDTNF
ScPDR5   196 GSGCTTLLKSISSNTHGFDLGADTKISYSGYSGDDIKKHFRGEVVYNAEADVHLPHLTVF
CaCDR1   190 GAGCSTLLKTIAVNTYGFHIGKESQITYDGLSPHDIERHYRGDVIYSAETDVHFPHLSVG
MgABC1   238 GSGCSTFLKTIAGETNGLNVDQSAYFNYQGLSAEEMHKRHRGEAIYTAEVDVHFPQLSVG
```

FROM FIG. 3A-1

```
MgABC3   159  LQVGISEKLGGGIASLASVASSVVVALVFNWLLTFVTIAGLAFIAIVYVIFTPLVGKKAL
ScSTE6   144  LRSSSAEASAITFQNLVAICALLGTSFYYSWSLTLIILCSSPIITFFAVVFSRMIHVYSE
SpPMD1   210  IQDGLGEKVGLVFFAIATFVSGFVIAFIRHWKFTLILSSMFPAICGGIGLGVPFITKNTK
ScPDR5   256  ETLVTVARLKTPQNRIKGVDRESYANHLAEVAMATYGLSHTRNTKVGNDIVRGVSGGERK
CaCDR1   250  DTLEFAARLRTPQNRGEGIDRETYAKHMASVYMATYGLSHTRNTNVGNDFVRGVSGGERK
MgABC1   298  DTLTFAANARAPRRAPPGVSKTLFANHIRDVVMAIFGISHTINTRVGNEYIRGVSGGERK

MgABC3   219  EVHEADVKASSIATEAFTSVRMLAACGAENKVARRYAVHVDESYQKGLRMAWLVGVQQMF
ScSTE6   204  KENSETSKAAQLLTWSMNAAQLVRLYCTQRLERKKFKEIILNCNTFFIKSCFFVAANAGI
SpPMD1   270  GQIAVVAESSTFVEEVFSNIRNAFAFGTQDILAKLYNKYLITAQRFGINKAIAMGLMVGW
ScPDR5   316  RVSIAEVSICGSKFQCWDNATRGLDSATALEFIRALKTQADISNTSATVAIYQCSQDAYD
CaCDR1   310  RVSIAEASLSGANIQCWDNATRGLDSATALEFIRALKTSAVILDTTPLIAIYQCSQDAYD
MgABC1   358  RVTIAEAALSGAPLQCWDNSTRGLDSANAIEFCKTLRVCTRLFQTTACVSIYQAPQSAYD

MgABC3   279  VFFGVYATFALAFYFAFRMYNTSITTTPEDLIVVLLCVMMMATSIGQITAPLAAAQQAAE
ScSTE6   264  LRFLTLTMFVQGFWFGSAMIKKGKLNINDVITCFHSCIMLGSTLNNTLHQIVVLQKGGVA
SpPMD1   330  MFFVAYGVYGLAFWEGGRLLHAGDLDVSKLIGCFFAVLIASYSLANISPKMQSFVSCASA
ScPDR5   376  LFNKVCVLDDGYQIYYGPADKAKKYFEDMGYVCPSRQTTADFLTSVTSPSERTLNKDMLK
CaCDR1   370  LFDKVVVLYEGYQIFFGKATKAKEYPEKMGWKCPQRQTTADFLTSLTNPAEREPLPGYED
MgABC1   418  MFDKAVVLYEGYQIYFGPADEAKQYFVNLGFECPAR-TTPDFLTSMTAPHERIVRPGFEG

MgABC3   339  ACGIFHTIIDFPKPVYG---SARGEHEVRADGDIVLMNVNFAYPTRPEVKVLDNLSLVFP
ScSTE6   324  MEKIMTLLKDGSKRNPLNKTVAHQFPLDYATSDLTFANVSFSYPSRPSEAVLKNVSLNFS
SpPMD1   390  AKKIFDTIDRVSPINAF---TPTGDVVKDIKGEIELKNIRFVYPTRPEVLVLDNFSLVCP
ScPDR5   436  KGIHIPQTPKEMNDYWV---KSPNYKELMKEVDQRLLNDDE--ASREAIKEAHIAKQSKR
CaCDR1   430  K---VPRTAQEFETYWK---NSPEYAELTKEIDEYFVECERS-NTRETYRESHVAKQSNN
MgABC1   477  K---APRTPEEFAIAWE---NSAEYTALQADIEEYKSSHPINGPDAEAFRKSRAAQQGRG
```

FIG. 3A-2

```
MgABC3   396  AGKVTAIVGPSGSGKSTIVGILERWYEFNGDPVLNPLVLYLRNGFVSVGGRLLTEIDVKW
ScSTE6   384  AGQPTFIVGKSGSGKSTLSNLLLRFYDGYN------------GSISINGHNIQTIDQKL
SpPMD1   447  SGKITALVGASGSGKSTIIGLVERFYDPIG------------GQVFLDGKDLRTLNVAS
ScPDR5   491  ARPSSPYTVS--YMMQVKYLLIREMWRLRNNIGFTLPMILGNCSMALILGSMPFKIMKKG
CaCDR1   483  TRPASPYTVS--FFMQVRYGVARNFLRMKGDPSIPIFSVFGQLVMGLILSSVFYNLS--Q
MgABC1   531  QRPNSPYTLS--FYQQTKLCLWRGWKRLLGDPTLTVGALFANTLMALVISSIFFNLQ--M

MgABC3   456  WRNQIGLVQQDNVLFNTTIYKNVEHGLIGTLWEHESDE-KKAMLIETACRDAFADEFINR
ScSTE6   431  LIENITVVEQRCTLFNDTLRKNILLGSTDSVRNADCSTNENRHLIKDACQMALLDRFILD
SpPMD1   494  LRNQISLVQQEPVLFATTVFENITYGLPDTIKGTLSKE-ELERRVYDAAKLANAYDPIMT
ScPDR5   549  DTSTFYFRGSAMFFAILFNAFSSLLEIFSLYEARPITE-KHRTYSLYFPSADAFASVLSE
CaCDR1   539  TTGSFYYRGAAMFFAVLFNAFSSLLEIMSLFEARPIVE-KHKKYALYRPSADALASIISE
MgABC1   587  TTSSFFQRGALLFFACLLNGFAAALEILILFAQRPIVE-KHDRYALYHPSAEAVASMLCD

MgABC3   515  LPDRYQTTVGE-------SGIKLSGGQRQRLAIARAIVKQPKILILDEATSAIDVRSEQI
ScSTE6   491  LPDGLETLIGTG------GVTLSGGQQQRVAIARAFIRDTPILFLDEAVSALDIVHRNL
SpPMD1   553  LPEQFSTNVGQ-------RGFLMSGGQKQRIAIARAVISDPKILLLDEATSALDSKSEVL
ScPDR5   608  IPSKLIIAVCFNIIFYFLVDFRRNGGVFFFYLLINIVAVFSMSHLFRCVGSLTKTLSEAM
CaCDR1   598  LPVKLAMSMSFNFVFYFMVNFRRNPGRFFFYWLMCIWCTFVMSHLFRSIGAVSTSISGAM
MgABC1   646  MPYKVFNAIVFNLVLYFMANLRREPGAFFFYLLISFATVLAMSMMFRTIASMSRSLSQAM

MgABC3   568  VQAALERASRGRTTVVIAHRLGTVKKADKIIVLSKGQVVQEGTHDELRRQRGSAYYMLAN
ScSTE6   544  LMKAIRHWRKGKTTIILTHELSQIESDDYLYLMKEGEVVESGTQSELLADPTTTFSTWYH
SpPMD1   606  VQKALDNASRSRTTIVIAHRLSTIRNADNIVVVNAGKIVEQGSHNELLDLNG-AYARLVE
ScPDR5   668  VPASMLLLALSMYTGFAIPKKKILRWSKWIWYINPLAYLFESLLINEFHGIKFPCAEYVP
CaCDR1   658  TPATVLLLAMVIYTGFVIPTPSMLGWSRWINYINPVGYVFESLMVNEFHGREFQCAQYVP
MgABC1   706  VPAAAIILILIIFTGFVIPLDYMLPWCRWLNYIDILAYSFESLLINEFAGQRYTCTEFVP

MgABC3   628  AQSLNVRRRSSRMSIDQTPDEEDDSGYFRTTSMHDGD----SDHTAHSSNYGSDEEDDFI
ScSTE6   604  --LQNDYSDAKTIVDTETEEKSIHTVESFNSQLETPKLGSCLSNLGYDETDQLSFYEAIY
SpPMD1   665  AQKLSGGEKDQEMVEEELEDAPREIPITSFGDDDEDNDMASLEAPMMSHNTDTDTLNNKL
ScPDR5   728  --RGPAYANISSTESVCTVVGAVPGQDYVLGDDFIRGTYQYYHKDKWRGFGIGMAYVVFF
CaCDR1   718  --SGPGYENISRSNQVCTAVGSVPGNEMVSGTNYLAGAYQYYNSHKWRNLGITIGFAVFF
MgABC1   766  RAEFPGYGDLSGTNRVCQAVGSVAGQPFVKGEDYLYSSFRYESANKWRNFGILIAFMIFF
```

FROM FIG. 3B-1 

```
MgABC3  684  MERPRVRARDDVGVEMSTSTIHTAH--------------------------------TPVS
ScSTE6  662  QKRSNVRTRRVKVEE-----------------------------------------------
SpPMD1  725  NEKDNVVFEDKTLQHVASEIVPNLP-------------------------------PADV
ScPDR5  786  FFVYLFLCEYNEGAKQKGEILVFPRSIVKRMKKRGVLTEKNANDPENVGERSDLSSDRKM
CaCDR1  776  LAIYIALTEFNKGAMQKGEIVLFLKGSLKKHKRKTAASNKGDIEAGPVAGKLDYQDEAEA
MgABC1  826  CSRTWLRPRMCERKKSKGEVLVFRRGQRPAAIKDAKTDPEAG--------------PPKV

MgABC3  713  DGPPDDAAKIQVVEIQDHWLG-----GFAELLAEQGSRWKLYFVIIIGAIGAGASTPVQA
ScSTE6  677  -ENIGYALKQQKNTESSTGPQLLSIIQIIKRMIKSIRYKKILILGLLCSLIAGATNPVFS
SpPMD1  754  GELNEEPKKSKKSKKNNHEINSLTALWFIHSFVRTMIEIICLLIGILASMICGAAYPVQA
ScPDR5  846  LQESSEEESDTYGEIGLSKSEAIFHWRNLCYEVQIKAETRRILNNVDGWVKPGTLTALMG
CaCDR1  836  VNNEKFTEKGSTGSVDFPENREIFFWRDLTYQVKIKKEDRVILDHVDGWVKPGQITALMG
MgABC1  872  GGAVVAANMTGENAGFIQRQTSTFGWRDVCYEVQIKKETRRILDHVDGWVKPGTLTALMG

MgABC3  768  YLFATLLN--LFS-FRGPQVNQLANFFCLMFVVLAAGVGISHLFLGWSTTRLGFGLTRFY
ScSTE6  736  YTFSFLLEGIVPSTDGKTGSSHYLAKWSLLVLGVAAADGIFNFAKGFLLDCCSEYWVMDL
SpPMD1  814  AVFARFLN--IFTDLSSTDFLHKVNVFAVYWLILAIVQFFAYAISNFAMTYAMEAVLQRI
ScPDR5  906  ASGAGKTT--LLDCLAERVTMGVITG-DILVNGIPRDKSFPRSIGYCQQQDLHLKTATVR
CaCDR1  896  ASGAGKTT--LLNCLSERVTTGIITDGERLVNGHALDSSFQRSIGYVQQQDVHLPTSTVR
MgABC1  932  VSGAGKTT--LLDCIADRTSMGVITG-EMLVDGHQRDASFQRKTGYVQQQDLHLQTTTVR

MgABC3  825  RKEYFKNMISRPASFFDEEDHTVGSLTARLATDPTQLQQLLGVNMAFVLVSIFNVIGCCI
ScSTE6  796  RNEVMEKLTRKNMDWFSGENNKASEISALVLNDLRDLRSLVSEFLSAMTSFVTVSTIGLI
SpPMD1  872  RYHLFRTLLRQDVEFFDRSENTVGAITTSLSTKIQSLEGLSGPTLGTFFQILTNIISVTI
ScPDR5  963  ESLRFSAYLRQPAEVSIEEKNRYVEEVIKILEMEKYADAVVGVAGEGLNVEQRKRLTIGV
CaCDR1  954  EALQFSAYLRQSNKISKKEKDDYVDYVIDLLEMTDYADALVGVAGEGLNVEQRKRLTIGV
MgABC1  989  EALNFSALLRQPAHVPRAEKLAYVDEVIRLLDMQEYADAVVGVPGEGLNVEQRKRLTIGV
```

FIG. 3B-2

```
MgABC3    885  VGFVFGWKLTIVSLAS------------TMPIIVVAMAYRVRHEVRLEAEASKVFAEGAR
ScSTE6    856  WALVSGWKLSLVCIS-------------MFPLIIIFSAIYGGILQKCETDYKTSVAQLEN
SpPMD1    932  LSLATGWKLGLVTLS-------------TSPVIITAGYYRVRALDQVQEKLSAAYKESAA
ScPDR5   1023  ELTAKPKLLVFLDEPTSGLDSQTAWSICQLMKKLANHGQAILCTIHQPSAILMQEFDRLL
CaCDR1   1014  ELVAKPKLLLFLDEPTSGLDSQTAWSICKLMRKLADHGQAILCTIHQPSALIMAEFDRLL
MgABC1   1049  ELAAKPPLLLFVDEPTSGLDSQTSWAILDLLEKLTKSGQAILCTIHQPSAMLFQRFDRLL

MgABC3    933  FASESIAAIRTVSSLTMEDGVGTRYEELLNKHVRQAFSKARWSLLLFSPSDSISFLCMAF
ScSTE6    903  CLYQIVTNIKTIKCLQAEFHFQLTYHDLKIKMQQIASKRAIATGFGISMTNMIVMCIQAI
SpPMD1    979  FACESTSAIRTVASLNREENVFAEYCDSLIKPGRESAIASLKSGLFFSAAQGVTFLINAL
ScPDR5   1083  FMQRGGKTVYFGDLGEGCKTMIDYFESHGAHKCPADANPAEWMLEVVGAAPGSHANQDYY
CaCDR1   1074  FLQKGGRTAYFGELGENCQTMINYFEKYGADPCPKEANPAEWMLQVVGAAPGSHAKQDYF
MgABC1   1109  FLAKGGKTVYFGDIGENSKIMTDYFERNGGFPCPHDANPAEWMLEVIGASPGTTSDIDWH

MgABC3    993  VLWYGGRLLASREYSPFQYVIVYIAVVQGAMSAGQWLSFGPNIAHATAAADRVLDMREAD
ScSTE6    963  IYYYGLKLVMIHEYTSKEMFTTFTLLLFTIMSCTSLVSQIPDISRGQRAASWIYRILDEK
SpPMD1   1039  TFWYGSTLMRKGEYNIVQFYTCFIAIVFGIQQAGQFFGYSADVTKAKAAAGEIKYLSESK
ScPDR5   1143  EVWRNSEEYRAVQSELDWMERELP-KKGSITAAEDKHEFSQSIIYQTKLVSIRLFQQYWR
CaCDR1   1134  EVWRNSSEYQAVREEINRMEAELS-KLPRDNDPEALLKYAAPLWKQYLLVSWRTIVQDWR
MgABC1   1169  QAWRESPECADVHAELDRLKEQVPNTPPPTEDKASYREFAAPFHQQIYAVTHRVFQQYWR

MgABC3   1053  DELDRGLPLIDPNEDAMLE---------EKEGAEVELRDVWFSYPTR-PGTILKGLDIKV
ScSTE6   1023  HNTLEVENNNARTVGIAGHTYHG-----KEKKPIVSIQNLTFAYPSAPTAFVYKNMNFDM
SpPMD1   1099  PKIDTWS-----TEGKKVE--------SLQSAAIEFRQVEFSYPTRRHIKVLRGLNLTV
ScPDR5   1202  SPDYLWSKFILTIFNQLFIGFTFFKAGTSLQGLQNQMLAVFMFTVIFNPILQQYLPSFVQ
CaCDR1   1193  SPGYIYSKIFLVVSAALFNGFSFFKAKNNMQGLQNQMFSVFMFFIPFNTLVQQMLPYFVK
MgABC1   1229  TPSYIYAKAALCAVTALFIGFVFYDAPNTQQGLQNQMFAIFNILTVFGQLVQQTMPHFVI

MgABC3   1103  ERGQFAAIVGPSGSGKTTVISLLERFYGADSGQVLYNGHDVLDLEPSAYRSNVSLVAQEP
ScSTE6   1078  FCGQTLGIIGESGTGKSTLVLLLTKLYNCEVGKIKIDGTDVNDWNLTSLRKEISVVEQKP
SpPMD1   1145  KPGQFVAFVGSSGCGKSTTIGLIERFYDCDNGAVLVDGVNVRDYNINDYRKQIALVSQEP
ScPDR5   1262  QRDLYEARERPSRTFSWISFIFAQIFVEVPWNILAGTIAYFIYYPIGFYSNASAAGQLH
CaCDR1   1253  QRDVYEVREAPSRTFSWFAFIAGQITSEIPYQVAVGTIAFFCWYYPLGLYNNATPTDSVN
MgABC1   1289  QRDLYEVRERPSKVYSWKVFMLSQIIVEIPWNSLMAVIMFFCWYYPVGLERNAILADQVT
```

FROM FIG. 3C-1

```
MgABC3   1163  ---------------HLLSGSMRDNVLLGIEDESTVVHADIYAACQEAGLHDFISSLPE
ScSTE6   1138  ---------------LLFNGTIRDNLTYGLQD--EILEIEMYDALKYVGIHDFVISSPQ
SpPMD1   1205  ---------------TLYQGTVRENIVLGAS--KDVSEEEMIEACKKANIHEFILGLPN
ScPDR5   1322  ERGALFWLFSCAFYVYVGSMGLLVISFNQVAESAANLASLLFTMSLSFCGVMTTPSAMPR
CaCDR1   1313  PRGVLMWMLVTAFYVYTATMGQLCMSFSELADNAANLATLLFTMCLNFCGVLAGPDVLPG
MgABC1   1349  ERGALAFLYLWGFLIFTSTFTDLMIAGFETAEAGGNIANLFFSLCLIFCGVLANPDTMPR

MgABC3   1207  GYSTEVGARGVALSGGQKQRLSIARALIRRPALLLLDEATSALDSETERAVQETFEATK-
ScSTE6   1180  GLDTRIDT--TLLSGGQAQRLCIARALLRKSKILILDECTSALDSVSSSIINEIVKKGP-
SpPMD1   1247  GYNTLCGQKGSSLSGGQKQRIAIARALIRNPKILLLDEATSALDSHSEKVVQEALNAAS-
ScPDR5   1382  FWIFMYRVSPLTYFIQALLAVGVANVDVKCADYELLEFTPPSGMTCGQYMEPYLQLAKTG
CaCDR1   1373  FWIFMYRCNPFTYLVQAMLSTGLANTFVKCAEREYVSVKPPNGESCSTYLDPYIKFAGG-
MgABC1   1409  FWIFMYRVSPFTYIVSGLLSVAVANSEVRCASNEFLHFDPLNG-TCAEFMRNYINGTTIP

MgABC3   1266  -------------------GSRTMIVVAHRLATVKNADVIFVMADGKVIEQGDHVS
ScSTE6   1237  -------------------PALLTMVITHSEQMMRSCNSIAVLKDGKVVERGNFDT
SpPMD1   1306  -------------------QGRTTVAIAHRLSSIQDADCIFVDGGVTCEAGTHAE
ScPDR5   1442  YLTDENATD-----------TCSFCQISTTNDYLANVNSFYSERWRNYGIFICYIAFNY
CaCDR1   1432  -YFETRNDG-----------SCAFCQMSSTNTFLKSVNSLYSERWRNFGIFIAFIAINI
MgABC1   1468  GLGRIPGAGGYLRPDTESSRSNCAFCPIKDTNIFLQGAHANYNDRWRNFGLIFVYIIFNI

MgABC3   1303  LLERRGVYYEMCQSQALDR-----------------------------------
ScSTE6   1274  LYNNRGELFQIVSNQSS----------------------------------
SpPMD1   1343  LVKQRGRYYELVVEQGLNKA-----------------------------
ScPDR5   1490  IAGVFFYWLARVPKKNGKLSKK-----------------------------
CaCDR1   1479  ILTVIFYWLARVPKGNREKKNKK----------------------------
MgABC1   1528  IAALFVYWAVRVPKKKLGGKDAAAGVGAGAGAARASASNEKGKMQREKGEVEGLTTAVLG
```

FIG. 3C-2

```
MgABC3    ------------------------------
ScSTE6    ------------------------------
SpPMD1    ------------------------------
ScPDR5    ------------------------------
CaCDR1    ------------------------------
MgABC1 1588 TSVAGSDAPMTTTTEGEGERAKRRTSGDEVVR
```

FIG. 3D

```
ATGACAGCGG CGACACCCGC TGATGGGGAG AAGGGCTTCA AGCTCAACCC GAAACATCTG TTGGCGATAC ACAACTTCAA
Ggttagtact agtctggact aaaaaaaaac ttgcaccagc taacgatgtt atagAGGATC TTGACATATG GCACAAAATG
GGACAAGATA GTGTTGGGAG TTTCAACGGT ATCGTCGGTG GCCACAGGCC TGACGATACC CTTGATGGTT GTCGTCTTTG
CCAGGCTCAT TGGCATATTT ACCGATTTTT ATCGCCAGGG GTCGACCGTG ACTGGCGCCC AGTTCAGCAG TCAGGTTAAC
CAATGTGTAT ACAACATCAT ATACCTCTTC GTGGCCAGGA TTATATTTTC CTACATCTCC AATgtaagac tctctcgtcc
tctcgagtat gcaatggcta acaaccacag CTTGGCTTTC GCATGTTCTC ACTGCGCATC TCCTCCACCA TCCGGACGGT
TTACCTTCGC TCTTTATTCG CGCTTCCCAT CTCAGTCATC GATGCAATCC CAGCCGGACA AACCGCCGCC ATAGTCACCG
GCACGGCAAG TGTGCTGCAG GTCGGCATAT CCGAAAAGCT GGGCGGTGGC ATCGCCAGCT TGGCCAGTGT CGCTTCTAGC
GTCGTTGTTG CCCTCGTCTT CAACTGGCTA CTAACTTTTG TGACCATTGC TGGGTTGGCT TTCATTGCCA TCGTGTACGT
CATTTTCACC CCTCTGGTTG GCAAAAAGGC TCTCGAGGTC CACGAGGCCG ATGTCAAGGC ATCCAGCATT GCCACAGAGG
CCTTTACTTC GGTCCGCATG CTGGCAGCAT GTGGTGCCGA GAACAAGGTC GCGCGCCGTT ATGCAGTCCA TGTGGATGAG
TCGTATCAAA AGGGCTTGCG AATGGCATGG CTTGTGGGAG TCCAGCAGAT GTTTGgtaag ttcccgcctc ctccttgatt
tagggatata ctgaccctga tagTCTTCTT TGGCGTATAC GCGACCTTTG CTCTCGCCTT TTACTTTGCC TTTCGCATGT
ACAACACCAG CATCACCACG ACCCCCGAGG ATCTTATAGT gtatgtatac ccatacctc atcgacaacc aaagctaact
tccacagCGT CCTTCTCTGC GTCATGATGA TGGCAACCTC GATCGGCCAG ATCACAGCCC CCTTGGCCGC TGCGCAACAG
GCAGCAGAGG CTTGTGGCAT CTTCCATACC ATCATCGACT TTCCGAAGCC GGTCTACGGA TCTGCCAGAG GAGAGCATGA
AGTCCGGGCA GATGGCGACA TTGTCCTCAT GAATGTCAAC TTTGCTTACC CGACCCGCCC AGAGGTCAAG GTTCTCGATA
ATCTATCTCT GGTGTTCCCT GCGGGCAAGG TTACTGCGAT CGTGGGTCCG TCTGGTTCCC GCAAATCCAC CATCGTTGGC
ATCCTGGAGC GCTGGTACGA GTTCAATGGT GATCCGGTCT TAAACCCACT Ggtaagaaac cccaaccctc aagcttctc
agctaacaag aagcagGTCC TCTACCTTCG CAACGGATTT GTATCTGTAG GCGGACGCCT TCTCACCGAA ATCGACGTCA
AATGGTGGCG CAACCAGATA GGCCTGGTTC AGCAAGACAA TGTGCTCTTC AACACGACAA TTTACAAAAA CGTCGAGCAT
GGGCTGATCG GCACGCTGTG GGAGCATGAG AGCGACGAGA AAAAGGCCAT GCTGATTGAG ACTGCATGCC GGGATGCGTT
TGCCGACGAG TTCATCAACC GTCTCCCAGA Cgtaagtatc tcactgtatc cccatgatga tctcattact gacgcacagg
cagCGCTACC AAACAACCGT GGGTGAATCA GGAATCAAGC TCAGTGGAGG TCAACGTCAA CGTCTCGCCA TCGCCGCGC
AATCGTCAAG CAGCCCAAGA TCCTCATCCT CGACGAGGCA ACCTCCGCCA TCGACGTGCG CAGCGAACAA ATCGTTCAAG
CCGCCCTTGA GCGGGCCAGC CGTGGACGCA CCACCGTCGT GATTGCCCAC CGTCTCGGCA CTGTCAAAAA GGCCGACAAG
ATCATCGTGC TGAGCAAAGG CCAGGTGGTG CAGGAGGGCA CGCACGACGA GCTGCGGAGG CAAAGGGGTA GTGCGTACTA
CATGCTGCGG AATGCTCAAA GCCTAAACGT CCGTCGGCGC TCGAGCAGAA TGAGCATCGA CCAGACTCCG GACGAAGAGG
ATGACAGCGG TTATTTTAGG ACGACGTCGA TGCACGATGG CGATTCTGAC CACACGGCCC ACTCTTCCAA CTATGGATCG
GATGAAGAGG ACGACTTCAT CATGGAGAGG CCTAGGGTGC GTGCTCGTGA CGATGTGGGT GTGGAGATGT CGACCAGTAC
CATCCACACC GCGCATACTC CCGTGTCCGA TGGCCCGCCA GATGACGCCG CAAAGATCCA GGTGGTCGAG ATTCAAGACC
ACTGGCTTGG TGGTTTCGCC GAACTGTTGG CGGAGCAAGG ATCGAGGTGG AAGCTGTATT TTGTCATCAT CATAGGAGCT
ATTGGAGCAG GTGgtaagtt gatcttgatc caatgctagg tggcgtccac tgacaaccaa cagCAAGCAC ACCGGTGCAA
GCATACCTCT TCGCAACTCT CCTCAACCTC TTTTCCTTCA GAGGTCCACA GGTCAACCAA CTCGCCAATT TCTTTTGTCT
CATGTTCGTG GTGCTGGCAG CGGGCGTTGG CATCAGTCAT TTGTTCCTAG GATGGTCGAC GACGCGACTG GGTTTCGGCT
TGACCCGCTT CTACCGAAAG GAGTACTTCA AGAACATGAT CAGCCGACCG GCGTCCTTCT TCGACGAGGA GGACCACACA
GTGGGCTCGT TGACGGCTAG GTTGGCTACA GACCCAACGC AGCTGCAGCA GCTCCTCGGC GTTAACATGG CATTTGTGCT
CGTGTCCATT TTCAACGTCA TCGGGTGTTG TATCGTCGGC TTCGTGTTTG GATGGAAATT GACAATCGTG TCTTTGGCGT
CGACAATGCC CATCATCGTG GTTGCTATGG CCTATCGCGT GCGGCATGAG GTCCGCCTTG AGGCTGAAGC AAGCAAGGTT
TTCGCTGAAG GCGCCCGATT CGCATCCGAA AGCATCGCTG CGATCCGGAC CGTGTCCAGC TTGACCATGG AAGACGGCGT
CGGAACCAGA TATGAGGAGC TGTTGAACAA ACACGTCCGT CAGGCTTTCA GCAAGGCCAG GTGGTCGCTG CTGTTGTTTT
CCTTTAGTGA CAGTATTTCA TTTCTCTGCA TGGCTTTCGT CTTGTGgtaa gtactgtgct gatgcactgg gcaatcgcga
atgctgactt tttcagGTAC GGTGGTCGAC TGCTGCCAG TCGGGAGTAC AGCCCCTTCC AATATGgtga gttcagtctc
tctgattttg ccgtgctctt actaacatac gatagTGATT GTGTACATTG CCGTTGTTCA Ggtaagaatc aaaccatcac
```

FROM FIG. 8A

gtgcgacagc aggactttac taactccaac agGGTGCAAT GAGTGCCGGA CAATGGTTGA GCTTCGGTCC CAgtgagtaa
cccccatgt gcactccaca gcgatgcgtg ctaacttgaa cagATATCGC CCATGCTACC GCCGCAGCCG ATCGGGTTCT
TGATATGCGA GAAGCCGATG ACGAACTCGA CCGTGGCTTG CCTTTAATCG ACCCCAACGA AGATGCCATG CTGGAAGAGA
AAGAAGGTGC CGAAGTAGAG CTGCGCGACG TGTGGTTCAG CTACCCGACC CGACCCGGAA CAATCCTCAA AGGCCTAGAC
ATCAAGGTTG AACGTGGACA GTTTGCTGCC ATCGTTGGCC CATCCGGTTC AGGAAAGACG ACAGTCATCT CTCTGTTGGA
GCGCTTCTAT GGCGCTGATT CGGGCCAGGT CCTGTACAAC GGCCACGATG TGCTGGACCT CGAGCCTTCG GCGTACCGGT
CCAACGTGTC GCTCGTGGCA CAGGAGCCAC ATCTTCTCAG TGGGTCGATG CGCGATAATG TACTGCTCGG CATTGAAGAC
GAGTCGACCG TGGTTCATGC CGACATCTAC GCCGCGTGTC AAGAGGCAGG ACTGCACGAC TTCATCTCGT CGCTACCCGA
AGGGTATTCC ACCGAAGTCG GAGCACGAGG TGTGGCTCTT TCTGGAGGCC AGAAGCAGCG TCTTTCCATC GCCCGTGCTT
TGATCCGCCG TCCGGCTTTG TTGCTCCTCG ATGAGGCAAC CAGTGCCCTT GACAGCGAGA CGGAGAGGGC GGTGCAGGAG
ACCTTTGAAG CCACCAAAGG CAGCAGAACA ATGATTGTTG TCGCACATCG TTTGGCAACA GTCAAAAACG CAGATGTCAT
TTTCGTCATG GCGGACGGAA AGGTCATTGA GCAGGGCGAC CATGTCTCCT TGCTGGAAAG GAGAGGAGTC TACTATGAAA
TGgtaagttt tcccgtgcgt gtccaacctg ggtcaatgct aactgccggg tgtaacagTG TCAATCTCAA GCATTGGACA
GGTGA  (SEQ ID NO:1)

FIG. 8B

```
MTAATPADGEKGFKLNPKHLLAIHNFKRILTYGTKWDKIVLGVSTVSSVATGLTIPLMVV
VFARLIGIPTDFYRQGSTVTGAQFSSQVNQCVYNIIYLFVARIIFSYISNLGFRMFSLRI
SSTIRTVYLRSLFALPISVIDAIPAGQTAAIVTGTASLLQVGISEKLGGGIASLASVASS
VVVALVFNWLLTFVTIAGLAFIAIVYVIFTPLVGKKALEVHEADVKASSIATEAFTSVRM
LAACGAENKVARRYAVHVDESYQKGLRMAWLVGVQQMFVFFGVYATFALAFYFAFRMYNT
SITTTPEDLIVVLLCVMMMATSIGQITAPLAAAQQAAEACGIFHTIIDFPKPVYGSARGE
HEVRADGDIVLMNVNFAYPTRPEVKVLDNLSLVFPAGKVTAIVGPSGSGKSTIVGILERW
YEFNGDPVLNPLVLYLRNGFVSVGGRLLTEIDVKWWRNQIGLVQQDNVLFNTTIYKNVEH
GLIGTLWEHESDEKKAMLIETACRDAFADEFINRLPDRYQTTVGESGIKLSGGQRQRLAI
ARAIVKQPKILILDEATSAIDVRSEQIVQAALERASRGRTTVVIAHRLGTVKKADKIIVL
SKGQVVQEGTHDELRRQRGSAYYMLANAQSLNVRRRSSRMSIDQTPDEEDDSGYFRTTSM
HDGDSDHTAHSSNYGSDEEDDFIMERPRVRARDDVGVEMSTSTIHTAHTPVSDGPPDDAA
KIQVVEIQDHWLGGFAELLAEQGSRWKLYFVIIIGAIGAGASTPVQAYLFATLLNLFSFR
GPQVNQLANFFCLMFVVLAAGVGISHLFLGWSTTRLGFGLTRFYRKEYFKNMISRPASFF
DEEDHTVGSLTARLATDPTQLQQLLGVNMAFVLVSIFNVIGCCIVGFVFGWKLTIVSLAS
TMPIIVVAMAYRVRHEVRLEAEASKVFAEGARFASESIAAIRTVSSLTMEDGVGTRYEEL
LNKHVRQAFSKARWSLLLFSFSDSISFLCMAFVLWYGGRLLASREYSPFQYVIVYIAVVQ
GAMSAGQWLSFGPNIAHATAAADRVLDMREADDELDRGLPLIDPNEDAMLEEKEGAEVEL
RDVWFSYPTRPGTILKGLDIKVERGQFAAIVGPSGSGKTTVISLLERFYGADSGQVLYNG
HDVLDLEPSAYRSNVSLVAQEPHLLSGSMRDNVLLGIEDESTVVHADIYAACQEAGLHDF
ISSLPEGYSTEVGARGVALSGGQKQRLSIARALIRRPALLLLDEATSALDSETERAVQET
FEATKGSRTMIVVAHRLATVKNADVIFVMADGKVIEQGDHVSLLERRGVYYEMCQSQALD
R     (SEQ ID NO:2)
```

FIG. 9

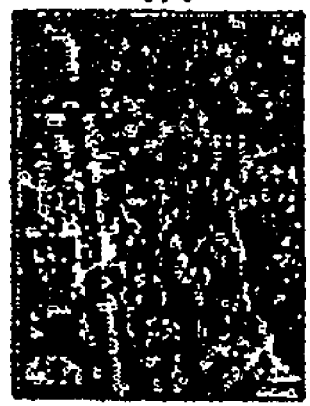
FIG. 18

| abc3Δ extract | WT extract | control |
|---|---|---|
| 14±1.2 | 39±3.5 | 52±1.9 |
| 46±2.6 | 49±1.4 | 57±3.1 |

FIG. 40

SYSTEM FOR INHIBITING PATHOGENICITY IN THE RICE-BLAST FUNGUS *MAGNAPORTHE GRISEA*

This application is a 35 U.S.C. §371 National Entry Application from PCT/SG2007/000071, filed Mar. 14, 2007 which claims the benefit of prior co-pending provisional application Ser. No. 60/782,515, filed Mar. 16, 2006, the entire contents of each of which are hereby incorporated herein by reference.

BACKGROUND OF THE INVENTION

1. Technical Field

This invention relates to the field of molecular biology and plant fungal disease. In particular, the invention relates to the discovery of a fungal protein that is essential for pathogenicity in *Magnaporthe grisea*, a plant pathogen.

2. Description of the Background Art

The ascomycete *Magnaporthe grisea* causes disease in several monocot plant species, including blast disease in the important crop rice, and represents a model system to study fungal-plant interaction. See Ou et al., *Rice Diseases*, Commonwealth Mycological Institute, Surrey, 1985; Valent et al., "Rice blast as a model system for plant pathology" Phytopathology 80:33-36, 1990. Rice blast disease is an important problem in rice cultivation and a major threat to food security around the world, causing very significant crop losses annually. *M. grisea* also can cause diseases in a number of other important cereal crops such as wheat, rye and barley, and also in weed and turf grasses.

The asexual life cycle of *M. grisea* involves sporulation of the fungal hyphae to produce fruiting structures called conidia. The conidia contain many spores, which germinate in a suitable environment on a host plant, and develop to form a specialized infection structure termed an appressorium. These appressoria penetrate the plant cell by producing a penetration peg that is forced through the plant cell wall to begin infection. Upon entry of the fungus into the host cells, the fungus proliferates by forming penetration and infectious hyphae that establish and spread the disease lesions. See Hamer and Talbot, "Infection-related development in the rice blast fungus *Magnaporthe grisea*." Curr. Opin. Microbiol., 1:693-697, 1998; Talbot, "On the trail of a cereal killer: Exploring the biology of *Magnaporthe grisea*" Annu. Rev. Microbiol. 57:177-202, 2003. Infection of immature plants often is fatal. While mature plants usually survive, crop yield is considerably curtailed due to reduced photosynthesis and use of photosynthate by the invading fungal hyphae.

Currently, outbreaks of blast disease are controlled by applying expensive and toxic fungicidal chemicals such as probenazole, tricyclazole, pyroquilon and phthalide, or by burning infected crops. These methods are only partially successful since the fungus can develop resistance to the chemical agents and weed grasses may serve as a disease reservoir after burning. Clearly, improvements are needed in methods to control blast disease in rice and other cereal crops.

Transmembrane proteins belonging to the ubiquitous ATP-binding cassette (ABC) superfamily have been identified in several genera of prokaryotes and eukaryotes, including fungi. See Higgins, "ABC transporters: from microorganisms to man" Annu. Rev. Cell Biol. 8:67-113, 1992. The P-glycoproteins are a subfamily of plasma membrane-localized ABC transporters that modulate a multi-drug resistance (MDR)-related efflux of a broad range of compounds such as sugars, inorganic ions, heavy metal ions, peptides, lipids, metabolic poisons and drugs to effectively reduce the cellular accumulation of toxic compounds by efflux from the inner leaflet of the plasma membrane to the cell exterior. See Kolaczkowski et al., "In vivo characterization of the drug resistance profile of the major ABC transporters and other components of the yeast pleiotropic drug resistance network" Microb. Drug Resist. 4:143-158, 1998; Driessen et al., "Diversity of transport mechanisms: common structural principles" Trends Biochem. Sci., 25:397-401, 2000. ABC transporters play a major role in multidrug resistance (MDR), a mechanism that operates in mammalian tumor cells. The MDR subfamily of efflux pumps includes the multidrug resistance P-glycoproteins. Several MDR-type P-glycoproteins have been shown to catalyze the ATP-dependent efflux of anti-tumor agents during cancer chemotherapy. See Cole et al., "Overexpression of a transporter gene in a multidrug-resistant human lung cancer cell line" Science, 258:1650-1654, 1992; Gottesman and Pastan, "Biochemistry of multidrug resistance mediated by the multidrug transporter" Annu. Rev. Biochem., 62:385-427, 1993.

Identification and subsequent sequence comparisons of more than a hundred genes encoding ABC transporters show that the ABC proteins have one or two well-conserved nucleotide-binding folds of approximately 200 amino acid residues and the Walker A and B motifs as well as the SGG(Q) signature. Michaelis and Berkower, "Sequence comparison of yeast ATP-binding cassette proteins" Cold Spring Harbor Symp., Quant. Biol. LX:291-307, 1995. Several members of this large superfamily transport cytotoxic agents across biological membranes, reducing the intracellular level of toxins and metabolites. Driessen et al., "Diversity of transport mechanisms: common structural principles" Trends Biochem. Sci. 25:397-401, 2000.

In filamentous fungi, ABC transporter activity likely is involved in energy-dependent efflux of fungicides or phytoalexins in *Aspergillus nidulans* (Andrade et al., "The ABC transporter AtrB from *Aspergillus nidulans* mediates resistance to all major classes of fungicides and some natural toxic compounds" Microbiology, 146:1987-1997, 2000; Andrade et al., "The role of ABC transporters from *Aspergillus nidulans* in protection against cytotoxic agents and in antibiotic production" Mol. Gen. Genet., 263:966-977, 2000), *A. fumigatus* (Tobin et al., "Genes encoding multiple drug resistance-like proteins in *Aspergillus fumigatus* and *Aspergillus flavus*" Gene, 200:11-23, 1997), *Botrytis cinerea* (Vermeulen et al., "The ABC transporter BcatrB from *Botrytis cinerea* is a determinant of the activity of the phenylpyrrole fungicide fludioxonil" Pest Manag. Sci. 57:393-402, 2001), *M. grisea* (Urban et al., "An ATP-driven efflux pump is a novel pathogenicity factor in rice blast disease" EMBO J. 18:512-521, 1999), *Gibberella pulicaris* (Fleissner et al., "An ATP-binding cassette multidrug-resistance transporter is necessary for tolerance of *Gibberella pulicaris* to phytoalexins and virulence on potato tubers" Mol. Plant-Microbe Interact. 15: 102-108, 2002) and *Mycosphaerella graminicola* (Stergiopoulos et al., "The ABC transporter MgAtr4 is a virulence factor of *Mycosphaerella graminicola* that affects colonization of substomatal cavities in wheat leaves" Mol. Plant Microbe Interact. 16:689-698, 2003; Zwiers et al., "ABC transporters of the wheat pathogen *Mycosphaerella graminicola* function as protectants against biotic and xenobiotic toxic compounds" Mol. Genet. Genomics 269:499-507, 2003). However, none of these previously known fungal transporter molecules belong to the P-glycoprotein or MDR subfamily of the ABC transporters.

SUMMARY OF THE INVENTION

Embodiments of the invention described and claimed herein include an abc3 gene of SEQ ID NO:1 and an ABC3 protein of SEQ ID NO:2. The invention's embodiments also include an isolated nucleic acid encoding the protein-coding region of the abc3 gene, which can be selected from those of *Magnaporthe, Aspergillus, Ustilago* or *Fusarium* species abc3 gene, for example.

An embodiment of the invention is the abc3 gene, which preferably is SEQ ID NO:1. A further embodiment of the invention is an ABC3 protein, which preferably is SEQ ID NO:2. Included in the invention are nucleic acids that encode an ABC3 protein as listed above and described herein.

Further embodiments of the invention include a method of rendering plant pathogenic species including *Magnaporthe* species, such as *Magnaporthe grisea*, or *Aspergillus, Ustilago* or *Fusarium* species, non-pathogenic to a plant by applying an ABC3 inhibitor to the plant or expressing an ABC3 inhibitor in the plant. ABC3 inhibitors may be selected from a peptide, a nucleic acid that encodes the peptide, a protein, a nucleic acid that encodes the protein, a peptide-mimetic compound, an organic chemical, a replacement plasmid vector, an antisense nucleic acid or any combination thereof. One example of an ABC3 inhibitor is pFGLabcKO.

BRIEF DESCRIPTION OF THE DRAWINGS

FIG. 1 is a phylogram of MDR proteins related to Abc3 protein, depicting the phylogenetic relatedness of *Magnaporthe* ABC1 and ABC1 proteins with the MDR or ABC proteins from the yeasts *Saccharomyces* (ScSTE6 and ScPDR5) *Schizosaccharomyces* (SpPMD1), and *Candida* (CaCDR1). The evolutionary distance scale (Mya) and the branch lengths are indicated. Bootstrapping (1000 replicates/iterations) was used to generate the phylogenetic tree using the MEGA 3.1 Neighbor-joining algorithm.

FIG. 2 is a phylogram of MDR proteins related to Abc3 protein, depicting the most parsimonious phylogenetic relatedness of *Magnaporthe* ABC3 protein with the MDR proteins from the indicated genera within eukaryotes.

FIG. 3 is a multiple sequence alignment used for the phylogenetic analysis of ABC3-related MDR proteins. MgABC3 (*Magnaporthe grisea*)=SEQ ID NO: 25; ScSTE6 (*Saccharomyces ceriviseae*)=SEQ ID NO:26; SpPMDI (*Schizosaccharomyces pombe*)=SEQ ID NO: 27; ScPDR5 (*Saccharomyces ceriviseae*)=SV.Q ID NO:28; CaCDRI (*Candida albicans*)=SEQ ID NO:29; MgABCI (*Magnaporthe grisea*)=SEQ ID NO: 30.

FIGS. 4A and 4B are photographs of barley leaf explants inoculated with conidiospores of TMT2807 or wild-type (WT) strain.

FIGS. 5A and 5B are photographs of barley leaf explants inoculated with conidiospores of TMT2807 or wild-type (WT) strain.

FIG. 6 is a schematic representation of the annotated ABC3 locus spanning a HindIII-PvuII fragment from Contig 67 on Supercontig 5.117 in *M. grisea*.

FIGS. 7A and 7B show Southern blot analyses of the ABC3 mutants and the Complemented strain.

FIG. 8 shows the gene sequence of abc3 (SEQ ID NO:1). Exons are shown in upper case letters; introns are shown in lower case letters.

FIG. 9 shows the protein sequence of ABC3 (SEQ ID NO:2).

FIG. 10 is a photograph of a wild-type, an abc3Δ mutant and an abc3Δ strain complemented with the full length ABC3 (Comp). The strains were grown on complete medium for a week and photographed. Scale bar=1 cm.

FIG. 11 is a bar graph showing perithecia development by the indicated *Magnaporthe* strains in individual sexual crosses with the tester strain of the opposite mating type, assessed 3 weeks post inoculation.

FIG. 12 is a photograph of conidia from the wild type or abc3Δ strain which were allowed to germinate on complete medium for 16 hours and then visualized after acid fuchsin staining. Bar=20 microns.

FIGS. 13A and 13B are photographs showing the morphology of appressoria 24 hours after inoculation on a hydrophobic inductive surface. Bar=10 mm.

FIG. 14 shows hypersensitivity-reaction (HR) assessed 48 hours after infection with *Magnaporthe* strains and represent the ratio of rice Pr-1 gene expression to that of the Actin transcript. Bar=1 cm.

FIG. 15 shows barley leaves challenged with wild type or abc3Δ conidia and co-stained with DAB and Trypan blue to detect peroxide- and HR-associated cell death, respectively. The arrowhead indicates a rare HR event in the host upon challenge with the mutant.

FIG. 16 shows conidia from wild type or abc3Δ mutant inoculated on abraded barley leaves (FIG. 17, upper panels) or injected at the base of barley leaves (FIG. 17, central panels) or the base of rice-leaf sheaths (FIG. 17, bottom panels). Bar 0.5 cm.

FIG. 17 shows equivalent numbers of conidia from wild type or abc3Δ mutant were inoculated onto synthetic membranes (PUDO-193 cellophane) and assessed for germination, appressoria formation, surface penetration and invasive growth. The arrowhead indicates invasive growth. Bar=10 mm.

FIG. 18 is a photograph of penetration and invasion 48 hours after inoculation on onion epidermal strips. Bar=10 mm.

FIG. 19 is a photograph of penetration and invasion 48 hours after inoculation on barley leaf explants. Bar=10 mm.

FIG. 20 shows data for appressorium formation at 24 hours and appressorium function (host penetration and invasion, as judged by aniline blue staining of resultant callose deposits) at 48 hours (wild type, shaded; abc3Δ mutant, black).

FIG. 21 is a set of transmission electron photomicrographs showing barley leaves challenged with conidia from wild type or abc3Δ mutant at the indicated time points. Bar=2 mm, except for the middle right panel where it denotes 1 mm.

FIG. 22 is a pair of photographs showing wild type or abc3Δ mutant conidia, inoculated on Barley-leaf explants, onion epidermal strips or rice-leaf sheaths and processed for aniline blue staining after 72 hours.

FIG. 23 is a bar graph presenting quantified data from FIGS. 21 and 22.

FIG. 24 shows the results of an appressorial assay performed in a host or on cellophane, comparing viability and invasive growth of wild type and abc3Δ mutant conidia.

FIG. 25 is a photograph showing serial dilutions of wild type or abc3Δ conidial suspensions, cultured in the presence (20 mg/ml) or absence (0 mg/ml) of Valinomycin on complete growth medium for 5 days.

FIG. 26 is a photograph of wild type or abc3Δ conidial suspensions, cultured in the presence (20 mg/ml) or absence (0 mg/ml) of Valinomycin on artificial inductive membranes for 36 hours. Bar=15 mm.

FIG. 27 shows fission yeast strains as indicated after 5 days growth on YES medium in the presence or absence of Valinomycin.

FIG. 28 shows mycelial plugs from the wild type or abc3Δ strain cultured on minimal agar medium with the indicated amounts of hydrogen peroxide.

Figure 39:
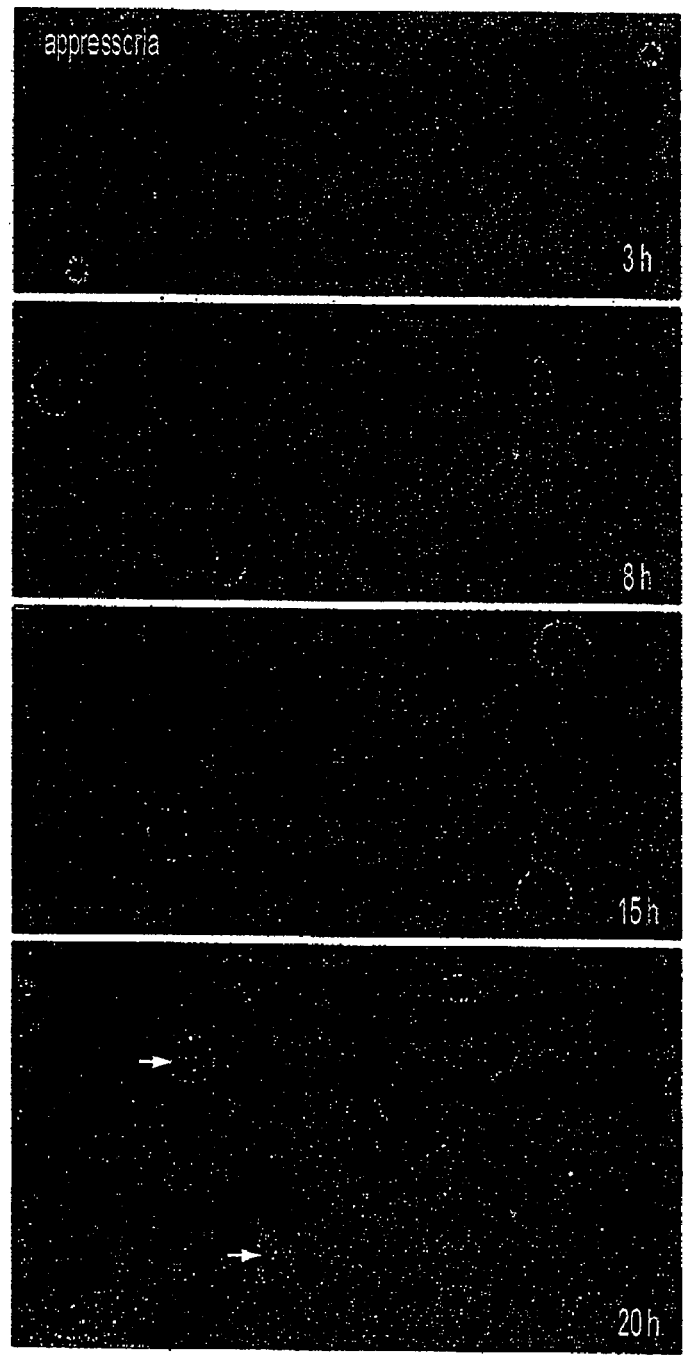

FIG. 39 shows appressorium development over the indicated time course, imaged using GFP epifluorescence. The bar equals 10 mm. Arrowheads indicate the vacuolar distribution of ABC3-GFP.

FIG. 40 is a set of photographs showing the effect of intracellular and extracellular extracts prepared from the appressoria of the wild type or abc3Δ strain in barley leaf infection assays.

Figure 41:
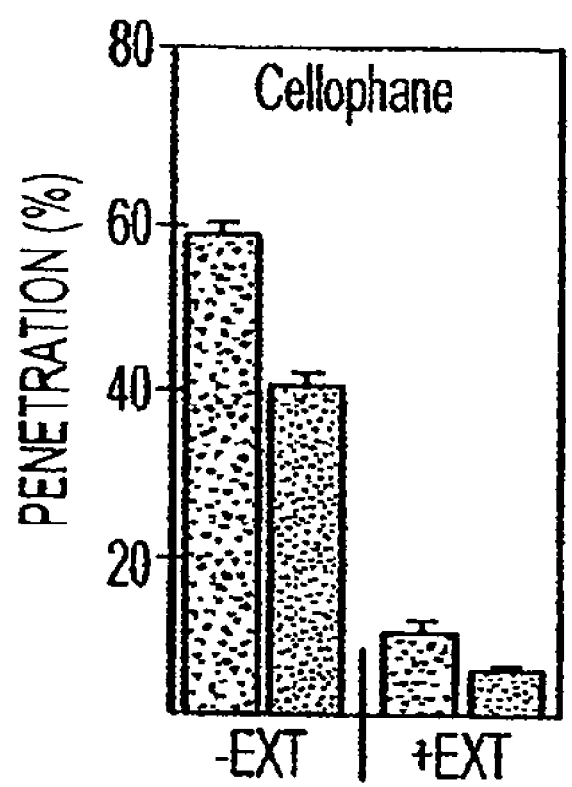

FIG. 41 is a bar graph showing appressorium function in the absence or presence of the intracellular neutral extract from the abc3Δ mutant. Values represent mean±SD from three replicates of the experiments.

Figure 42:
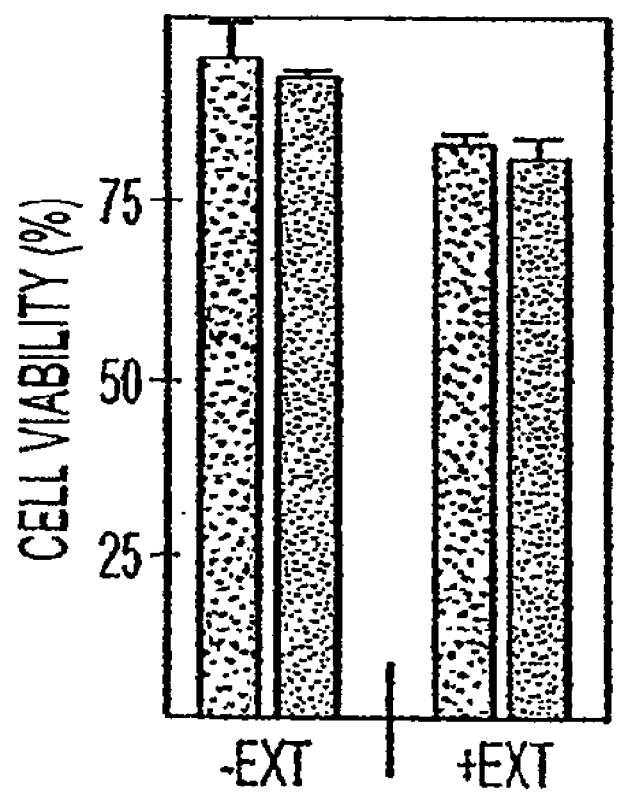

FIG. 42 is a bar graph showing cell viability assessed with Phloxine B staining in vegetative mycelia from the wild type (gray) or abc3Δ (black) strains.

Figure 43:
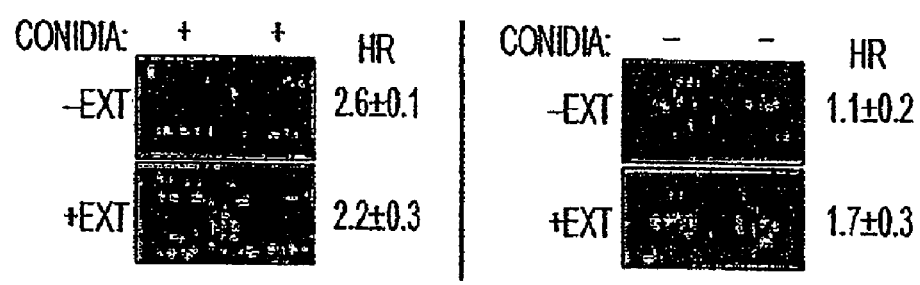

FIG. 43 shows the results of barley-leaf inoculation assays in the absence (−EXT; solvent control) or presence (+EXT; at 1× or 0.5× concentration) with wild type conidia.

Figure 44:
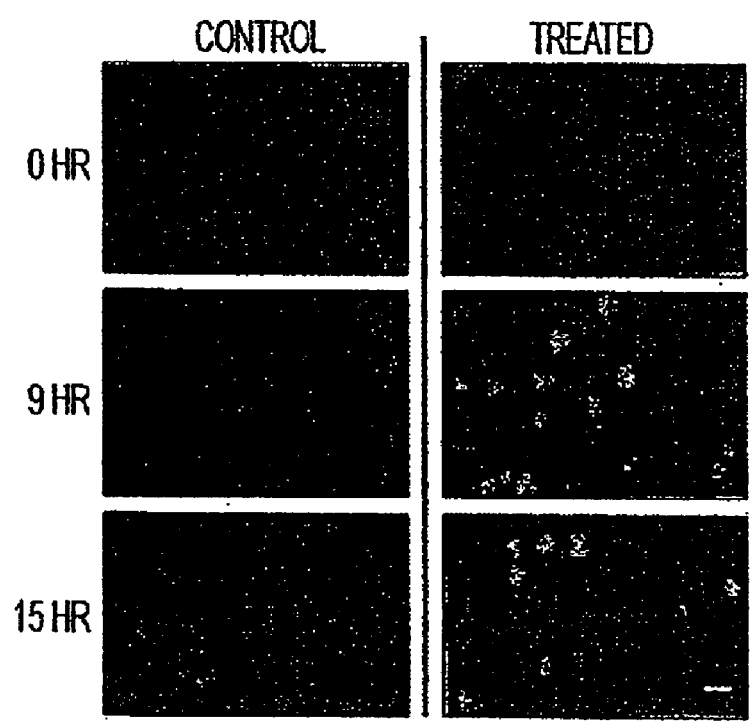

FIG. 44 is a set of epifluorescent photomicrographs showing conidia from the ABC3(p)::deGFP strain which were allowed to undergo appressorium development for 24 hours in the absence (Control) or presence (Treated) of 1 mM hydrogen peroxide. Bar=10 mm.

Figure 45:
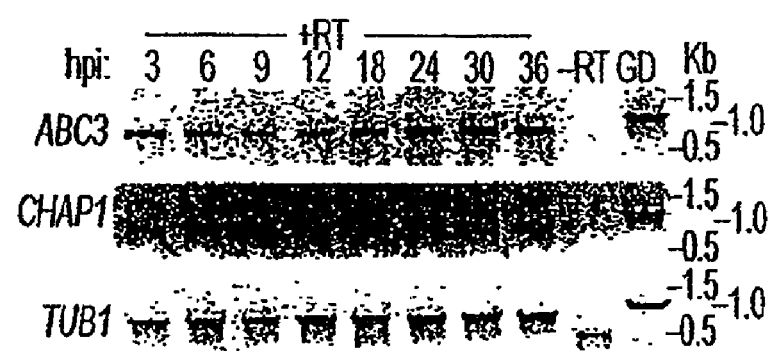

FIG. 45 shows results of semi-quantitative RT-PCR amplification using ABC3 or MgCHAP1 or MgTUB1 specific primers from total RNA extracted from the wild type strain grown for the indicated hours post inoculation (hpi) on barley leaves.

DETAILED DESCRIPTION OF THE PREFERRED EMBODIMENTS

To successfully invade a host plant and to cause blast disease, phytopathogenic fungi such as *M. grisea* need to adapt to the specific environment of the host and overcome or survive the cytotoxic and antifungal compounds or phytoalexins produced by the plant hosts. See Dixon et al., "Early events in the activation of plant defense responses." Annu. Rev. Phytopathol. 32:479-501, 1994; Kodama et al., "Sakuranetin, a flavonone phytoalexin from ultraviolet-irradiated rice leaves." Phytochemistry 31:3807-3809, 1992; Osbourn, "Preformed Antimicrobial Compounds and Plant Defense against Fungal Attack" Plant Cell 8:1821-1831, 1996. Intragenome BLAST (*Magnaporthe* Genome Database, Broad Institute, USA) computer searches revealed that the *Magnaporthe* genome encodes at least 76 ABC-like transporters.

The gene discovered here was found to be unique and showed scant similarity to the other ABC molecules within the *Magnaporthe* genome and proteome, and thus failed to predict any true orthologs. The data presented here showed that ABC3 protein is a transmembrane protein enriched in the outer membranes of the infection structure. A significant distribution of ABC3 protein also was observed in the vacuoles during the late stages of appressorium formation. Host infection data clearly showed that ABC3 protein has acquired a more specialized role in pathogenicity during its evolution from or along with the yeast orthologs.

TMT2807 was isolated as a non-pathogenic mutant in *Magnaporthe*. Molecular genetics and further characterization of TMT2807 enabled identification of the MDR P-glycoprotein encoding gene abc3 as a pathogenicity factor in *Magnaporthe*. To confirm the role of ABC3 protein in *Magnaporthe* pathogenesis, abc3Δ mutants were created and characterized in two separate wild type backgrounds (Guy11 and B157). The studies clearly demonstrated that loss of ABC3 protein in *Magnaporthe* completely destroys pathogenicity towards rice and barley. The abc3Δ colonies were slow growing compared to the corresponding wild type, but were largely unaffected in morphology and in conidia formation. Genetic complementation analyses confirmed that the defects seen in the TMT2807 and abc3Δ strains were due solely to the loss of ABC3 function.

Mutational analysis of the gene abc3, has allowed definition of an important role for MDR-based efflux during the host penetration step of *Magnaporthe* pathogenesis. Mutants lacking the abc3 gene (abc3Δ) were completely nonpathogenic, but surprisingly were capable of penetrating thin cellophane membranes to a limited extent. Studies described below showed that the inability of abc3Δ to penetrate the host surface is most likely due to excessive buildup of peroxide and accumulation of inhibitory metabolite(s) within the mutant appressoria. Treatment with antioxidants partially suppressed the host penetration defects in the abc3Δ mutant. The amount of the inhibitory metabolite(s) and/or the timing of their production may be the limiting factors that allow the mutant to escape the maximal activity of these inhibitors on cellophane. Another likely possibility is that maximum turgor generation is probably not necessary on cellophane surfaces.

ABC3 protein is required for *Magnaporthe* pathogenesis. Its function is most likely critical at the host penetration step during blast disease establishment. The vast majority (~99%) of abc3Δ appressoria lacking ABC3 function failed to breach the host surface even upon extended incubation. Using papillary callose deposits and TEM analyses, it was discovered that only a negligible number of mutant appressoria made futile attempts at host penetration, however the fungus was able to elicit weak hypersensitivity reaction within the host tissue during compatible and incompatible interactions, as well as upon host inoculation through wounds or by injection.

The abc3Δ mutant was highly sensitive to oxidative stress and was unable to survive the host environment and invasive growth conditions. The ABC3 transcript was upregulated at the early stages of plant infection.

The studies reported here have determined that functional ABC3 is required for proper operation of appressoria (infection structures) during the initial pathogenic phase of rice-blast fungus. Without ABC3 function, host penetration during the disease establishment phase does not take place. As a consequence, mutants lacking operational ABC3 are completely nonpathogenic. Fungal mycelia and appressoria from the ABC3-deleted strain showed a multidrug-sensitive phenotype when tested with several different classes of peptide antibiotics such as valinomycin. This suggests that ABC3 protein is required for the efflux of these or other toxic compounds across the fungal membrane under normal circumstances.

ABC3 protein transcript levels were redox-responsive, and on host surfaces, activation of ABC3 occurred during initial stages of blast disease establishment. Model compounds of oxygen radical production, such as paraquat and hydrogen peroxide, modulated ABC3 protein levels in a redox-sensitive manner. Cells lacking ABC3 protein were sensitive to oxidative stress but not to osmotic shock or nutrient deprivation. This suggests that the loss of appressorium function in abc3Δ mutants is a consequence of the mutant's inability to cope with cytotoxic and oxidative stress. The data presented here therefore indicate that ABC3 function helps *Magnaporthe* to cope with cytotoxicity and oxidative stress within the appressoria during early stages of infection-related morphogenesis and that it likely imparts a defense against certain antagonistic and xenobiotic conditions encountered during pathogenic development.

Thus, ABC3 function provides the blast fungus with an important defense against the xenobiotic and antagonistic environment encountered on and in the host plant. Taking advantage of this mechanism, embodiments of the invention provide a method of combatting blast diseases caused by *M. grisea* or any other fungus expressing ABC3 protein by inhibiting the protein function in the plant or plant environment. This may be accomplished by applying ABC3 inhibitors to the plant or the environment around the plant or by causing the plant to express inhibitors.

Exogenously applied intracellular extracts from abc3Δ appressoria reduced the wild type strain's ability to penetrate host surfaces and cellophane membranes. This suggests that the abc3Δ mutant is defective in toxic metabolite efflux and that ABC3 transporter activity is most probably required for the timely efflux of certain inhibitory metabolite(s) during the host penetration step of blast infections. The accumulation of these toxic metabolites in appressoria likely causes penetration inhibition. Exogenous addition of the toxic metabolite(s) during wild type infection assays discernibly reduced blast symptoms, but hyper-sensitivity reaction was noticeable in the host leaf even in the absence of the blast fungus.

Cytorrhysis assays (Howard et al., "Penetration of hand substrates by a fungus employing enormous turgor pressures" Proc. Natl. Acad. Sci. USA, 88:11281-11284, 1991; de Jong et al., "Glycerol generates turgor pressure in rice blast" Nature, 389:244-245, 1997) revealed that there was no significant reduction in the overall turgor generated by abc3Δ appressoria, despite having an average size slightly larger than the wild type appressoria. The abc3Δ appressoria were capable of penetrating cellophane membranes, albeit less efficiently than the wild type strain. Subsequent invasive growth and spread within the cellophane membranes were however significantly compromised in the abc3Δ mutant, which also showed reduced viability under these conditions.

To begin this study, a forward genetics approach was used to isolate a mutant, TMT2807, of the rice-blast fungus *Magnaporthe grisea*. TMT2807 was identified as a mutant incapable of causing blast disease on barley leaves although its infection structure formation appeared normal. Molecular genetics and further characterization of this mutant strain revealed that *M. grisea* contains a P-glycoprotein-encoding gene, hereinafter termed abc3, and that loss of function of this gene resulted in loss of pathogenicity.

With Agrobacterium T-DNA-mediated insertional mutagenesis, ABC3 function was identified as an essential factor in host penetration during *Magnaporthe* pathogenicity. Further characterization revealed that the ABC3 protein functions during the late appressorium stage and is required for successful entry of the fungus into host tissue. Therefore, loss of ABC3 protein results in cessation of infection-related morphogenesis which occurs during plant host penetration by the fungus. As a consequence, mutants lacking ABC3 were incapable of host penetration. The abc3 gene therefore is a new virulence determinant in *Magnaporthe.*

The role of ABC3 in *Magnaporthe* pathogenesis was confirmed by studies on TMT2807 and a *Magnaporthe* insertional mutant (abc3Δ) created in two separate wild type backgrounds which lack the P-glycoprotein-based efflux function. DNA fragments (about 1.1 kb each) representing the 5' and 3' UTR of ABC3 gene were obtained by PCR, ligated sequentially so as to flank the HPH1 cassette in pFGL44 to obtain plasmid vector pFGLabcKO. Linearized pFGLabcKO was introduced into wild-type *M. grisea* for a one-step replacement of the ABC3 gene with HPH1 cassette. The complete *M. grisea* ABC3 locus was obtained as a 6.3 kb HindIII fragment from the BAC 22C21 and cloned into the HindIII site of pFGL97 to obtain pFGLr2 with resistance to bialaphos or ammonium gluphosinate as a fungal selectable marker for the rescue transformation. See Example 1. Southern blots analyses were performed to confirm successful gene deletion strains and single-copy genomic integration of the ABC3 rescuing cassette. Flanking sequence analysis suggested that the insertion occurred in an as yet un-annotated region represented by Contig 2.904 from the *Magnaporthe* genome sequencing project. There also was a discrepancy in the neighboring contigs (contigs 2.903 and contig 2.902 do not exist). The disrupted gene locus of these mutants (abc3) encodes a protein with extensive homology to the Cluster II.2 (TC#3.A.1.201) type P-glycoprotein transporters such as human MDR1.

Annotation of the coding region confirmed this. A targeted gene deletion exercise for the complete open reading frame of the annotated gene (abc3) was performed to assess its role in *Magnaporthe* pathogenicity. Mycelia from the resulting mutant abc3Δ strain showed a slight reduction in vegetative growth on rich medium, although conidia formation remained unaffected. This suggested that ABC3 function is needed for maximal vegetative growth of *Magnaporthe*. Loss of ABC3 function, however, completely abolished appressorial function, which led to a complete cessation of host penetration. Complementation analysis using a full-length abc3 genomic clone rescued all the phenotypic defects associated with the loss of ABC3 function.

ABC3 protein showed extensive similarity to several MDR-like proteins from filamentous fungi, most notably *Phaeosphaeria, Fusarium, Neurospora* and *Aspergillus* species. Intragenome BLAST (*Magnaporthe* Genome Database, Broad Institute, USA) searches using ABC3 protein as the query revealed that *Magnaporthe* genome encodes at least 76

ABC-like transporters, and further identified a paralog (MG09931.4; 56% similarity) within the *Magnaporthe* proteome. Such paralogs also were uncovered in *Aspergillus, Fusarium* and *Neurospora* species. Their occurrence suggested a recent gene duplication event.

Phylogenetic analyses revealed that ABC3 protein most likely belongs to a distinct class of MDR transporters that is separate from those represented by Pmd1 and AtrC. ABC3 protein from *M. grisea* had extensive similarity to the mammalian (human) MDR/P-glycoprotein, HsMDR1, and to several MDR-like proteins from fungi and yeasts. It was most closely related to Fg6881, a hypothetical ORF from *Fusarium* spp.

ABC3 protein was able to functionally replace Pmd1 (its potential ortholog from the fission yeast) and, like Pmd1, regulated resistance towards cyclic peptide antibiotics such as Valinomycin. Compared to wild type fission yeast cells, however, the pmd1Δ mutant did not show any growth-related defects in contact with barley or rice leaf surfaces. Unlike the abc3-related Step 6 in budding yeast, Pmd1 is not required for mating. However, abc3 seems to have retained at least some important function in the mating pathway since loss of ABC3 led to a decrease in the overall number of perithecia. ABC3 protein, like its ortholog Step 6 from budding yeast, is required for fertility of the blast fungus. The closely related AfuMDR1 from *A. fumigatus* is specific for the antifungal agent Cilofungin, whereas AtrD, which is 76% identical to AfuMDR1, serves as an efflux pump for fenarimol. Thus the degree of primary sequence homology does not correlate strictly with similar substrate specificity.

The inability to recover viable cultures of the abc3Δ mutant from the inoculation sites in the host beyond 30 hours post infection also indicates that ABC3 protein is likely important for in planta survival and spread of *Magnaporthe*. In preliminary analyses the abc3Δ mutant's loss of viability appeared to be independent of the autophagic cell death pathway that has recently been implicated in conidial cell death during initiation of blast disease. Alternatively, it is possible that the increased cell death in the mutant is a consequence of excessive ROS accumulation.

The function of ABC3 protein in the regulation of oxidative stress is different from that found in its counterparts in fungus. The results presented here showed that loss of ABC3 protein renders the blast fungus more sensitive to oxidative damage. Compared to the wild type, abc3Δ mutant appressoria accumulate significantly higher levels of reactive oxygen intermediates. This peroxide accretion occurred under in vitro and in planta conditions. Suppressing this peroxide accumulation with exogenous antioxidants partially suppressed the host penetration defects in the abc3Δ mutant. Conversely, addition of exogenous peroxide, menadione or paraquat during infection assays significantly blocked the growth and function of wild type *Magnaporthe* conidia and appressoria. These data taken together indicate that the failure of abc3Δ appressoria to invade the host is caused by the cumulative effect of: (1) the accumulation of inhibitory metabolite(s) and (2) an excessive build-up of reactive oxygen intermediates. An observation of interest was the redox-sensitive regulation of ABC3 expression demonstrated using a GFP reporter construct. This suggests that ABC3 protein is a new MDR or P-glycoprotein that regulates fungal pathogenicity per se as well as the ability of the blast fungus to withstand host-specific environmental conditions.

*Magnaporthe* host plants are known to secrete a number of phytotoxins and other pathogenesis-related proteins upon fungal challenge. See, for example, Dixon et al., "Early events in the activation of plant defense responses" Annu. Rev. Phytopathol., 32:479-501, 1994; Osbourn, "Preformed Antimicrobial Compounds and Plant Defense against Fungal Attack" Plant Cell, 8:1821-1831, 1996; Kodama et al., "Sakuranetin, a flavonone phytoalexin from ultraviolet-irradiated rice leaves" Phytochemistry, 31:3807-3809, 1992. It is therefore likely that the abc3Δ mutant accumulates intracellularly toxic antifungal agent(s) of plant origin and that it is this which ultimately halts fungal growth and proliferation. The same would be true of any blast fungus that lacked sufficient ABC3 protein function, and therefore can serve as a point to combat blast disease. Alternatively, the abc3Δ mutant might be incapable of transporting as yet unidentified pathway intermediate(s) or host-specific toxic compound(s) that have deleterious effects within the fungal appressoria. The abc3Δ mutants lacking ABC3 protein function here failed to penetrate the host surface even upon extended incubation. Interestingly, these mutants were histologically similar to wild type when grown on artificial surfaces and were fully capable of invasive growth and spread in these surfaces. Thus, it appears likely that the ABC3 transporter is required for the efflux of one or more host-specific compounds during the penetration step.

Localization studies using an ABC3:GFP fusion protein showed that ABC3 is a plasma membrane resident protein in early appressoria and in penetration hyphae and thus would be accessible to peptide or similar antifungal agents in the external environment. Interestingly, ABC3 protein also localizes to the vacuolar lumen during the late appressorial stage, thus making it available to antifungal-agents accessible to the internal membrane compartments. Subsequently, the ABC3-GFP became plasma membrane-associated in primary penetration hyphae.

Thus, ABC3 is an important pathogenicity factor in *Magnaporthe* (and orthologs available in all pathogenic fungi sequenced thus far) that can be controlled using antifungal agents or inhibitors directed against it. Because ABC3 is a fungal-membrane resident pump involved in efflux of one or more toxic metabolites or inhibitors of appressoria function, deletion of this efflux function leads to hypersensitivity to hydrogen peroxide levels in the abc3Δ strain. This mechanism could play a role in regulation either of peroxide levels or intermediates derived from peroxide-related metabolism. The ABC3 protein also could function as a counter-defense mechanism in down-regulating the host response, based on the build-up of reactive oxygen species. Identifying molecules upstream and downstream of ABC3 and its potential substrates could lead to important molecular insights into the signaling mechanisms that are essential to host penetration by the fungus.

Inhibitors of ABC3 protein can be applied to plants or to the environment to impair or otherwise modify ABC3 function and block host penetration by the blast fungus and thus disease in the plant host. Such ABC3 inhibitors may include peptide or peptide-mimetic compounds, proteins or nucleic acids, for example a regulatory element, an antisense molecule or a replacement plasmid vector that knocks out the abc3 gene, which interfere with ABC3 function or expression. Peptide or protein inhibitors may be applied to the plant to be treated or protected. Small molecule (i.e. drug-like organic chemical molecules and the like as are known in the art) inhibitors of ABC3 protein function also are contemplated for use in methods of treating or preventing blast disease. Such small molecule inhibitors or peptide inhibitors may be identified according to conventional screening methods known in the art. Small molecule fungicides that specifically inhibit ABC3 function can be sprayed directly on the host plants to reduce fungal penetration and disease without the broad toxicity caused by traditional anti-fungal agents. Thus, an ABC3 inhibitor is any molecule which, when present in the plant, on the plant or in contact with the *Magnaporthe* pathogen.

Alternatively, host plants can be engineered to express protein or peptide ABC3 inhibitors, to create disease-resistant plants. The plant may be transformed with a gene such that the protein or peptide inhibitor is expressed in the plant or in appropriate tissues of the plant. Methods for producing transgenic plants of this type are known in the art, and any conventional methods are contemplated for use with this invention. Because other fungal species, including other pathogens, express related multi-drug resistance pumps, these methods would be useful in modifying the activity of ABC3 homologs in other fungal pathogens to reduce and control their ability to cause disease as well.

The fungal protein ABC3 therefore could be used in designing effective control agents against blast disease per se. For example, small molecule inhibitors or short peptides that block the function of ABC3 protein or perturb the requisite metabolic pathway(s) could be designed and such inhibitors would be, for example, spray inoculated or expressed in planta to prevent establishment and/or spread of disease. Such inhibiting agents also can be used on ABC3 orthologs in other pathogenic fungi to control the respective fungal diseases of plants and animals. Such orthologs include the abc3-encoding nucleic acids and ABC3 proteins of any plant pathogenic *Aspergillus, Ustilago* and *Fusarium* species as well as *Magnaporthe* species. These orthologs therefore are considered part of this invention, as well as methods using their analogous to those disclosed herein.

EXAMPLES

Example 1

Identification and Isolation of the ABC3 Locus

*Schizosaccharomyces pombe* wild-type strain YNB38 (h-, ade6-M216/leu1-32/ura4-D18/his3-D1) was maintained on yeast-extract plus supplements (YES) agar medium or under selection on Edinburgh minimal media (EMM), with appropriate supplements, using standard techniques as described in Moreno et al., "Molecular genetic analysis of fission yeast *Schizosaccharomyces pombe*" Meth. Enzymol., 194:795-823, 1991. Strains were grown on agar plates or in liquid media at 32° C.

Wild-type strains of *M. grisea*, Guy11 (mat1-2) and TH3 (mat1-1), were used in the following methods. Guy11, and the abc3Δ knockout and complementation strains were cultured on prune-agar medium or complete medium (CM) as described by Soundararajan et al., "Woronin body function in *Magnaporthe grisea* is essential for efficient pathogenesis and for survival during nitrogen starvation stress" Plant Cell, 16:1564-1574, 2004. Mycelia, collected from 2-day-old liquid CM-grown cultures were used to isolate nucleic acids. The *M. grisea* strains were cultured for a week on solid CM to assess the growth and colony characteristics unless indicated otherwise. Mycelia used for total protein extraction were obtained by growing the relevant strains in liquid CM for 3 days at 28° C. Mating analyses were performed as described by Valent et al., "*Magnaporthe grisea* genes for pathogenicity and virulence identified through a series of backcrosses" *Genetics* 127:87-101, 1991.

Conidia were obtained by scraping 8 day old cultures grown under constant illumination. Mycelial bits were separated from conidia by filtration through two layers of Miracloth™ (Calbiochem™, San Diego, Calif.) and resuspended to a concentration of $10^5$ spores per milliliter in sterile distilled water. For light microscopy, individual droplets (30 μl) of conidial suspensions were applied to plastic cover slips or other membranes and incubated under humid conditions at room temperature. Microscopic observations were made after 3, 6, 12, 24, and 36 hours.

cDNA synthesis and subsequent PCR amplification was conducted using Reverse Transcriptase, AMV and Taq DNA polymerase. For the 5' RACE, Terminal Deoxynucleotidyl Transferase Recombinant (Promega™) was used. The following primers were used for 5' RACE and 3' RACE: Abc-5' RACE 5'-CGGAACCAGATATGAGGAGCTGTTGA-3' (SEQ ID NO:3) and RACE-Oligo dT-anchor 5'-GACCACGCGTATCGATGTCGACTTTTTTTTTTTTTTTTC-3' (SEQ ID NO:4); RACE-anchor 5'-GACCACGCGTATCGATGTCGAC-3' (SEQ ID NO:5), and Abc-3' RACE 5'-TGATGCTGGTGTTGTACATG-3' (SEQ ID NO:6). For semi-quantitative RT-PCR experiments, the following primers were used: MgChap1F (CAAGCCGATAGACACACTGAC; SEQ ID NO:7) and MgChap1R (GAACTAATCGTCCTCAGTGC; SEQ ID NO:8) (this ORF is not annotated but maps to contigs 2.1212 and 2.1211); MgTubF (AAACAACTGGGCCAAGGGTCACTACA; SEQ ID NO:9) and MgTubR (CCGATGAAAGTCGACGACATCTTGAG; SEQ ID NO:10) corresponding to ORF MG00604.4; and Abc3F (CGTTATGCAGTCCATGTGGATGAGTC; SEQ ID NO:11) and Abc3R (ACGATTTGTTCGCTGCGCACGTCGAT; SEQ ID NO:12). The oligonucleotide primers for the RT-PCR experiments on hosts were: HvPr5F (CGCAGAGCAACAACAGTAAAGC; SEQ ID NO:13) and HvPr5R (ACGCCTATTATTGGTTGGCG; SEQ ID NO:14); and Hvact10F (CTGTCTTTCCCAGCATTGTA; SEQ ID NO:15) and Hvact10R (ATCCTCGGTGCGACACGGAG; SEQ ID NO:16).

For real-time PCR, total RNA was extracted from the requisite samples as described (Ramos-Pamplona and Naqvi, "Host invasion during rice-blast disease requires carnitine-dependent transport of peroxisomal acetyl-CoA" Mol. Microbiol. 61(1):61-75, 2006), treated with RNAase-free DNase (Roche Diagnostics™), and 1 μg was reverse-transcribed for 60 min at 42° C. using a Reverse Transcription Kit (Roche Diagnostics™) in the presence of random primers and oligo ($dT_{18}$). Quantitative PCR was performed by monitoring in real time the increase in fluorescence of the SYBR Green dye on an Applied Biosystems™ Real-Time PCR 7900HT instrument, according to the manufacturer's instructions. Primers used for the amplifications were Pr-1F (ATGGAGGTATCCAAGCTGGCCATT; SEQ ID NO:17); Pr-1R (GTAAGGCCTCTGTCCGACGAAGTT; SEQ ID NO:18); ActinF (TAGTATTGTTGGCCGTCCTCGCCACAC; SEQ ID NO:19); ActinR (GATGGAATGATGAAGCGCATATCCTTC; SEQ ID NO:20); HvPr5F (CGCAGAGCAACAACAGTAAAGC; SEQ ID NO:21); HvPr5R (ACGCCTATTATTGGTTGGCG; SEQ ID NO:22); Hvact10F (CTGTCTTTCCCAGCATTGTA; SEQ ID NO:23) and Hvact10R (ATCCTCGGTGCGACACGGAG; SEQ ID NO:24). Each RT-PCR quantification was carried out in triplicate. Melting curve analysis was applied to all final PCR products after the cycling protocols. Values for each gene were normalized to the expression level of the respective control condition and used further to calculate the ratio of the expression levels of the requisite transcripts (for example, Pr-1/Actin).

Protein purification and immunoblotting procedures were performed as described by Soundararajan et al., "Woronin body function in *Magnaporthe grisea* is essential for efficient pathogenesis and for survival during nitrogen starvation stress." Plant Cell, 16:1564-1574, 2004. Protein concentrations were determined according to the Bradford method using a commercial kit (Bio-Rad Laboratories™). The enhanced chemiluminescent method (ECL kit; Amersham Biosciences™) was used for Southern and western blot analysis.

Multiple sequence alignments were initially performed using ClustalW (Thompson et al., 1994) for the following MDR sequences related to Abc3 protein: *Mus* (ABCB1, NP_035206), *Rattus* (ABCB1a, NP_596892), *Cricetulus* (ABCB1, P21448), *Homo* (ABCB1, AAW82430), *Canis* (MDR1, AAY67840), *Ovis* (MDR1, NP_001009790), *Xenopus* (MDR11, NP_989254), *Gallus* (LOC420606, XP_418707), *Oryza* (XP_467259), *Chaetomium* (CHGG_08744; EAQ84730), *Neurospora* (re-annotated NCU06011.2 and NCU9975.1), *Magnaporthe* (ABC3, AAZ81480 and MG09931.4), *Fusarium* (FG06881.1; FG03323.1; FG08823.1; FG02786.1; FG01684.1), *Aspergillus* (AAD43626; Afu7g00480; AN9342.2; AN2349.2; XP_747768; BAE64667; BAE61398; AAD25925; AAB88658; AN3608.2; XP 751944), *Coccidioides* (EAS34680; EAS30718; EAS35426), *Saccharomyces* (STE6; CAA82054); *Schizosaccharomyces* (MAM1, P78966; PMD1, CAA20363); *Ustilago* (UM06009.1), *Cryptococcus* (CNA07730), *Filobasidiella* (MDR1, AAC49890), *Yarrowia* (YAL1OB12188g), *Leptosphaeria* (AAS92552), *Venturia* (AAL57243), *Trichophyton* (AAG01549) and *Phaeosphaeria* (EAT87032).

Figure 1:
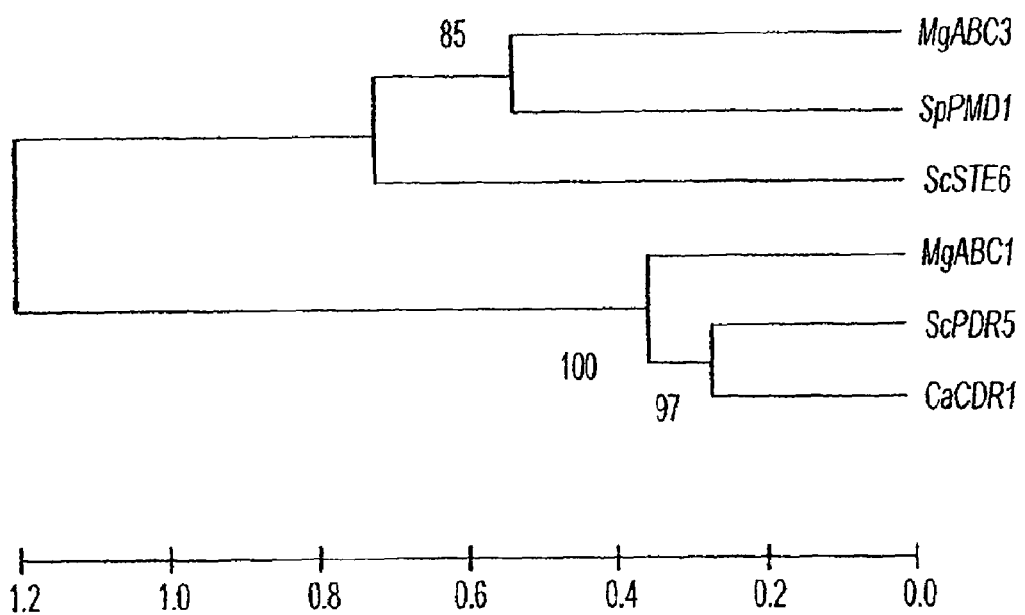

Phylip 3.6a (Felsenstein, "PHYLIP (phylogeny inference package). Version 3.2." Cladistics, 5:164-166, 1989) was subsequently used, after removing the gaps from the initial alignment, to create a phylogram representing the most parsimonious phylogenetic relatedness of *Magnaporthe* Abc3p with the other MDR sequences from the indicated genera within the eukaryotes. Bootstrap analysis (500 replicates/iterations) was used to generate the phylogenetic tree using the Neighbor-joining algorithm in Phylip 3.6a. Percent bootstrap support values exceeding 50% were considered significant. The MDR hits related to ABC3 protein were identified initially using the B-Link webtool on the NCBI network. See FIG. 1.

Figure 2:
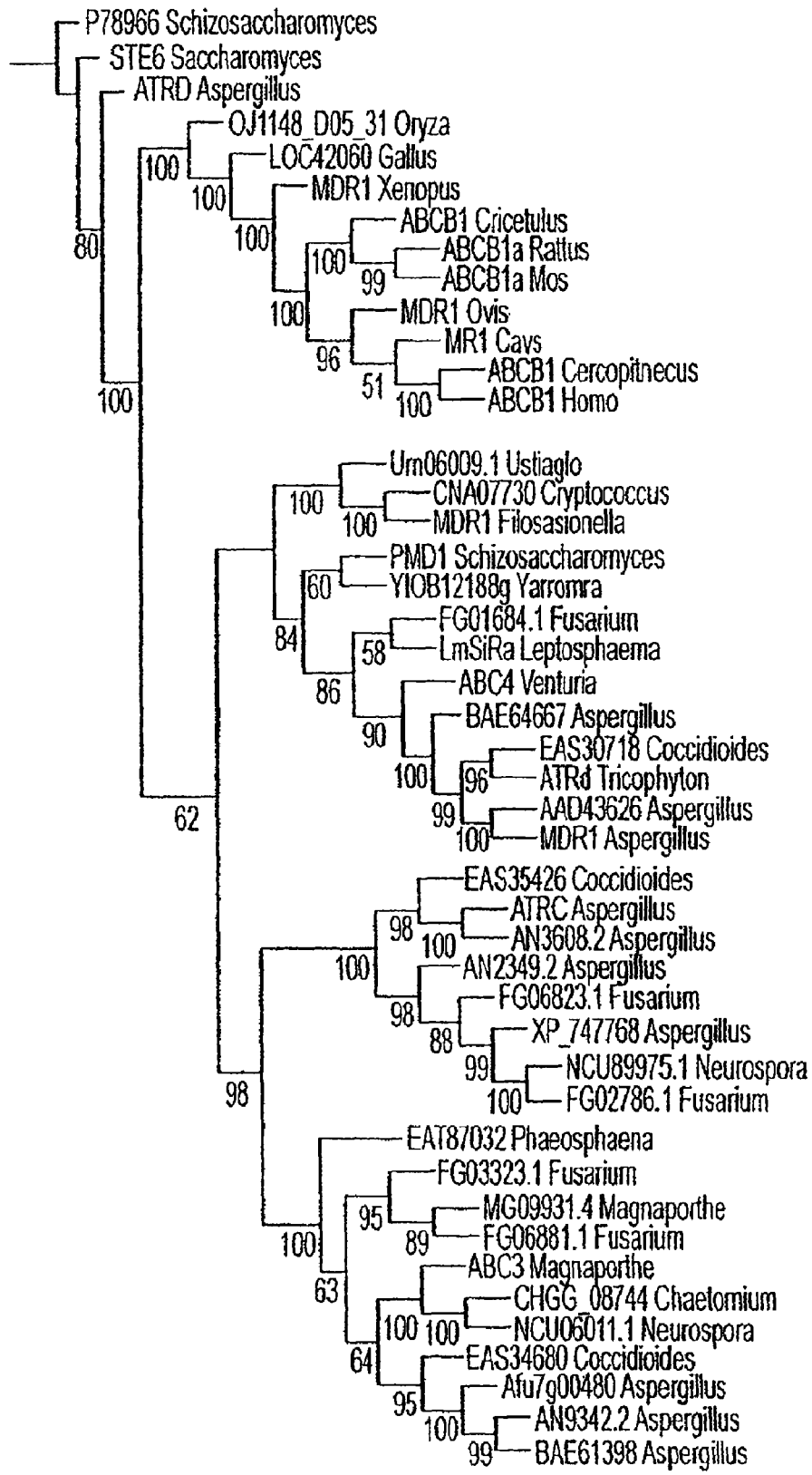

FIG. 2 is a ClustalW diagram (Thompson et al., "CLUSTAL W: improving the sensitivity of progressive multiple sequence alignment through sequence weighting, positions-specific gap penalties and weight matrix choice" Nucl. Acids Res., 22:4673-4680, 1994) and Phylip 3.6a-assisted dendrogram (Felsenstein, "PHYLIP (phylogeny inference package). Version 3.2" Cladistics, 5:164-166, 1989) depicting the most parsimonious phylogenetic relatedness of *Magnaporthe* ABC3 protein with the MDR proteins from the indicated genera within eukaryotes. Bootstrapping (500 replicates/iterations) was used to generate the phylogenetic tree using the Neighbor-joining algorithm in Phylip 3.6a. Percent bootstrap support for each clade (when >50%) is indicated below the branch. B-Link webtool on the NCBI network was initially used to select 44 MDR hits related to ABC3 protein.

Comparison of the ABC3 protein sequence with related sequences in SWISS-PROT and other protein sequence resources identified several members of the P-glycoprotein family of ABC transporters. See FIG. 3. The phylogenetic relationship was established using these sequences (FIG. 2). Individual sequence comparisons and phylogenetic analyses based on CLUSTAL W (FIG. 1), MEGA (Kumar et al., "MEGA 3: integrated software for molecular evolutionary genetics analysis and sequence alignment" Briefings in Bioinformatics, 5:150-163, 2004) and Phylip 3.6a revealed that ABC3 protein likely defines a separate family of fungal MDR transporters distinct from the Pmd1 or the ATRC family (see FIG. 2, arrowheads). This phylogram also showed that ABC3 protein had diverged significantly from its most related Step 6 protein in *Saccharomyces*. There was however a paralogous transporter (MG09931.4; 56% similarity) encoded in *Magnaporthe*.

In the Clustal W-based amino acid sequence alignment of yeast sequences (FIG. 3), neither ABC3 protein nor MG09931.4 showed any significant similarity (average 7% similarity and 4% identity) to the ABC1 (Urban et al., 1999) or ABC3 transporter (Lee et al., 2005) reported in *Magnaporthe*. ABC3 showed the highest similarity to SNOG_05968 from *Phaeosphaeria* (62% similarity and 43% identity) and was found to be closely related to AtrC from *A. nidulans* (34% identity and 53% similarity), the fission yeast Pmd1 (35% identity and 54% similarity; Nishi et al., "A leptomycin B resistance gene of *Schizosaccharomyces pombe* encodes a protein similar to the mammalian P-glycoproteins" Mol. Microbiol. 6:761-769, 1992), and the budding yeast Step 6 (*Saccharomyces ceriviseae*) (28% identity and 46% similarity; Ketchum et al., "The yeast a-factor transporter Stelop, a member of the ABC superfamily, couples ATP hydrolysis to pheromone expert" J. Biol. Chem., 27: 29007-29001, 2001), whereas ABC1 (*M. grisea*) showed a higher level of similarity to the ScPdr5 (*S. ceriviseae*) and CaCDR1 (*Candida albicans*) transporters from yeasts. See FIG. 3.

*Agrobacterium tumefaciens* T-DNA-transfer was performed in *M. grisea* using hygromycin resistance (encoded by hygromycin phosphotransferase gene HPH) as a selectable marker. Copy number of the integron was identified by Southern blots using standard procedures as described in Sambrook et al., "Molecular Cloning: A Laboratory Manual" Cold Spring Harbor, N.Y.: Cold Spring Harbor Laboratory Press, 1989. Mutant strains of interest were collected and purified by backcross analysis, progeny testing, random ascospore analysis and by monoconidial isolation. These strategies have been described in detail in the art and were performed as described by Soundararajan et al., "Woronin body function in *Magnaporthe grisea* is essential for efficient pathogenesis and for survival during nitrogen starvation stress" Plant Cell, 16:1564-1574, 2004.

TMT2807 was obtained in the above screen as a single-copy insertional mutant that produced slightly larger appressoria and showed total loss of pathogenicity towards barley explants. DNA sequences flanking the right and left border of the T-DNA insertion in TMT2807 were amplified using the standard TAIL PCR method (Liu et al., "Efficient isolation and mapping of *Arabidopsis thaliana* T-DNA insert junctions by thermal asymmetric interlaced PCR" Plant J., 8:457-463, 1995) and subsequently confirmed by nucleotide sequencing. A mutant strain carrying the same disruption of ABC3 as confirmed in TMT2807 was created in a Guy11 background and characterized in parallel.

Figure 4A:
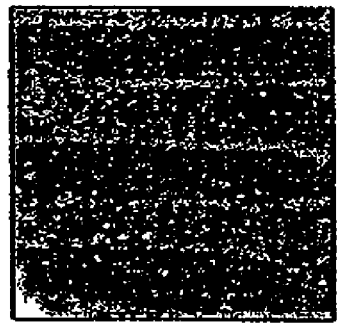
Figure 4B:
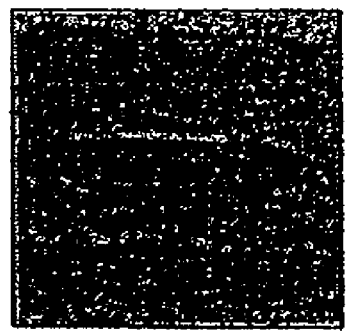
Figure 5A:
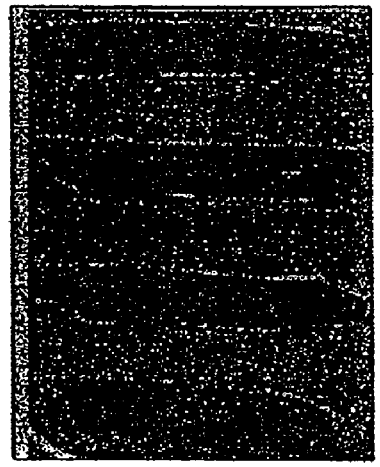
Figure 5B:

The mutant strain (TMT2807) of *M. grisea* (wild-type strain Guy11) was identified by its dramatic and complete inability to infect the barley cultivar Express™ in an Agrobacterium Transfer-DNA based random insertional mutagenesis screen for non-pathogenic mutants of *Magnaporthe*. See FIGS. 4 and 5, which show barley leaf explants inoculated with conidiospores of TMT2807 or wild type (WT) strain. The leaf tissue was assessed for disease symptoms after 9 days. Further monoconidial and random ascospore-analysis-assisted purification of this strain showed that loss of the pathogenesis ability co-segregated with hygromycin resistance, which was conferred by the single copy integration of the HPH1-containing transfer DNA in this strain.

Standard molecular manipulations were performed according to standard methods. See Sambrook et al., "Molecular Cloning: A Laboratory Manual" Cold Spring Harbor, N.Y.: Cold Spring Harbor Laboratory Press, 1989. Fungal genomic DNA was extracted with the potassium acetate method as described by Naqvi et al., "Identification of RAPD markers linked to a major gene for blast resistance in rice" Mol. Breed., 1:341-348, 1995. Plasmid DNA was isolated using Qiagen™ plasmid preparation kits. Nucleotide sequencing was performed using the ABI Prism big dye terminator method. Homology searches of DNA/protein sequences were performed using the BLAST™ program according to the methods described by Altschul et al., "Gapped BLAST and PSI-BLAST: A new generation of protein database search programs" Nucleic Acids Res. 25:3389-3402, 1997. GeneWise™-based predictions were made using the public domain database of the European Bioinformatics Institute. Total RNA was isolated with the RNeasy™ Plant Mini kit (Qiagen™) and cDNA synthesis and subsequent PCR amplification was conducted using Reverse Transcriptase, AMV (Roche Diagnostics™, and Taq DNA Polymerase (Roche™).

Thermal asymmetric interlaced (TAIL) PCR-based sequence analysis (Liu et al., "Efficient isolation and mapping of *Arabidopsis thaliana* T-DNA insert junctions by thermal asymmetric interlaced PCR" Plant J. 8:457-463, 1995) revealed that the T-DNA insertion in TMT2807 had disrupted the genomic region corresponding to Contig 67 on Supercontig 5.117 (*Magnaporthe* Genome Database, Release 5, Broad Institute, USA). Further subcloning and sequence analysis showed that the T-DNA insertion in TMT2807 disrupted a region just proximal (231 bp upstream) to exon1 of open reading frame MGG_13762.5 (FIG. 6) and led to a total loss of transcription of this ORF. Analysis of a BAC clone 22C21 (identified by using the T-DNA insertion flanks from TMT2807 as probes) revealed the presence of the ORF mentioned above as a 6.3 kilo-basepair (kb) HindIII fragment. See FIG. 6. This gene was designated abc3 because its predicted product showed high degree of sequence similarity to the ATP-binding cassettes (ABC) encoded by the genes belonging to the ABC transporter superfamily.

Figure 6:
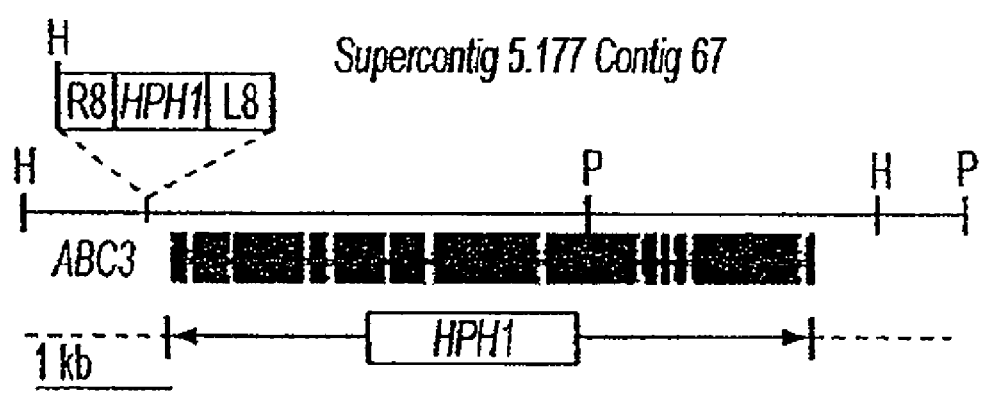

FIG. 6 is a schematic representation of the annotated abc3 locus spanning a HindIII-PvuII fragment from Contig 67 on Supercontig 5.117 in *M. grisea*. Solid bars and short open boxes indicate the coding regions and introns respectively and are drawn to scale. RB and LB represent the right and left border sequences of T-DNA (open box) integrated in the mutant strain. Opposing arrows demarcate the genomic region deleted in the abc3Δ strain, that was created using flanking homology (dashed lines) based gene replacement with the hygromycin-resistance cassette (HPH1). Restriction enzyme sites HindIII (H) and PvuII (P) have been depicted. The scale bar corresponds to 1 kb and also denotes the probe used for Southern analysis shown in FIG. 7.

Genomic DNA from wild-type (WT), abc3Δ, Complemented strain (Comp; abc3Δ carrying an ectopic single-copy integration of the HindIII fragment described above) and TMT2807 strain was digested with HindIII and probed with the 1 kb ABC3 fragment or the HPH1-specific fragment. See FIG. 7. The appearance of the 3.2 kb band in the abc3Δ strain, with the concomitant loss of the wild-type 6.3 kb ABC3 locus, was diagnostic of the correct gene replacement event. Ectopic integration of the rescue construct in the complemented strain resulted in the retention of the 3.2 kb fragment and the restoration of the 6.3 kb band. The presence of a 0.6 kb fragment in the TMT2807 strain was due to an internal HindIII site at the right-border end of the integrated T-DNA in TMT2807. This integron also accounts for the ~7 kb fragment (the abc3 gene disrupted with the HPH1 T-DNA cassette) detected in this mutant. A DNA gel blot with HPH1 as the probe further confirmed the identity of the fragments. Molecular size markers in kilo-basepair are indicated. See FIG. 7.

A full-length abc3 cDNA was obtained by 3' and 5' rapid amplification of the cDNA ends (RACE). The abc3 locus spanned nucleotides 124832 to 131097 on Supercontig 177. The abc3 cDNA sequence was confirmed by obtaining and sequencing several RT-PCR fragments representing the overall abc3 coding sequence. In each instance, DNA sequence analysis was carried out on both strands of at least 2 individual clones. Subsequent analysis revealed the existence of 13 exons in the abc3 open reading frame as opposed to the autocall-predicted eleven exons in MGG_13762.5. In addition, 3 nucleotide changes were uncovered in exon 3 of MGG_13762.5. Typical regulatory elements related to fungal promoter regions preceded the abc3 open reading frame. Based on the cDNA sequence, the abc3 gene was predicted to encode a 1321 amino-acid protein (ABC3) composed of two homologous halves, each with six membrane-spanning segments (ABC transmembrane domain) and an ABC ATPase motif. ABC3 protein thus showed an overall structure and domain organization typical of the Cluster II.2 (or TC#3.A.1.201) type P-glycoprotein MDR transporters (Decottignies and Goffeau, "Complete inventory of the yeast ABC proteins" Nat. Genet., 15:137-145, 1997; Saier and Paulsen, "Phylogeny of multidrug transporters" Semin. Cell Dev. Biol., 12:205-213, 2001).

The complete nucleotide sequence and annotation details for abc3 have been deposited in GenBank under accession number DQ156556 the disclosures of which are hereby incorporated by reference. The sequence of an abc3 coding region is provided as SEQ ID NO:1 (FIG. 8) and an ABC3 protein as SEQ ID NO:2 (FIG. 9). See Table I, below, for the final annotation of the protein, based on the abc3 Rescue HinDIII fragment and cDNA. Nucleic acids which encode the protein of SEQ ID NO:2 also form part of the present invention, as well as any nucleic acid which encodes a protein having substantially the same activity of SEQ ID NO:2. An ABC3 protein includes any protein which is native to a *Magnaporthe* species, is at least 95% homologous to SEQ ID NO:2, and which, if not present or not active, results in loss or substantial reduction (>90%) of appressorial function and plant pathogenicity. An abc3 gene a used herein is a nucleic acid that encodes an ABC3 protein.

TABLE I

Final Annotation of ABC3.

| | From | To | Length (bp) |
|---|---|---|---|
| Exon 1 | 1040 | 1120 | 81 |
| Intron 1 | 1121 | 1173 | 53 |
| Exon 2 | 1174 | 1422 | 249 |
| Intron 2 | 1423 | 1469 | 47 |
| Exon 3 | 1470 | 1974 | 505 |
| Intron 3 | 1975 | 2022 | 48 |
| Exon 4 | 2023 | 2119 | 97 |
| Intron 4 | 2120 | 2166 | 47 |
| Exon 5 | 2167 | 2530 | 364 |
| Intron 5 | 2530 | 2575 | 45 |
| Exon 6 | 2576 | 2830 | 255 |
| Intron 6 | 2831 | 2882 | 52 |
| Exon 7 | 2883 | 3612 | 730 |
| Intron 7 | 3613 | 3662 | 50 |
| Exon 8 | 3663 | 4365 | 703 |
| Intron 8 | 4366 | 4415 | 50 |
| Exon 9 | 4416 | 4465 | 50 |

TABLE I-continued

Final Annotation of ABC3.

| | From | To | Length (bp) |
|---|---|---|---|
| Intron 9 | 4466 | 4514 | 49 |
| Exon 10 | 4515 | 4540 | 26 |
| Intron 10 | 4541 | 4591 | 51 |
| Exon 11 | 4592 | 4631 | 40 |
| Intron 11 | 4632 | 4682 | 51 |
| Exon 12 | 4683 | 5521 | 839 |
| Intron 12 | 5522 | 5577 | 56 |
| Exon 13 | 5578 | 5603 | 27 |

Example 2

Deletion of the ABC3 Open Reading Frame

One-step PCR-based gene deletion (using the Ura4+ marker) was performed according to the methods of Bahler et al., "Heterologous modules for efficient and versatile PCR-based gene targeting in Schizosaccharomyces pombe" Yeast 14:943-951, 1998, using 80 bp flanking sequence homology. Deletion of the pmd1 open reading frame was carried out in the YNB38 strain. Stable transformants from EMM minus Uracil medium were tested by colony PCR. The M. grisea abc3 locus was obtained as a 6.3 Kb HinDIII fragment from BAC 22C21 and cloned into the unique HinDIII site in pJK148 to obtain pFGLr1, carrying the Leu1+ marker. Vector pFGLr1 was linearized with EcoRI and transformed by electroporation into the S. pombe pmd1 deletion strain described above. Stable integration of FGLr1 was confirmed by PCR analysis and copy number ascertained by Southern blot analysis.

Figure 7A:
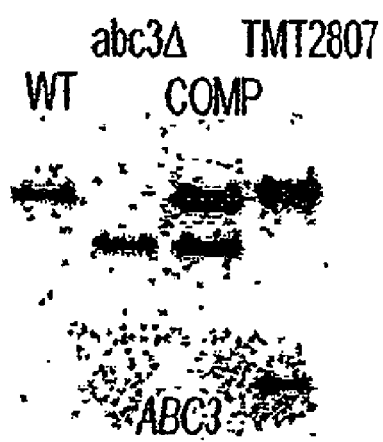
Figure 7B:
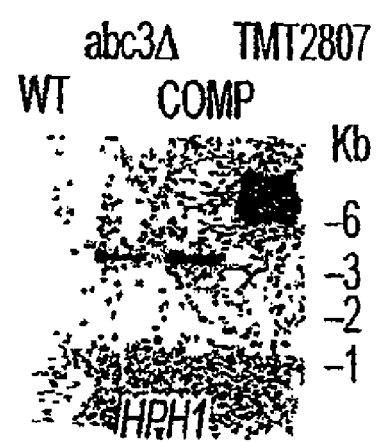

Using plasmid vector pFGLabcKO in a one-step gene replacement technique, an abc3 deletion mutant (hereafter referred as abc3Δ) was created by replacing the entire 4.61 kb coding region of the abc3 locus with the HPH1 cassette encoding the hygromycin phosphotransferase function. Hygromycin-resistant transformants (HPH1$^+$) derived from the wild type Guy11 strain, carrying single-copy insertion of the replacement cassette, were identified and the desired gene replacement event (abc3::HPH1) confirmed by Southern blotting (FIG. 7). For complementation analysis, a full-length genomic copy of abc3 (FIG. 6; 6.3 kb HindIII fragment) was introduced into the abc3Δ strain as a single ectopic integron. At least two independent strains from each background were examined to assess all the vegetative, reproductive and pathogenesis related defects reported here.

Example 3

Phenotypic Characterization of abc3Δ Strains pFGLr2 (carrying the full-length abc3 gene) or pBarKS (control) was introduced into the abc3Δ strain and the TMT2807 mutant. About 20 bialaphos-resistant transformants were screened by DNA gel blot analysis in each instance. Two strains that carried single-copy integration of the abc3 gene at an ectopic site in each background (TMT2807 and abc3Δ) were used for further tests.

For abc3 gene deletion and rescue of the abc3Δ mutant, DNA fragments about 1.1 kb each, representing the 5' and 3' UTR of abc3 gene, were obtained by PCR. The fragments were ligated sequentially so as to flank the hph cassette in pFGL44 to obtain plasmid vector pFGLabcKO. pFGLabcKO was transformed into M. grisea for replacement of the abc3 gene. The complete M. grisea abc3 locus was obtained as a 6.2 Kb HinDIII fragment from the BAC 22C21 and cloned into the HinDIII site of pFGL97 to obtain pFGLr2 with resistance to bialaphos or ammonium gluphosinate as a fungal selectable marker for the rescue transformation. Southern blot analyses were performed to confirm successful gene deletion strains and single-copy genomic integration of the abc3 rescuing cassette.

Wild-type, abc3Δ mutant and an abc3Δ strain complemented with full length ABC3 (Comp) (mycelial plugs or conidial suspension) were grown on complete agar medium for a week and photographed. See FIG. 10. The growth characteristics are representative of three independent assessments (total n=27 colonies per strain; P<0.05). When inoculated as mycelial plugs or as a conidial suspension on solidified complete medium (CM), the abc3Δ mutant grew slower (~30% reduction in colony size, P<0.05) than the wild type Guy11 (FIG. 10), although no apparent difference in conidiogenesis or the overall colony morphology was uncovered. Quantitation of data from the material in FIG. 10 is provided graphically in FIG. 11.

Figure 10:
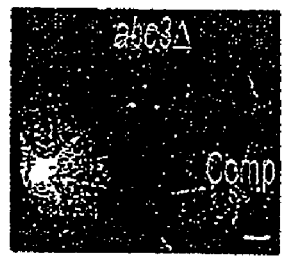
Figure 11:
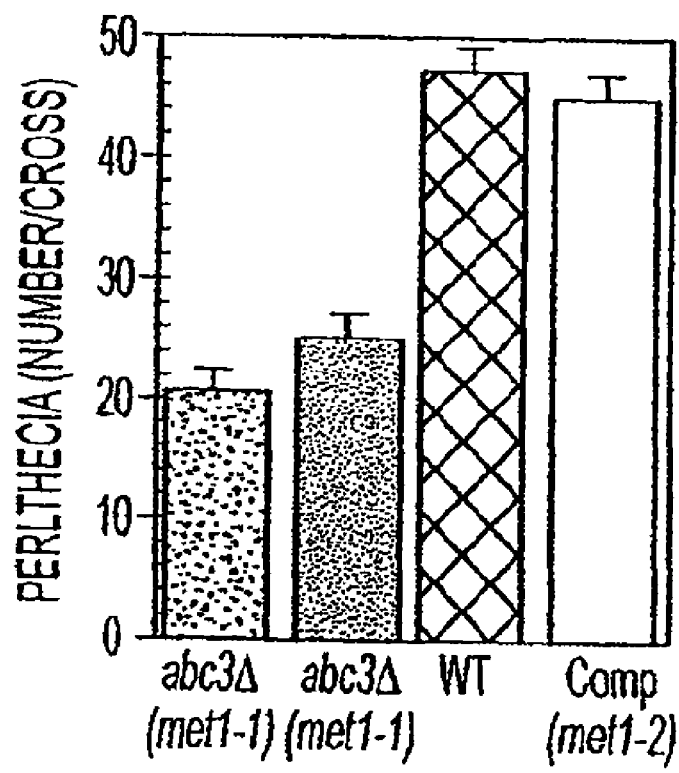

FIGS. 10 and 11 show growth characteristics and mating in abc3Δ mutant, photographically and quantitatively. Perithecia development by the indicated Magnaporthe strains in individual sexual crosses with the tester strain of the opposite mating type, were assessed 3 weeks post inoculation. Mean values (±SD) represent the number of perithecial beaks observed per mating mix on oatmeal agar medium. Quantitations represent three independent experiments covering a total of 30 crosses per strain. WT refers to the cross between Guy11 (mat1-2) and TH3 (mat1-1). When crossed to TH3 (mat1-1), the abc3Δ (mat1-2) mutant showed a slight reduction in its sexual reproduction, displaying a decrease in the total number of perithecia produced per sexual cross. See FIG. 11.

There were no significant difference in conidiation of these moderately stunted abc3Δ mutant colonies as compared to Guy11. Conidia germination and appressoria formation were not observably different from wild type in the abc3Δ strain. Such defects were not mating-type specific as judged by analyzing the sexual crosses between an abc3Δ (mat1-1) and wild type Guy11 (mat1-2) (FIG. 11) and could be attributed to reduced female fertility in the Magnaporthe strains used (Valent et al., "Magnaporthe grisea genes for pathogenicity and virulence identified through a series of backcrosses" Genetics, 127:87-101, 1991). The complemented abc3Δ strain behaved like the wild type in the ability to form perithecia. This suggested a divergence of function for ABC3 protein compared to the related Step 6 protein, which is required specifically for the efflux of only the a-factor pheromone in Saccharomyces. These results indicated that in Magnaporthe, the ABC3 function is required for proper vegetative growth of the mycelia, but is dispensable for sexual reproduction.

Figure 12A:
Figure 12B:
Figure 13A:
Figure 13B:
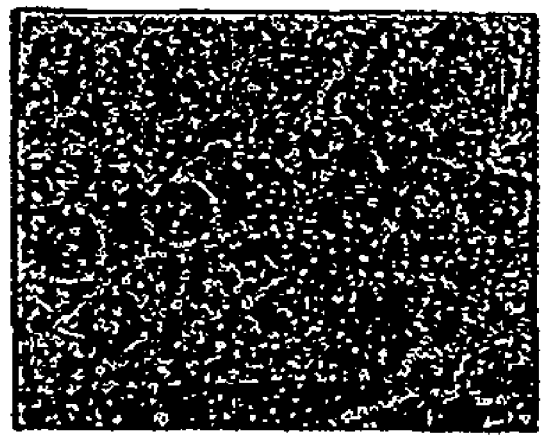

The germination efficiency and growth of the abc3Δ conidia were assessed. Conidia produced by the abc3Δ strain were normal in quantity, morphology and germination compared to wild type conidia. See FIG. 12. FIG. 13 shows that upon germination, the abc3Δ conidia produced appressoria (average diameter 11.2±0.7 μm; n=3000; P<0.05) that were marginally larger than those of the wild type strain (10.4±0.6 μm; n=3000; P<0.05).

Example 4

The Role of ABC3 in Magnaporthe Pathogenesis

To assess the role of ABC3 protein during host-associated growth and development, infection assays were performed on the seedlings of rice cultivars CO39 or NIL127 and barley cultivar Express™, testing the pathogenicity of abc3Δ conidia. Blast infection assays on host tissue were conducted as follows. Rice seedlings belonging to CO39 (compatible) or NIL127 (incompatible) genotypes were spray-inoculated with conidial suspensions (in 0.02% gelatin in water) from wild-type, abc3Δ or abc3Δ mutant strains complemented by the introduction of ABC3 (COMP). Disease symptoms were assessed after 10 days.

Figure 14:
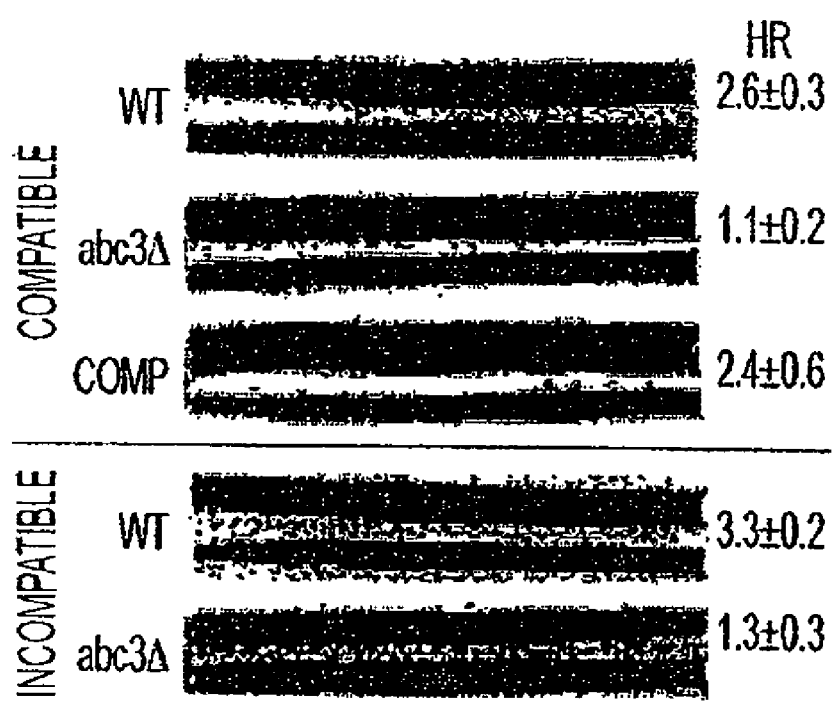

The abc3Δ mutant (like the TMT2807 strain), displayed a total loss of pathogenicity and failed to elicit any visible blast symptoms/lesions on the compatible (CO39) or incompatible (NIL127) rice varieties, when compared with equivalent spray-inoculations of the wild type Guy11 conidia or the conidia from the Complemented strain. See FIG. 14. Under the same conditions, the wild type and the Complemented strain (COMP) caused typical spindle-like, gray centered and severe blast lesions that merged into one another on the inoculated rice leaves (FIG. 14).

Twenty bialaphos-resistant abc3Δ strain and TMT2807 mutant transformants were produced. The transformants contained pFGLr2 (carrying the full-length ABC3 gene) or pBarKS (control) then were screened by DNA gel blot analysis. Two strains that carried single-copy integration of the abc3 gene at an ectopic site in each background (TMT2807 and abc3Δ) were used to analyze the suppression of the various phenotypic defects observed in the abc3Δ mutant. The mild reduction in vegetative growth and mating efficiency observed in the abc3Δ strain (and in TMT2807) was completely suppressed upon introduction of the wild type ABC3 gene. See FIG. 14, COMP].

Introduction of the ABC3 gene also restored the strain's ability to penetrate the host and cause blast disease. See FIG. 14, COMP. This complemented (COMP) strain was found to be as virulent as the wild type isolate, when spray-inoculated on rice seedlings. In contrast, the vector control could not suppress these abnormalities (data not shown). Since all the defects in the abc3Δ mutant (and TMT2807) could be completely restored by reintroduction of the wild type ABC3 allele, we conclude that the phenotypic changes and functional abnormalities observed in the abc3Δ strain resulted solely from the disruption of ABC3 function.

The host-defense associated Hypersensitive Reaction (HR) was quantitated in the challenged seedlings based on real time RT-PCR methodology to derive the ratio of rice Pr-1 to Actin gene expression as described by Gilbert et al., "A P-type ATPase required for rice blast disease and induction of host resistance" Nature, 440:535-539, 2006. The values given in FIG. 14 are hypersensitive-reaction (HR) assessed after 48 hours and represent the ratio of rice Pr-1 gene expression to that of the Actin transcript. As shown in FIG. 14, the abc3Δ mutant failed to elicit proper HR during a compatible or incompatible interaction with the host.

Barley-leaf explants challenged with wild type or abc3Δ mutant for 72 hours, were co-stained with 3,3'-diaminobenzidine and Trypan blue in order to visualize the hypersensitivity reaction symptoms in the challenged tissue. Wild type strain caused massive damage and cell death and accumulation of reactive oxygen intermediates in the host leaves, whereas the abc3Δ mutant failed to elicit any visible hypersensitivity reaction symptoms in the host and was devoid of such cell death and accumulation of reactive oxygen species, except in rare instances (<1%). See FIG. 15 (the arrowhead indicates a rare hypersensitivity reaction event in the host upon challenge with the mutant).

In order to further confirm the failure to elicit hypersensitivity reaction, induction of Pathogenesis-related protein 5 (Pr-5, Genbank Accession HVU276225) in barley leaves challenged for 48 hours was tested. The ratio of Pr-5 expression to that of a gene with a house-keeping function (Actin10-4, Genbank accession HVU21907) was used to estimate the level of hypersensitivity reaction induction. In mock inoculations and in barley leaves challenged with the abc3Δ mutant, this ratio (Pr-5/HvAct10) averaged 1.4±0.3 over three replicates (P<0.05), whereas the ratio was consistently higher and averaged 2.6±0.5 (P<0.005) when estimated in plants infected by the wild type strain. The abc3Δ mutant could still be recovered as viable colony forming units from the challenged leaves but only up to 30 hours post inoculation. The above plant infection data indicates that ABC3 protein is required for *Magnaporthe* pathogenicity. Upon loss of ABC3 function, the blast fungus is incapable of establishing disease and eventually fails to survive inside the host.

Figure 16:
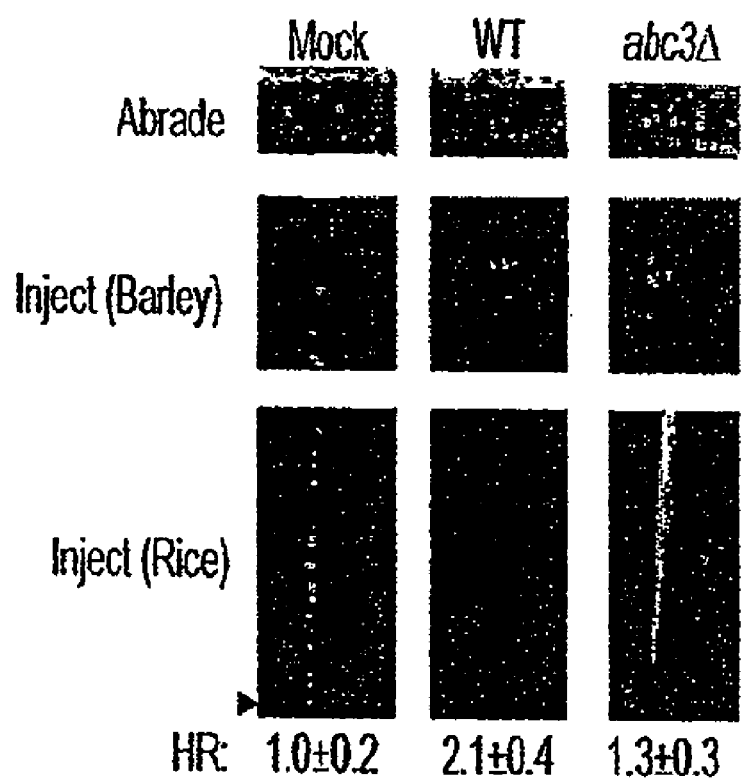

Since concentrated suspensions of abc3Δ conidia failed to elicit any host lesions after surface inoculation, these conidia were subjected to two additional tests: (1) inoculation on abraded host leaves and (2) direct injection of conidia into the leaf nodes or rice leaf sheaths. Equal numbers of conidia from the wild-type or abc3Δ mutant were inoculated either on abraded barley leaves (FIG. 16, upper panels) or injected at the base of barley leaves (FIG. 16, central panels) or the base of rice-leaf sheaths (FIG. 16, bottom panels). Host damage and disease lesion formation were subsequently assessed after 10 days. Hypersensitivity reaction was assessed after 48 hours as described above. Mock refers to the same inoculation treatments but using a 0.02% gelatin solution devoid of conidiospores.

Figure 15:
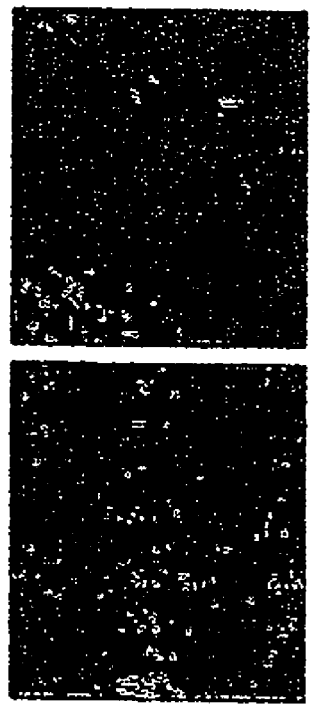

These assays showed that abc3Δ mutant is incapable of causing disease-related host damage even when forcibly introduced through wounded tissue or injected directly into the host plants (FIG. 15). Appropriate positive and negative controls were included and are shown alongside in these assays. Even under conditions that bypass the requirement of appressorium function, the abc3Δ mutant failed to elicit proper hypersensitivity reaction as determined by the ratio of Pr-1/Actin gene expression (FIG. 15).

Example 5

Appressorium Function and Host Penetration Defects in the abc3Δ Strain

Figure 17:
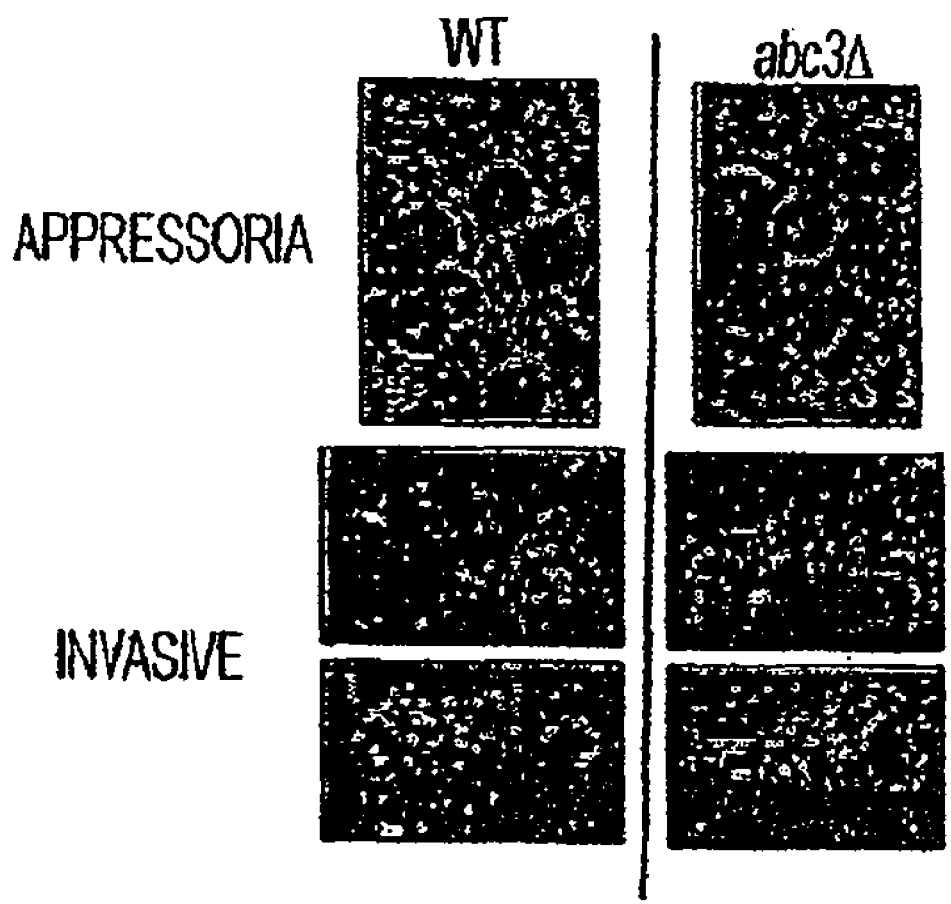

Equivalent numbers of conidia from the wild type or abc3Δ mutant were inoculated onto synthetic membranes (PUDO-193 cellophane) and assessed for germination, appressoria formation, surface penetration and invasive growth. The mutant appressoria were functional on PUDO-193 cellophane (clergeot et al., "PLS1, a gene encoding a tetraspanin-like protein, is required for penetration of rice leaf by the fungal pathogen *Magnaporthe grisel*," Proc. Natl. Acad. Sci. USA, 98:6963-6968, 2001) and penetrated it (FIG. 17 lower panels, see arrowheads) albeit with a much lower efficiency (39±2.5% compared to 58±2.1%; P<0.005) than the wild type appressoria. Invasive growth within the cellophane appeared to be compromised in the abc3Δ strain. Taken together, these data indicate that the abc3Δ mutant is incapable of eliciting proper hypersensitivity reaction or causing blast disease in the host plants, but although inefficiently, is still capable of breaching and invading cellophane membranes.

To address the question whether the ability to breach the artificial membranes, but not the host tissue, was due to a decrease in appressorial turgor in the abc3Δ strain, cytorrhysis assays were performed according to published methods to estimate the appressorial turgor through the incipient. See Howard et al., "Penetration of hard substrates by a fungus employing enormous turgor pressures." Proc. Natl. Acad. Sci. USA, 88:11281-11284 1991; de Jong et al., "Glycerol generates turgor in rice blast." Nature, 389:244-245 1997). Briefly, the appressoria were allowed to form for 45 hours on GelBond™ membrane prior to the addition of the indicated concentration of external glycerol. These appressorial collapse assays revealed that compared to the wild-type, the abc3Δ mutant displayed a slightly lower appressorial turgor which was not statistically significant. See Table II, below. This reduction in turgor in the mutant appressoria was particularly evident when the external glycerol addition was in the 3.5 to 4.5 molar range. At lower molar concentrations (1-3 M), the internal turgor levels were inferred to be equivalent to those estimated in the wild type appressoria. As judged by light microscopy and by thin-section transmission electron microscopy, melanin deposition appeared similar to wild type in the abc3Δ appressoria.

TABLE II

Appressorial cytorrhysis assay in wild-type Guy11 and the abc3Δ mutant.

| External Glycerol (Molar concentration) | Guy11 % cytorrhysis* | abc3Δ % cytorrhysis* |
|---|---|---|
| 1.0 | 5.0 ± 1.1 | 6.2 ± 1.5 |
| 2.0 | 8.2 ± 0.9 | 10.0 ± 1.7 |
| 3.0 | 32.0 ± 0.8 | 33.0 ± 1.0 |
| 3.5 | 63.0 ± 1.1 | 68.1 ± 1.4 |
| 4.0 | 81.5 ± 1.7 | 85.1 ± 1.2 |
| 4.5 | 85.0 ± 0.8 | 89.2 ± 1.1 |

*Refers to the mean (±SD) of three independent estimations each involving $10^3$ appressoria (P < 0.05).

Figure 19:
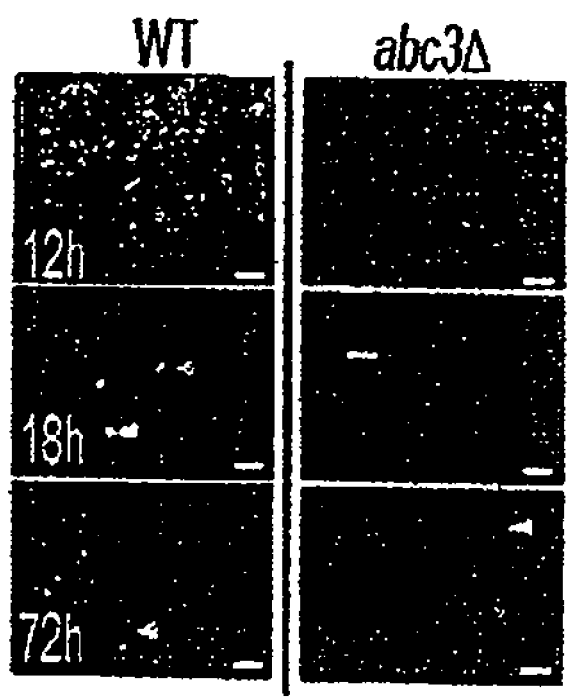
Figure 20:
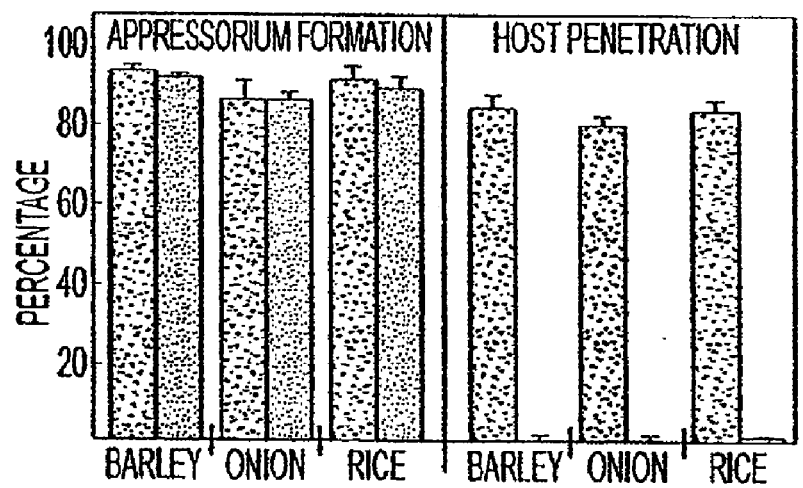

The TMT2807 and the abc3Δ strain had been isolated as totally nonpathogenic mutants incapable of causing blast disease or host damage. Therefore, detailed microscopic analyses of the infection cycle was performed to determine which stage of the pathogenesis process was compromised in the abc3Δ strain. Equal numbers of conidia from the wild type strain or the abc3Δ mutant were inoculated on barley-leaf explants, onion epidermal strips or rice-leaf sheaths and allowed to proceed through infection-related development for the indicated time. The appressoria were assessed for appressorium formation at 24 hours and appressorium function (host penetration and invasion, as judged by aniline blue staining of resultant callose deposits) at 48 hours. The resulting data are shown in FIG. 18 (onion epidermal strips) and FIG. 19 (barley leaf explants), and are quantitated in FIG. 20 (wild type, shaded; abc3Δ mutant, black). The papillary callose deposits (FIG. 19, arrowhead; see FIG. 20 for quantitation) and infection hyphae (FIG. 19, asterisk) were visualized after staining the barley-leaf explants with aniline blue at 48 hours (FIG. 19, top panels) or 72 hours (FIG. 19, lower panels) post inoculation. The inset in FIG. 19 shows a rare papillary callose deposit (arrowhead) produced by the abc3Δ appressoria. Values in FIG. 20 are the mean±SD from three replicates of the experiment each involving $10^3$ conidia.

A striking difference was that compared to the wild type organism, only a negligible percentage of abc3Δ appressoria (0.7±0.9%; n=3000, over three replicates) were able to produce penetration pegs as judged by aniline blue staining for papillary callose deposits and infection hyphae formation. See FIGS. 18, 19 and 20 (48 hours). In the wild type strain, the ability to form penetration pegs on barley leaves was about 83% (±2.9; n=3000) at the equivalent 48-hour time-point. Even upon extended incubation, host surface penetration failed to increase. See FIG. 18 (72 hours). Even after 96 hours post inoculation, a vast majority of the abc3Δ appressoria (~99%) still failed to enter the host and to elicit callose deposition. In contrast, wild type infectious hyphae within the host were already in their ramifying and proliferating stage in planta.

Figure 21:
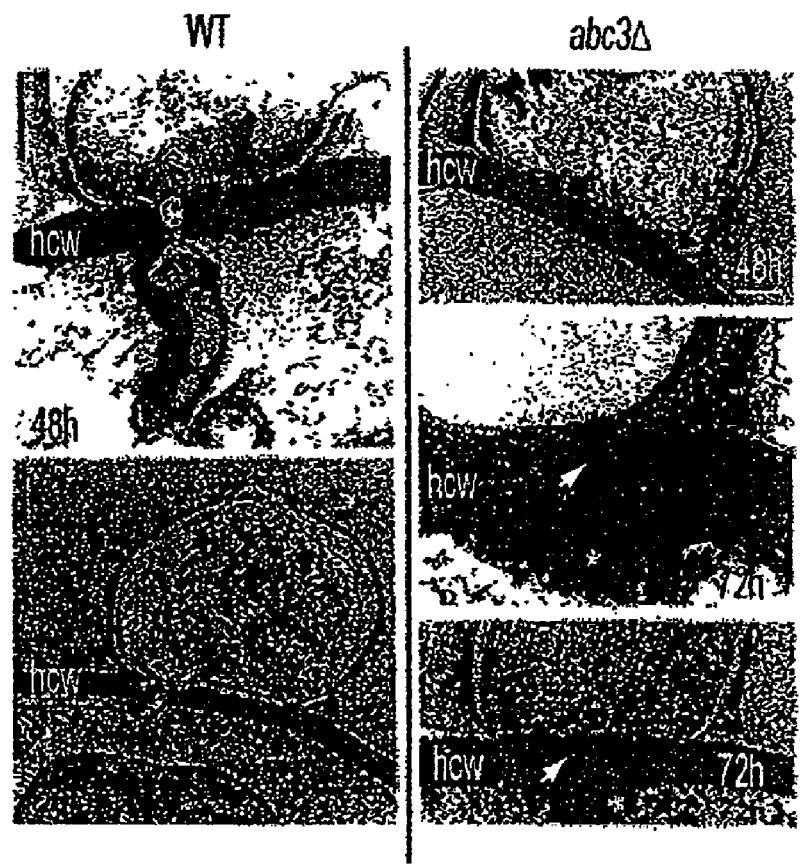

To further validate these findings, thin-section transmission electron microscopy ultrastructural analysis was performed. Barley leaves were challenged with conidia from the wild type or the abc3Δ mutant and processed for thin-section transmission electron microscopy at the indicated time points post inoculation. Near-median transmission electron microscopy sections were selected for assessment and are represented in FIG. 21. In each panel of FIG. 21, hcw indicates the host cell wall. Arrowheads indicate the non-functional penetration pegs elaborated by abc3Δ appressoria. Callose deposits are marked by an asterisk. This analysis confirmed that the majority of the abc3Δ appressoria failed to penetrate the host surface and did not elicit any visible reaction from the plant. See FIG. 21, abc3Δ, 48 hours. Futile attempts at penetration were noticeable in only two appressoria out of 142 appressoria sectioned in the abc3Δ mutant. See FIG. 21, abc3Δ, 72 hours. In each instance, dense papillary callose deposits obstructing the site of failed entry were clearly visible. On the other hand, the transmission electron microscopy sections for wild type appressoria showed successful penetration and elaboration of typical fungal infectious hyphae in the host tissue.

Figure 22:
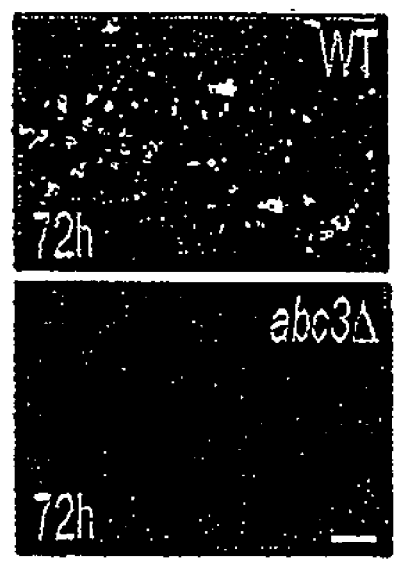
Figure 23:
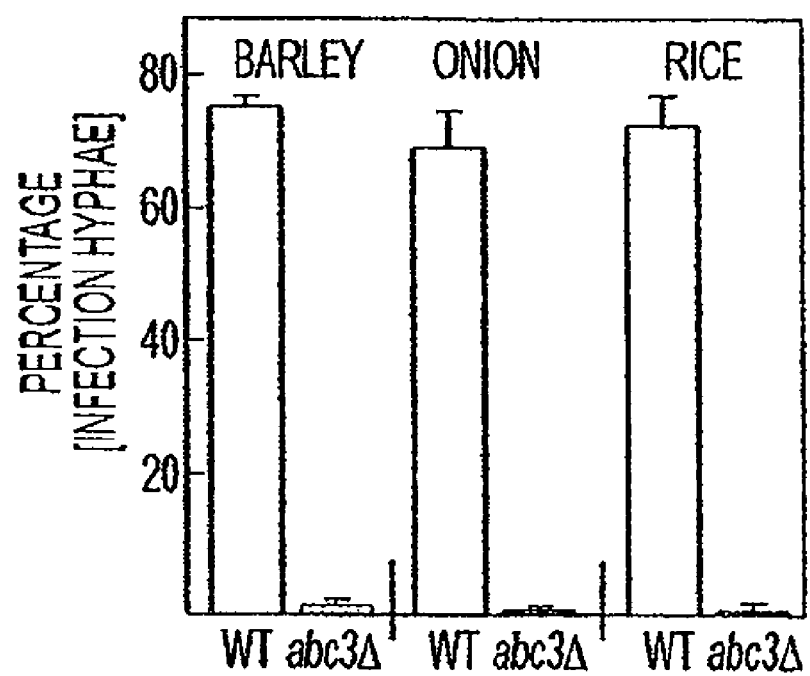

Conidia from the wild type or the abc3Δ mutant were inoculated on Barley-leaf explants, onion epidermal strips or rice-leaf sheaths and processed for aniline blue staining after 72 hours. See FIG. 22. Arrowheads indicate the infection hyphae within the leaf sheath tissue. Data for the infection hyphae from three independent experiments in each instance are graphically represented in FIG. 23, where values (±SD) are indicated as percentage points. These results lead to the conclusion that a defect in appressorium-mediated host penetration leads to the inability of mutants lacking the ABC3 function to produce pathogenicity. Taken together, these data indicate that Abc3p plays an extremely important role in the host penetration step of disease establishment and probably also is required for the in planta spreading of the blast fungus.

In addition, abc3Δ organisms were incapable of surviving the host environment, since viable abc3Δ cultures could not be recovered from the penetration assays or the wounding assays beyond 30 hours post inoculation. Conidia from the wild type (FIG. 24, shaded bars) or the abc3Δ (FIG. 24, black bars) strains were inoculated on barley-leaves (host) either by surface inoculation or the injection method or cellophane membrane and allowed to undergo pathogenic development. Cell viability was quantified at the time-points indicated in FIG. 24 by staining with Phloxine B. Values represent the mean±SD from three experiments. Quantitative cell-viability assays using Phloxine B (which accumulates in dead cells) showed that the abc3Δ mutant was incapable of surviving the environment encountered within the host irrespective of the mode of entry (surface inoculation or injection). See FIG. 24.

Figure 24:
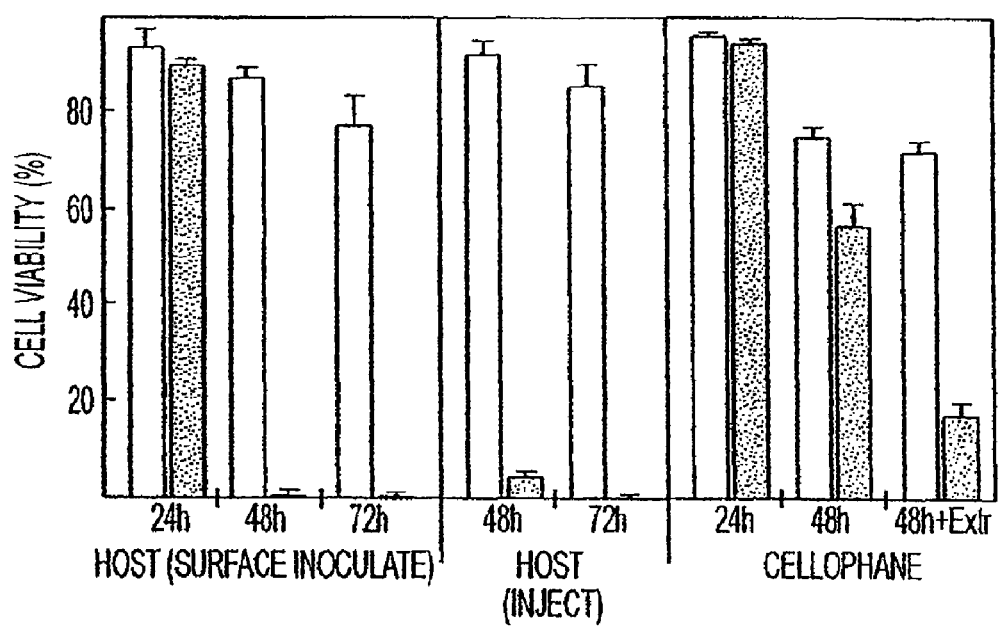

Appressorial assays on cellophane revealed that viability and invasive growth is significantly compromised in the mutant (FIG. 24, 48 hours; P<0.05). Moreover, adding barley-leaf extract during the appressorial assays on cellophane caused a further and marked reduction in the viability of the mutant therein. See FIG. 24 (48 h+Extr).

For preparing barley-leaf extracts, fresh samples from 21-day-old seedlings were surface-sterilized and ground to a fine powder using liquid nitrogen in a mortar and stirred in cold, sterilized distilled water. Ten milliliters of water per gram of leaf material was added to the sample. The mixture was kept in a refrigerator for 2 hours and then stirred on a rotary shaker for 1 hour and centrifuged at 5000 rpm for 15 minutes. The supernatant was collected and stored in a refrigerator until it was used as a crude water-soluble extract.

The wild type strain remained largely unperturbed under these conditions, therefore it is likely that the ABC3 protein plays a critical role during early stages of disease establishment and is most likely required for the in planta viability and survival of the blast fungus. A parallel experiment included viability counts during appressorium development and penetration of cellophane in the presence of water-soluble extracts from barley leaves for 48 hours (Extr).

Example 6

ABC3 Protein P-Glycoprotein and Multidrug Resistance

Earlier studies have documented the role of P-glycoproteins in the efflux of a diverse range of compounds such as steroid hormones (Uhr et al., "Penetration of endogenous steroid hormones corticosterone, cortisol, aldosterone and progesterone into the brain is enhanced in mice deficient for both mdr1a and mdr1b P-glycoproteins" J. Neuroendocrinol. 14:753-759, 2002), mating pheromone (Ketchum et al., "The yeast a-factor transporter Step 6p, a member of the ABC superfamily, couples ATP hydrolysis to pheromone export" J. Biol. Chem. 276:29007-29011, 2001), drugs and antibiotics (Nishi et al., "A leptomycin B resistance gene of *Schizosaccharomyces pombe* encodes a protein similar to the mammalian P-glycoproteins" Mol. Microbiol. 6(6):761-769, 1992), and extrusion of ions or solutes (Kimura et al., "Effects of P-glycoprotein inhibitors on transepithelial transport of cadmium in cultured renal epithelial cells, LLC-PK1 and LLC-GA5-COL150" Toxicology, 208:123-132, 2005). To test whether ABC3 protein serves similar extrusion function(s), the drug sensitivity of the abc3Δ strain and wild type Guy11 were investigated with respect to the effect of metabolic poisons, antifungal agents, and antibiotics.

Drug sensitivity of cells was assayed by measuring the minimum inhibitory concentration (MIC) of that compound required for inhibiting mycelial growth in wild type Guy11. The compounds used in the drug sensitivity assays were as follows, Valinomycin, Verapamil, Benomyl, Gramicidin D, Brefeldin A, Leptomycin B, Actinomycin D, Fluconazole and Itraconazole. For the assay, the cells were cultured on agar medium plates containing the specified concentration of each drug at 28° C. for 2-8 days. For tests on conidial function during pathogenic phase, the specified amounts of the compounds in the appropriate solvent were added directly to the aqueous suspension of conidia. The sensitivity to each indicated compound (drug sensitivity) is shown in Table III, below. Among the drugs tested, the abc3Δ strain showed increased sensitivity to Valinomycin and Actinomycin D. Multidrug resistance correlated with the function of an ABC or P-glycoprotein transporter since it could be reversed by the presence of Verapamil in Guy11. The MIC assays did not show any difference in the sensitivity of Guy11 and abc3Δ mutant for the other compounds tested such as Brefeldin A, Gramicidin D, Leptomycin B, Benomyl and some azole fungicides.

TABLE III

Drug Sensitivity* of Wild-type Strain Guy11 and abc3Δ Mutant.

| Compound | Guy11 | abc3Δ |
|---|---|---|
| Valinomycin | 20 µg/ml | 3 µg/ml |
| Valinomycin + Verapamil | 10 µg/ml | 3 µg/ml |
| Actinomycin D | 15 µg/ml | 3.5 µg/ml |
| Actinomycin D + Verapamil | 8 µg/ml | 3.5 µg/ml |
| Benomyl | 2 µg/ml | 2 µg/ml |
| Brefeldin A | 40 µg/ml | 40 µg/ml |
| Gramicidin D | 180 µg/ml | 180 µg/ml |
| Leptomycin B | 7.5 ng/ml | 7.5 ng/ml |
| Fluconazole | 2.5 mg/ml | 2.5 mg/ml |
| Itraconazole | 2 mg/ml | 2 mg/ml |

*The Minimum Inhibitory Concentration (MIC) that is sufficient to inhibit growth of *Magnaporthe* vegetative mycelia on agar medium.

Having confirmed an important efflux-related role of ABC3 protein during the mycelial growth phase of *Magnaporthe*, further tests were performed to assess whether ABC3 protein is required during the pathogenic phase for a similar MDR function. Equivalent serial dilutions of wild type or abc3Δ conidial suspensions were cultured in the presence (20 mg/ml) or absence (0 mg/ml) of Valinomycin on complete growth medium (FIG. 25) for 5 days or on artificial inductive membranes (FIG. 26) for 36 hours. Addition of potassium (KCl at 100 mM) failed to reverse the defects associated with Valinomycin action on *Magnaporthe* condiospores and appressoria.

Figure 25:
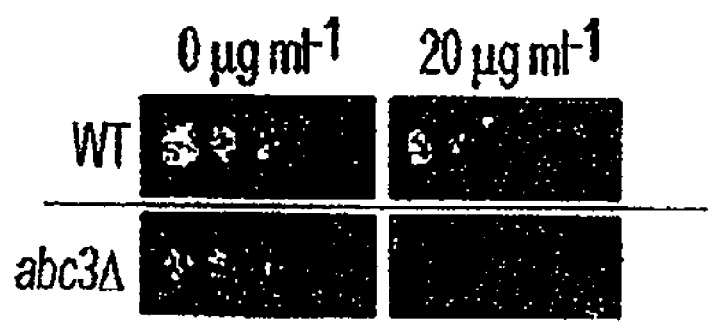
Figure 26:
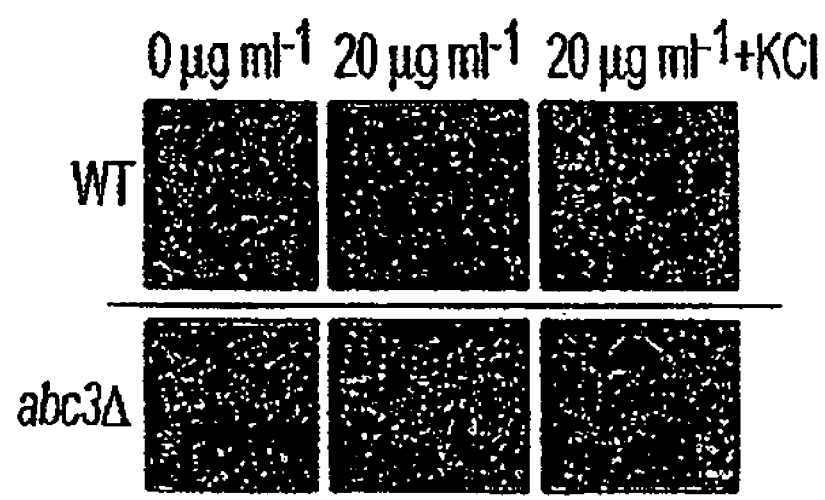

As shown in FIG. 25, the germ tube growth from abc3Δ conidia was inhibited upon Valinomycin treatment, whereas the germ tube growth in Guy11 could withstand elevated concentration of Valinomycin (20 mg/ml). On proper inductive surfaces, the wild type conidia germinated and formed appressoria in the presence of Valinomycin, albeit at a lower frequency (61±2% versus 93±5% for untreated wild type samples). See FIG. 26. The appressoria formed under these conditions were also substantially smaller in size. In contrast, the same concentration of Valinomycin had a very severe and dramatic effect on the conidia of the abc3Δ mutant: a complete blockage of conidial germ tube emergence. See FIG. 26.

Daniele and Holian, "A potassium ionophore (valinomycin) inhibits lymphocyte proliferation by its effects on the cell membrane" Proc. Natl. Acad. Sci. USA, 73:3599-3602, 1976 have proposed that valinomycin also can affect the homeostasis of potassium ions across biological membranes. However, exogenous addition of potassium chloride did not suppress the effect of Valinomycin on either wild type or abc3Δ conidia and appressoria. Therefore, it is likely that the ABC3 protein serves an essential multidrug-resistance function both during the vegetative and the pathogenic phase of the rice-blast fungus and that such MDR activity is most likely towards compounds structurally or functionally similar to valinomycin.

Figure 27:
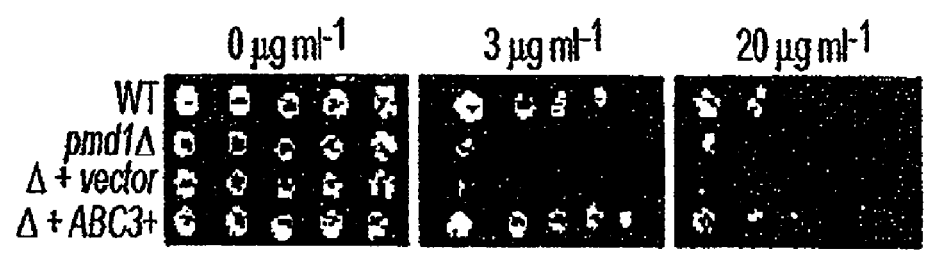

Fission yeast strains belonging to the relevant genotypes (as specified in FIG. 27) were cultured on YES medium in the absence or presence of the indicated amounts of Valinomycin. Results were documented 5 days post inoculation. Strain D+vector refers to the pmd1D mutant carrying an empty plasmid vector, whereas D+ABC3$^+$ denotes the pmd1D mutant expressing an integrated copy of the ABC3 gene. Thus, ABC3 protein also could functionally replace its ortholog Pmd1p from fission yeast signifying the evolutionary conservation and importance of such multidrug resistance phenomenon.

Example 7

ABC3 Protein and Sensitivity to Cellular Stress

High potassium levels could not reverse the effect of Valinomycin. The ABC3 protein may function through some as yet unknown mechanism to modulate its MDR activity towards such antifungal compounds. To test whether ABC3 is required for modulating osmotic, oxidative and related cellular stress conditions, further studies were performed. Mycelial plugs (FIG. 28) or equivalent serial dilutions of conidiospore suspensions (FIG. 29) from abc3Δ or wild type strains were cultured on minimal agar medium containing the indicated amounts of hydrogen peroxide. The results were documented after an incubation period of one week.

Figure 28:
Figure 29:
FIG. 29 shows serial dilutions of conidiospore suspensions from the wild type or abc3Δ strain cultured on minimal agar medium with the indicated amounts of hydrogen peroxide.

Compared to the wild type strain, abc3Δ mutant did not show any difference in its mycelial growth in the presence of high concentrations of osmolytes such as sorbitol, sucrose or sodium chloride. In contrast, the abc3Δ mutant was found to be highly sensitive to oxidative stress. Even relatively low concentrations of hydrogen peroxide (2 mM) were lethal to the mutant strain (FIG. 28), whereas the wild type Guy11 strain was unaffected under these adverse growth conditions (FIG. 28). The abc3Δ mutant also showed similar sensitivity to paraquat and menadione, which stimulate accumulation of reactive oxygen species/intermediates. The sensitivity of abc3Δ mutant to such oxidative stress was common to the vegetative as well as the pathogenic growth phase (FIG. 29).

Figure 30:
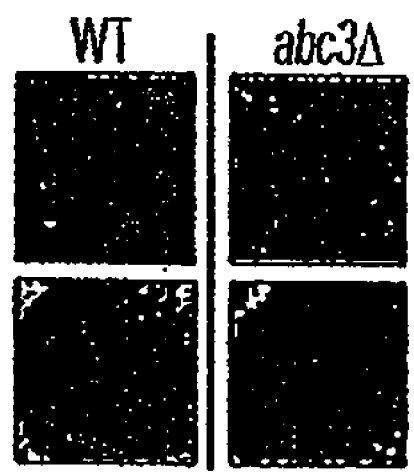
FIG. 30 shows three-(top panels) or six-(bottom panels) day-old colonies of wild type or abc3Δ colonies, stained with NBT solution to detect peroxide accumulation.

FIG. 30 shows nitroblue tetrazolium (NBT)-assisted visualization of the accumulation of reactive oxygen radicals in wild type and abc3Δ colonies. Three-(top panels) or six-(lower panels) day-old wild type or abc3Δ colonies were stained with NBT solution to detect peroxide accumulation. The mutant hyphae accumulated relatively higher amounts of peroxide and likely a higher amount of reactive oxygen species. In FIG. 30, the dark centers in the wild type colonies are due to the enhanced contrast of the image.

Figure 31:
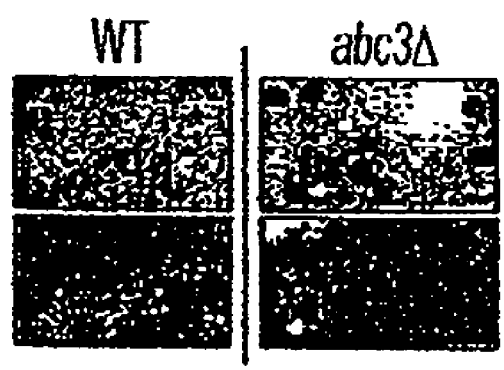
FIG. 31 shows wild type and abc3Δ appressoria formed on artificial membranes (upper panels) or on barley leaf explants (lower panels), stained with diaminobenzidine to detect the accumulation of hydrogen peroxide (arrowheads) Bar=10 mm.

Accumulation of hydrogen peroxide was visualized with diaminobenzidine (DAB) in wild type and in abc3Δ mutant appressoria formed on artificial membranes. Wild type and abc3Δ appressoria formed on artificial membranes (upper panels) or on barley leaf explants (lower panels) were stained with diaminobenzidine to detect the accumulation of hydrogen peroxide (arrowheads). Arrows indicate the excess diaminobenzidine-reactive deposits within the appressorial lumen. See FIG. 31, upper panels. This showed that the mutant accumulates a relatively higher amount of peroxide levels, which likely would lead to a higher amount of reactive oxygen species. Increased accumulation of peroxides/DAB-positive material also was detected in the abc3Δ mutant appressoria on artificial membranes and barley-leaf explants (FIG. 31, lower panels).

Figure 32:
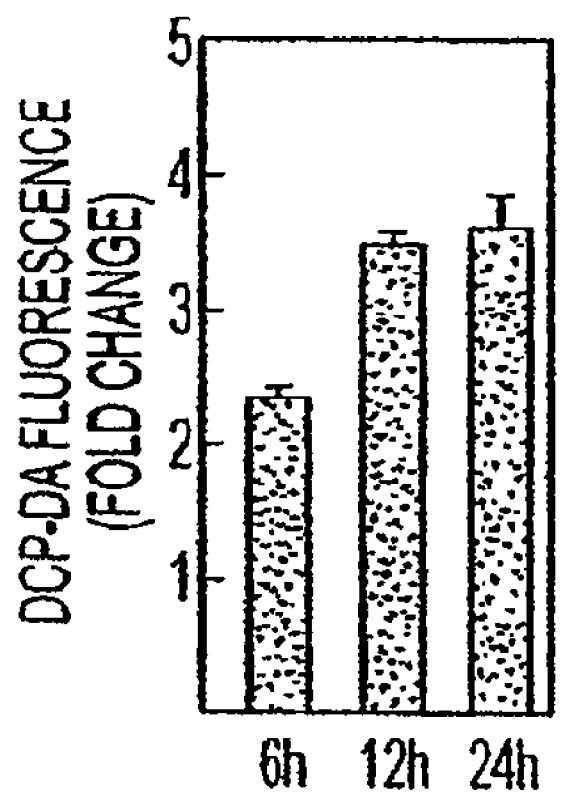
FIG. 32 is a fluorometric analysis showing total extracts from wild type or abc3Δ appressoria, treated with CM-DCFDA.

Fluorimetric evaluation of hydrogen peroxide levels in wild type and abc3Δ strains on barley leaves, after staining with the dye CM-DCFDA (chloromethyl-2',7'-dichlorofluorescein diacetate, Molecular Probes, USA), revealed that the mutant appressoria accrue 3.5 fold higher amounts of ROS/peroxide than those estimated in the wild-type (FIG. 32). Total extracts from wild type or abc3Δ appressoria were treated with CM-DCFDA and processed for fluorimetric estimations. Values in the graph represent fold change (mean±SD; from three independent experiments) in the CM-DCFDA-reactive material from mutant appressorial extracts compared to those in the wild type. Average value for the CM-DCFDA estimates in the wild type extracts was set at one. An earlier study has shown that oxidative stress (accumulation of DAB-positive material) precedes the elicitation of cell death in the interacting epidermal cells and the underlying mesophyll cells in Brachypodium infected with Magnaporthe (Routledge et al., "Magnaporthe grisea interactions with the model grass Brachypodium distachyon closely resemble those with rice (Oryza sativa)" Mol. Plant Path., 5:253-265, 2005). These results indicate that ABC3 protein protects the blast fungus from oxidative damage in the mycelial growth phase and also during the host-associated stage of pathogenic development and proliferation.

Example 8

Partial Suppression of abc3Δ Defects, and Effect of Verapamil and Oxidative Stress To understand whether the pathogenicity defects in abc3Δ are in any way related to the excess build-up of $H_2O_2$ therein, attempts were made to reduce the levels of peroxide oxidants during appressorium development by using several agents such as, Diphenyleneiodonium (DPI; 15 mm), nordihydroguaiaretic acid (NDGA, 10 mm), 5 mm Rotenone (Chiarugi et al., 2003) or antioxidants (Ascorbate or N-acetylcysteine).

Figure 33:
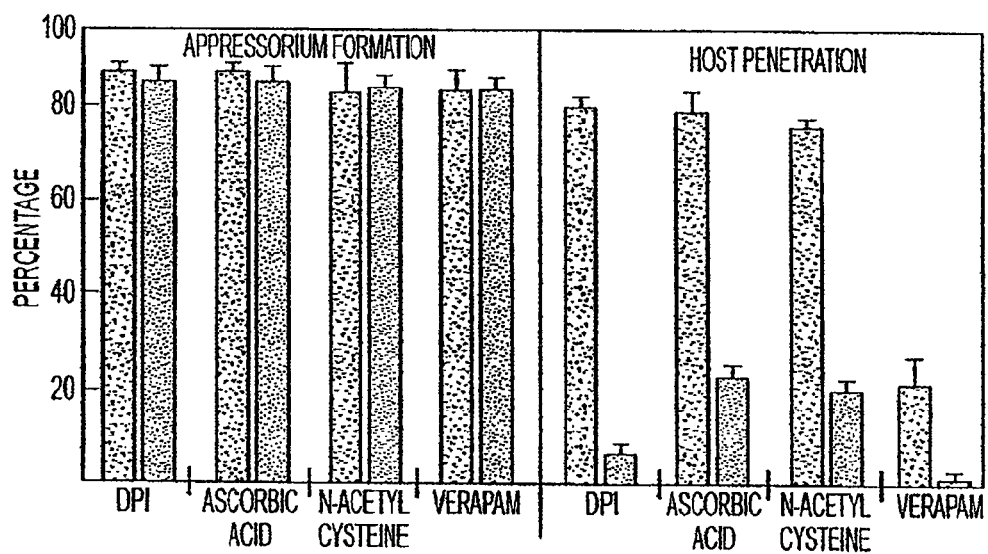
FIG. 33 is a bar graph showing the degree of restoration of appressorium function by antioxidant treatment. Values in FIG. 33 represent mean±SD from three independent experiments each involving 2000 conidia per strain.

Antioxidant treatment partially restored appressorium function in abc3Δ wild type (FIG. 33, shaded bars) or abc3Δ (FIG. 33, black bars). The conidia were tested for appressorium formation and function (host penetration) on barley-leaf explants in the presence of DPI, ascorbate or N-acetylcysteine. This test also was carried out in the presence of Verapamil (Verapam), a generic inhibitor of MDR-based efflux functions. The treatments were carried out for 48 hours in each instance and host penetration was assessed by aniline blue staining. The addition of Diphenyleneiodonium suppressed the host penetration defects associated with the abc3Δ appressoria in 5.1±1.1% appressoria (n=3000). See FIG. 33. Antioxidant treatment with either ascorbate or N-acetylcysteine restored penetration function in 23±2.5% and 19±1.6% appressoria, respectively (n=3000, P<0.005), as judged by papillary callose deposition. See FIG. 33. However, the resultant mutant penetration pegs still failed to elaborate proper infection hyphae and were unable to advance the invasion further. The reduction of the intracellular peroxide levels (or oxidative stress) in abc3Δ therefore leads to a significant suppression of the appressorial defects in this mutant.

Figure 34:
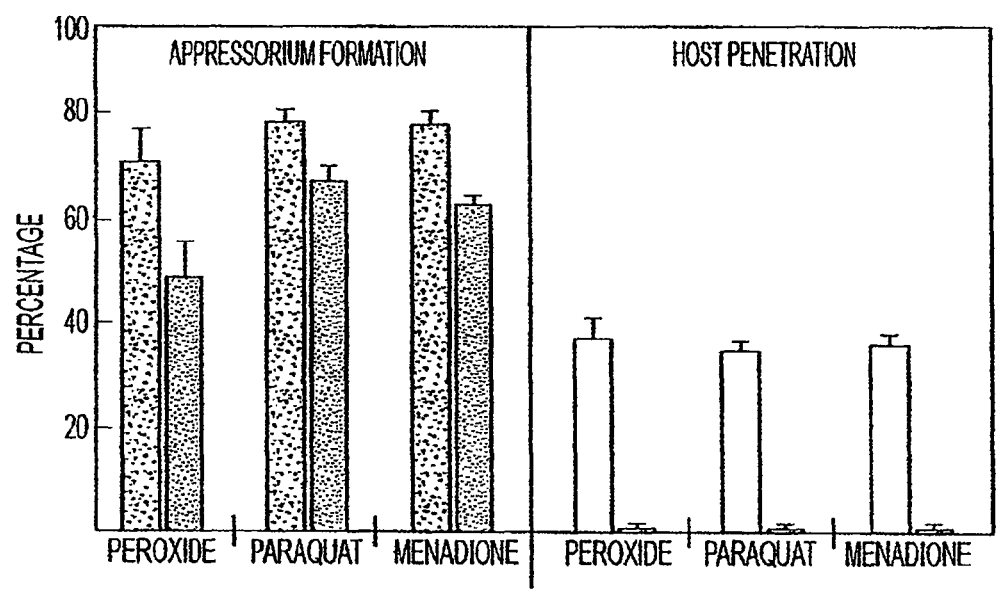
FIG. 34 shows the percentage of appressoria that elaborated penetration pegs in the presence and absence of 3 mM peroxide.
Figure 35:
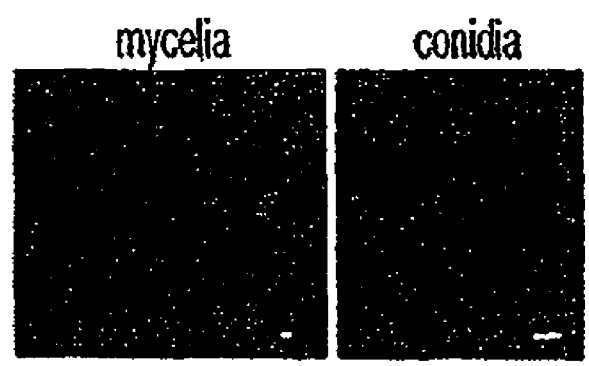
FIG. 35 is a set of photographs of mycelia and conidia harvested from a strain expressing an ABC3-GFP fusion protein and imaged using laser-scanning confocal microscopy to detect the eGFP signal. Bar=10 mm.
Figure 36:
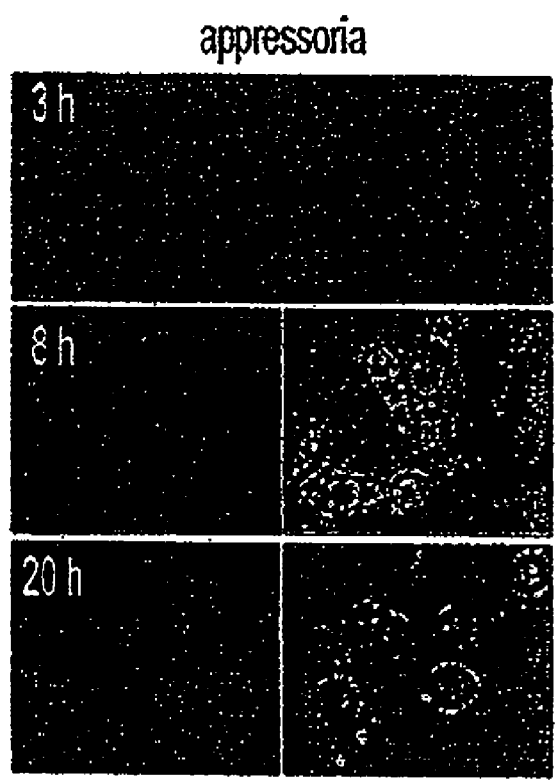
FIG. 36 is a set of photographs showing appressorium development in the germ tubes of a *Magnaporthe* strain expressing ABC3-GFP strain at the indicated time points, imaged using GFP epifluorescence. Bar=10 mm.
Figure 37:
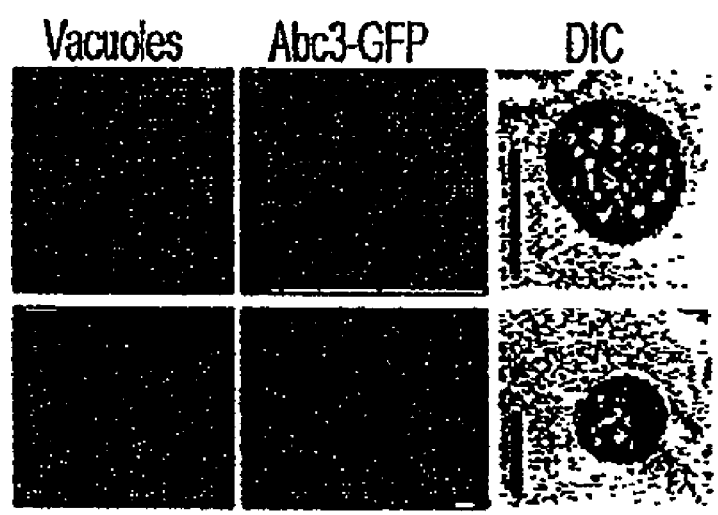
FIG. 37 is a set of photographs showing vacuolar distribution of ABC3-GFP. Scale bars denote 10 mm.
Figure 38:
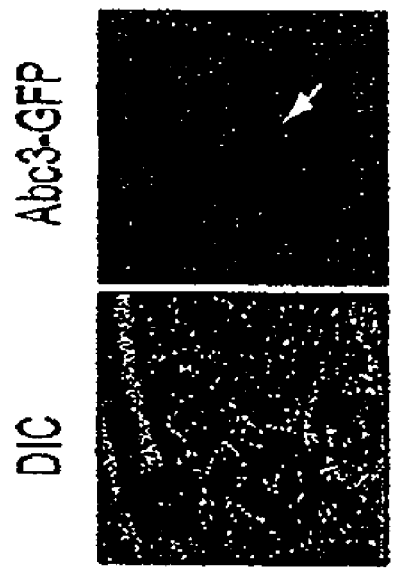
FIG. 38 is a set of photographs showing confocal microscopy assisted analysis of ABC3-GFP localization in the penetration structures (arrowhead) elaborated by the appressoria in PUDO-193 membrane. Bar=10 micron.

In a converse experiment, the effect of exogenous hydrogen peroxide, menadione or paraquat on the ability of the wild type appressoria to penetrate the host surfaces was tested. Conidia from the wild-type (FIG. 34, shaded bars) or the abc3Δ strain (FIG. 34, black bars) were inoculated on barley-leaf explants in the presence of either hydrogen peroxide or paraquat or Menadione and the resultant appressorium formation and function (host penetration) assessed after 48 hours as described above. Values represent mean±SD from three independent experiments each involving 2000 conidia per strain.

As expected, in the absence of exogenous peroxide, the wild type appressoria behaved normally and were able to successfully penetrate the host surface as judged by papillary callose deposits upon aniline blue staining. The percentage of appressoria that elaborated penetration pegs was 68±2.3% (n=3000, over 3 replicates), after the 48-hour time point. See FIG. 34. Addition of 3 mM peroxide to the wild type conidia caused a significant decrease in host penetration with only 36±2.8% appressoria (n=3000, over 3 replicates) able to breach the host surface. See FIG. 34. Addition of paraquat or Menadione had a slightly reduced effect on host penetration of the wild type strain, as compared to treatment with peroxide. See FIG. 34. Such oxidative stress caused a significant reduction in the efficiency of appressorium formation and peroxide levels exceeding 5 mM blocked germ tube emergence in the wild type conidia.

Downregulation of MDR activity by Verapamil during pathogenic development produced a significant decrease (maximal 74%) in penetration peg formation, but without affecting the germ tube emergence or growth. These results suggest that excessive peroxide levels have an adverse effect on the host-penetration capacity of *Magnaporthe*, and that reducing the intracellular levels of peroxide (or oxidative stress) in abc3Δ significantly suppresses the appressorial defects observed in this mutant. Taken together, it is clear that ABC3 protein performs an important MDR function during the pathogenic phase and possibly protects the blast fungus from peroxide-based internal oxidative stress during vegetative growth and pathogenic development.

Example 9

Subcellular Localization of GFP-Tagged ABC3 Protein

The predicted secondary structure of ABC3 protein suggests that it is an integral membrane protein. In order to determine the distribution pattern of ABC3-protein within the various cell types of *Magnaporthe*, the abc3-GFP fusion construct was introduced into the Guy11 strain. Two transformants carrying single copy of abc3:GFP allele, tagged at the genomic locus, and two control strains were identified by PCR analyses and further confirmed by Southern and western blot analyses. GFP detection was performed either by epifluorescence microscopy or by confocal laser-scanning fluorescence microscopy. Strains expressing ABC3-GFP showed no obvious differences in growth or pathogenesis compared to the wild type strain, suggesting that ABC3-GFP is fully functional. ABC3-GFP was judged to be a plasma membrane resident protein based on the distinct green fluorescence in the mycelial outer membranes. See FIG. 35. No detectable GFP signals were observed in the conidia of the ABC3:GFP strain (FIG. 35), although the germ tubes showed a faint GFP signal in the plasma membrane.

A time-course analysis during appressorium development and maturity suggested that the ABC3-GFP protein was highly expressed and concentrated in the appressorial plasma membrane right from the incipient stage onwards (FIG. 36). Appressorium development in the germ tubes of the ABC3-GFP strain was monitored over a 24 hour period. At the indicated time points post germination, GFP epifluorescence was imaged to locate the ABC3-GFP fusion protein. At 17 hours post germination, during appressorium maturation, ABC3-GFP signal was predominantly found in the vacuolar compartments (FIG. 36, 20 hours) as well, although the plasma membrane residency was diminished substantially.

For vacuolar staining, LysoTracker™ Red DND-99 (50 nM final concentration) and Neutral Red (50 nM) were used as per the manufacturer's (Invitrogen™) recommendation. Co-localization studies to confirm vacuolar residency involved staining with LysoTracker Red DND-99 or with Neutral Red. Appressoria formed by the Abc3-GFP strain were stained with LysoTracker Red DND-99 (left panel, vacuoles) or with Neutral Red (right panel) at the 20 hour time point to visualize vacuoles. See FIG. 37.

Nitroblue tetrazolium (Sigma-Aldrich™) was used at 4 mg/ml (in de-ionised water) and the staining carried out for 1 hour at room temperature prior to observation. Cell viability was measured by staining dead cells as follows: samples were stained with 20 mg/ml Phloxine B (Sigma-Aldrich, USA) for 1 hour at room temperature and the samples subjected to a short wash with PBS prior to microscopic analysis and quantification. As controls for dead cells, wild-type cells were incubated for 30 min at 65° C. and stained with Phloxine B in parallel. The ABC3-GFP localization during host penetration and invasive growth revealed that ABC3-GFP was present in the plasma membrane of the newly formed penetration hyphae (FIG. 38) but was undetectable in the resultant infection hyphae. Consistent with its role in appressorium function and its localization pattern described above, these data indicate that *Magnaporthe* ABC3 protein is a transmembrane protein found in the mycelia and predominantly in the appressoria. It therefore is possible that it is most likely required for the efflux of toxic metabolite(s), and/or for regulating the oxidative stress within these highly important fungal infection structures.

Reactive oxygen species were detected by staining with a solution of 3, 3-Diaminobenzidine (DAB, 2 mg/ml) for 2 hours followed by clearing in a solution of acetic acid:glycerol:ethanol (1:2:2) at 80° C. for 5 min and subsequently stored in 3% glycerol or by staining with 2',7'-dichlorofluorescein diacetate (10 μM; in 30 mM KCl and 10 mM MES-KOH pH 6) for 1 h at room temperature. For fungus-inoculated leaf material, the DAB and Trypan blue stainings were essentially as described (Thordol-Christensen et al., 1997 and Gilbert et al., "A P-type ATPase required for rice blast disease and induction of host resistance" Nature, 440:535-539, 2006 respectively). In the co-staining method, diaminobenzidine was used prior to sample clarification and Trypan blue treatment. Antioxidants ascorbic acid and N-acetylcysteine were used at 5 mM concentration.

The intracellular formation of reactive oxygen species in appressoria was quantified using the fluorescent probe CM-DCFDA (chloromethyl-2',7'-dichlorofluorescein diacetate; Invitrogen Corporation, USA). The appressorial preparation from the requisite strain was washed two times in phosphate-buffered saline and exposed to 50 mM CM-DCFDA in PBS for 1 hour at 28° C. The appressoria then were washed two times in PBS, solubilized in water, and homogenized in a Mini Bead-beater™ to obtain the intracellular extracts. The fluorescence was determined at 488/525 nm, normalized on a protein basis, and expressed as fold change over the wild type control, which was arbitrarily set at 1.

At a later stage during the appressorium formation (17 hours post germination), ABC3-GFP signal was predominantly found in the vacuolar compartments as well, although the plasma membrane residency was not altered. See FIG. 39. Consistent with its role in appressorium function, the localization pattern described above indicates that ABC3 protein is a transmembrane protein found predominantly in the mycelia and the appressoria, where it is most likely required for the efflux of xenobiotic compounds, and/or for regulating the oxidative stress within the fungal structures.

Example 10 abc3Δ Appressoria Accumulate Toxic Metabolite(s)

The prediction that ABC3 protein was an MDR protein raised the possibility that the abc3Δ appressoria could retain cytotoxic molecule(s) that block the appressorial function of elaborating penetration pegs. To investigate this possibility, intracellular and extracellular extracts were prepared from the appressoria of the wild type or abc3Δ strain as described in Example 9, above. See FIG. 40. These extracts were used individually during plant infections with wild type conidia by adding the extracts to wild type conidia in barley leaf infection assays at 0 hours (top panels) or 23 hours (bottom panels) post inoculation. A solvent control at the equivalent concentration was included in parallel. The values in FIG. 40 indicate penetration efficiency (mean values as percentage points±SD from three replicates) calculated after 48 hours by staining papillary callose deposits with aniline blue.

The intracellular extract from the abc3Δ appressoria, when added at the start of the wild type infection, caused a dramatic (~74%; P<0.005) reduction in penetration-peg formation, by aniline blue staining for papillary callose deposits, See FIG. 40. There was no decrease in the appressorium formation capability under these conditions. The corresponding extract from the wild type appressoria resulted only in a slight decrease (~24%) in host penetration. This decrease by the wild type extract was comparable to the reduction observed when the extract from either the wild type or the mutant strain was added after the infection had proceeded for 23 hours. See FIG. 40. The control extracts did not cause any significant decrease in the host penetration capability of the wild type appressoria, nor did the extracellular extracts from either the wild type or the abc3Δ appressoria. Theoretically, it is possible that the abc3Δ mutant is unable to efflux certain toxic or inhibitory metabolite(s), the accumulation of which in the mutant appressoria likely inhibits host penetration.

The ability of the abc3Δ appressoria intracellular neutral toxin extract to suppress penetration of artificial substrates by the wild type or mutant strains was tested. To extract intracellular neutral toxins, about $2 \times 10^6$ conidia (wild type or abc3Δ) were inoculated in de-ionised water on the hydrophobic side of GelBond™ membranes (BioWhittaker Molecular Applications™) and allowed to form appressoria for 20 hours at room temperature under high humidity. The deionized water was aspirated and the resultant appressoria washed once with chilled water, scraped immediately and ground into a fine powder using liquid nitrogen. The homogenate was extracted with 1 ml of chloroform/methanol (1/1, v/v) and the mixture shaken for 10 minutes and centrifuged at 3000 rpm for 5 minutes. The extracted material was evaporated to dryness using rotary evaporation. The residue was partitioned between 1 ml n-hexane and 1 ml 90% methanol (1/1, v/v); the n-hexane layer was discarded and the methanol layer evaporated to dryness as above. The solids were then partitioned between 1 ml chloroform and 1 ml de-ionized water. The chloroform layer was extracted with saturated sodium hydrogen carbonate solution (3×1 ml). The chloroform layer was then concentrated to dryness and contained the neutral extraction (toxins). This was finally resuspended in 100 ml of deionized water. The same procedure was repeated but without any conidia to serve as a solvent-only control for experiments with the neutral toxins.

To obtain the extracellular toxin(s), about $2 \times 10^6$ conidia (wild type or abc3Δ) were inoculated in deionized water on the hydrophobic side of a GelBond™ film and allowed to form appressoria for 20 hours at room temperature under high humidity. All extracellular solution was collected, centrifuged to pellet the debris, and the remaining supernatant transferred to fresh tubes and concentrated by drying in an Eppendorf™ Concentrator 5301. The dried pellet was resuspended in 0.1 ml deionized water.

Wild type and abc3Δ appressorial assays were performed on PUDO-193 cellophane in the presence (+EXT) or absence (−EXT; solvent control) of this extract. As shown in FIG. 41, addition of the intracellular neutral toxin abc3Δ extract caused a significant reduction (~85% in wild type and 89% abc3Δ; P<0.005) in appressorium function on cellophane membranes.

Cell viability was assessed with Phloxine B staining in vegetative mycelia from the wild type (FIG. 42, gray) or abc3Δ (FIG. 42, black) in the absence (−EXT; solvent control) or presence (+EXT) of the intracellular neutral toxin extract from the abc3Δ appressoria. The intracellular abc3Δ extract showed minimal effect on the viability of the wild type or abc3Δ mycelia.

The intracellular abc3Δ extract caused a dosage-dependent and noticeable reduction in the elaboration of disease symptoms on rice leaves when included during blast infection assays. Wild type conidia were tested in barley-leaf inoculation assays in the absence (−EXT; solvent control) or presence (+EXT; at 1× or 0.5× concentration) of the extract from the abc3Δ mutant. A parallel experiment was carried out in the absence of conidia. Blast symptoms were assessed and documented 5 days post inoculation. The hypersensitivity reaction (mean values±SD of rice Pr-1/Actin ratio from three independent experiments; P<0.05) was estimated at 48 hours after inoculation. See FIG. 43. The mutant extract also elicited visible hypersensitivity reaction-like symptoms (the occurrence of brown lesions in the absence of fungal biomass in treated samples and the ratio of rice Pr-1 to Actin gene expression). See FIG. 43; P<0.05. ABC3 protein therefore is important for the efflux of certain appressorial metabolite(s), the accretion of which has a negative effect on host penetration.

Example 11

Regulation of ABC3 Expression

Sequence analysis of the ABC3 promoter did not reveal the presence of putative cis-acting regulatory elements or enhancer sequences for stress response factors. However, given the above findings showing the involvement of ABC3 protein in regulating oxidative stress within the fungal cellular structures, tests were performed to determine whether such stress conditions directly influenced abc3 expression. A qualitative and quantitative study of abc3 expression was performed during the infection-related developmental stages of two independent transformants, each carrying a single-copy destabilized GFP reporter driven by the ABC3 promoter.

For GFP fusion with the TrpC terminator, a 1 kb abc3 fragment just proximal to the stop codon and a 1 kb abc3 fragment immediately downstream of the stop were ligated to pFGL44 with an HPH marker to obtain pFGLg1. The eGFP segment with the Trpc Terminator was cut out of pFGL265 by NcoI and PstI double digestion and ligated to pFGLg1 between the two abc3 fragment to obtain pFGLg2. The vector pFGLg2 was introduced into *M. grisea* using routine transformation protocols as reported in Soundararajan et al., "Woronin body function in *Magnaporthe grisea* is essential for efficient pathogenesis and for survival during nitrogen starvation stress" Plant Cell, 16:1564-1574, 2004. Transformants were selected on hygromycin and the correct gene replacement event (homology-dependent chromosomal tagging of ABC3 with GFP) confirmed by Southern and western analysis. The ABC3:GFP strains thus obtained were further tested for growth, Valinomycin sensitivity and host-penetration defects to ascertain that the ABC3-GFP was not compromised for function. Conidia from the ABC3(p)::GFP strain were allowed to undergo appressorium development for 24 hours in the absence (Control) or presence (Treated) of 1 mM hydrogen peroxide. See FIG. 44. Epifluorescent microscopic observations were performed at the indicated time points to detect GFP expression driven by the abc3 promoter.

GFP epifluorescence was observed using a Zeiss LSM510 inverted confocal microscope (Carl Zeiss, NY, USA) equipped with a 30 mW argon laser. The objectives were either 63× Plan-Apochromat (numerical aperture 1.4) or a 100× Achromat (n.a. 1.25) oil immersion lens. EGFP was imaged with 488 nm wavelength laser excitation, using a 505-530 nm band pass emission filter, while red fluorescence was detected with 543 nm laser and 560 nm long pass emission filter. Routine photomicrographs were taken using the Photometrics™ CoolSNAP-HQ™ camera mounted on a Nikon Eclipse™ 80i compound microscope equipped with differential interference contrast optics and the standard filters for epifluorescence detection.

As shown in FIG. 44, the destabilized-GFP fluorescence increased dramatically upon treatment with hydrogen peroxide. The fluorescence intensification was four fold higher compared to the untreated control samples, was maximal after a 9 hour treatment and did not show any change after the initial increase. See FIG. 44. Low levels of Paraquat or Valinomycin elicited a similar increase in the ABC3 promoter driven destabilized-GFP expression during appressorium development. These results suggest that the upstream regulatory elements of the abc3 gene respond to the model molecules that generate reactive oxygen radicals and that the abc3 transcript likely is regulated in a redox sensitive manner during infection-related development in *Magnaporthe*. In a separate experiment, a 1.8 kb fragment before the translational start site of ABC3 was used as a promoter for expressing the destabilized-GFP reporter.

To study whether ABC3 expression also is governed by host signals, semi-quantitative RT-PCR was performed to analyze total RNA extracted at various time intervals from barley leaves challenged with wild type conidia, using the methods of Soundararajan et al., "Woronin body function in *Magnaporthe grisea* is essential for efficient pathogenesis and for survival during nitrogen starvation stress." Plant Cell, 16:1564-1574, 2004. Along with ABC3, TUB1 (b-Tubulin) and Mg CHAP1 were included as controls. CHAP1 transcript has been shown to be under redox regulation in *Cochliobolus* (Lev et al., "Activation of an AP1-Like Transcription Factor of the Maize Pathogen *Cochliobolus heterostrophus* in Response to Oxidative Stress and Plant Signal." Eukaryotic Cell, 4:443-454, 2005).

Semi-quantitative RT-PCR-derived products were amplified using ABC3 or MgCHAP1 or MgTUB1 specific primers from total RNA extracted from the wild type strain grown for the indicated hours post inoculation (hpi) on barley leaves. See FIG. 45. Negative control (−RT) refers to the RNA sample processed without a reverse transcriptase step prior to the PCR amplification. GD refers to the PCR amplification of the respective fragments from the genomic DNA samples using the corresponding primer sets. Molecular mass standards (Kb) are represented in kilo-basepair.

As shown in FIG. 45, the highly abundant TUB1 showed hardly any difference in its expression during the duration of the assay. ABC3 expression was always weaker compared to TUB1, but showed an induction at 18-20 hours stage post inoculation. Its expression remained stable and strong after the induction at this time-point and continued to be so up to the 36-hour post inoculation (FIG. 45). CHAP1 expression also peaked at 12-18 hours but declined slightly after the 24-hour time point. Taken together, the results indicate that ABC3 promoter responds positively to the redox status of the cell and that the ABC3 gene expression is likely influenced by the host signals as well, with an induction, just before the fungus readies itself to enter the host tissue.

Sequences of genes referred to herein are available in the EMBL/Genbank data libraries under accession numbers DQ 156556 (ABC3), U89895 (Pe-1), AC104285 (Actin), AJ276225 (HvPr5) and U21907 (Hvact10).

REFERENCES

All references cited here and throughout the application are hereby incorporated by reference in their entirety.

1. Altschul et al., "Gapped BLAST and PSI-BLAST: A new generation of protein database search programs." Nucleic Acids Res., 25:3389-3402, 1997.
2. Andrade et al., "The ABC transporter AtrB from *Aspergillus nidulans* mediates resistance to all major classes of fungicides and some natural toxic compounds." Microbiology, 146:1987-1997, 2000a.
3. Andrade et al., "The role of ABC transporters from *Aspergillus nidulans* in protection against cytotoxic agents and in antibiotic production." Mol. Gen. Genet., 263:966-977, 2000b.
4. Bahler et al., "Heterologous modules for efficient and versatile PCR-based gene targeting in *Schizosaccharomyces pombe*." Yeast, 14:943-951, 1998.
5. Balhadère et al., "Identification of pathogenicity mutants of the rice blast fungus *Magnaporthe grisea* by insertional mutagenesis." Mol. Plant-Microbe Interact., 12:129-142, 1999.
6. Bradford, "A rapid and sensitive method for the quantitation of microgram quantities of protein utilizing the principle of protein-dye binding." Anal. Biochem., 72:248-254, 1976.
7. Chen and Dickman, "Proline suppresses apoptosis in the fungal pathogen *Colletotrichum trifolii*." Proc. Natl. Acad. Sci. USA, 102:3459-3464, 2005.
8. Chiarugi et al., "Reactive oxygen species as essential mediators of cell adhesion: the oxidative inhibition of a FAK tyrosine phosphatase is required for cell adhesion." J. Cell Biol., 161:933-944, 2003.
9. Chida and Sisler, "Restoration of appressorial penetration ability by melanin precursors in *Pyricularia oryzae* treated with anti-penetrants and in melanin-deficient mutants." J. Pestic. Sci., 12:49-55, 1987.
10. Clergeot et al., "PLS1, a gene encoding a tetraspanin-like protein, is required for penetration of rice leaf by the fungal pathogen *Magnaporthe grisea*." Proc. Natl. Acad. Sci. USA, 98:6963-6968, 2001.
11. Cole et al., "Overexpression of a transporter gene in a multidrug-resistant human lung cancer cell line." Science, 258:1650-1654, 1992.
12. Daniele and Holian, "A potassium ionophore (valinomycin) inhibits lymphocyte proliferation by its effects on the cell membrane." Proc. Natl. Acad. Sci. USA, 73:3599-3602, 1976.
13. Decottignies and Goffeau, "Complete inventory of the yeast ABC proteins." Nat. Genet., 15:137-145, 1997.
14. de Jong et al., "Glycerol generates turgor in rice blast." Nature, 389:244-245, 1997.
15. de Waard et al., "Impact of fungal drug transporters on fungicide sensitivity, multidrug resistance and virulence." Pest. Manag. Sci., 62:195-207, 2006.
16. Dixon et al., "Early events in the activation of plant defense responses." Annu. Rev. Phytopathol., 32:479-501, 1994.

17. Driessen et al., "Diversity of transport mechanisms: common structural principles." Trends Biochem. Sci., 25:397-401, 2000.
18. Felsenstein, "PHYLIP (phylogeny inference package). Version 3.2." Cladistics, 5:164-166, 1989.
19. Fleissner et al., "An ATP-binding cassette multidrug-resistance transporter is necessary for tolerance of *Gibberella pulicaris* to phytoalexins and virulence on potato tubers." Mol. Plant-Microbe Interact., 15:102-108, 2002.
20. Gilbert et al., "A P-type ATPase required for rice blast disease and induction of host resistance." Nature, 440:535-539, 2006.
21. Gottesman and Pastan, "Biochemistry of multidrug resistance mediated by the multidrug transporter." Annu. Rev. Biochem., 62:385-427, 1993.
22. Hamer and Talbot, "Infection-related development in the rice blast fungus *Magnaporthe grisea*." Curr. Opin. Microbiol., 1:693-697, 1998.
23. Higgins, "ABC transporters: from microorganisms to man." Annu. Rev. Cell Biol., 8:67-113, 1992.
24. Howard et al., "Penetration of hard substrates by a fungus employing enormous turgor pressures." Proc. Natl. Acad. Sci. USA, 88:11281-11284, 1991.
25. Jacobs et al., "An *Arabidopsis* callose synthase, GSL5, is required for wound and papillary callose formation." Plant Cell, 15:2503-2513, 2003.
26. Ketchum et al., "The yeast a-factor transporter Step 6p, a member of the ABC superfamily, couples ATP hydrolysis to pheromone export." J. Biol. Chem., 276:29007-29011, 2001.
27. Kimura et al., "Effects of P-glycoprotein inhibitors on trans-epithelial transport of cadmium in cultured renal epithelial cells, LLC-PK1 and LLC-GA5-COL150." Toxicology, 208:123-132, 2005.
28. Kodama et al., Sakuranetin, a flavonone phytoalexin from ultraviolet-irradiated rice leaves." Phytochemistry, 31:3807-3809, 1992.
29. Kolaczkowski et al., "In vivo characterization of the drug resistance profile of the major ABC transporters and other components of the yeast pleiotropic drug resistance network. Microb." Drug Resist., 4:143-158, 1998.
30. Kumar et al., "MEGA 3: Integrated Software for Molecular Evolutionary Genetics Analysis and Sequence Alignment." Briefings in Bioinformatics, 5:150-163, 2004.
31. Lee et al., "Functional analysis of all nonribosomal peptide synthetases in *Cochliobolus heterostrophus* reveals a factor, NPS6, involved in virulence and resistance to oxidative stress." Eukaryot. Cell, 4:545-555, 2005.
32. Lee et al., "A novel ABC transporter gene ABC2 involved in multidrug susceptibility but not pathogenicity in rice blast fungus, *Magnaporthe grisea*." Pestic. Biochem. Physiol., 81:13-23, 2005.
33. Lev et al., "Activation of an AP1-Like Transcription Factor of the Maize Pathogen *Cochliobolus heterostrophus* in Response to Oxidative Stress and Plant Signal." Eukaryotic Cell, 4:443-454, 2005.
34. Liu et al., "Efficient isolation and mapping of *Arabidopsis thaliana* T-DNA insert junctions by thermal asymmetric interlaced PCR." Plant J., 8:457-463, 1995.
35. Michaelis and Berkower, "Sequence comparison of yeast ATP-binding cassette proteins." Cold Spring Harbor Symp Quant. Biol. LX, 291-307, 1995.
36. Moreno et al., "Molecular genetic analysis of fission yeast *Schizosaccharomyces pombe*." Methods Enzymol., 194:795-823, 1991.
37. Naqvi et al., "Identification of RAPD markers linked to a major gene for blast resistance in rice." Mol. Breed., 1:341-348, 1995.
38. Nishi et al., "A leptomycin B resistance gene of *Schizosaccharomyces pombe* encodes a protein similar to the mammalian P-glycoproteins." Mol. Microbiol., 6:761-769, 1992.
39. Nomura and Takagi, "Role of the yeast acetyltransferase Mpr1 in oxidative stress: regulation of oxygen reactive species caused by a toxic proline catabolism intermediate." Proc. Natl. Acad. Sci. USA, 101:12616-12621, 2004.
40. Osbourn, "Preformed Antimicrobial Compounds and Plant Defense against Fungal Attack." Plant Cell, 8:1821-1831, 1996.
41. Ou, "*Rice Diseases*." Commonwealth Mycological Institute, Surrey, 1985.
42. Park et al., "Independent genetic mechanisms mediate turgor generation and penetration peg formation during plant infection in the rice blast fungus." Mol. Microbiol., 53:1695-1707, 2004.
43. Ramos-Pamplona and Naqvi, "Host invasion during rice-blast disease requires carnitine-dependent transport of peroxisomal acetyl-CoA." Mol. Microbiol., 61(1):61-75, 2006.
44. Routledge et al., "*Magnaporthe grisea* interactions with the model grass *Brachypodium distachyon* closely resemble those with rice (*Oryza sativa*)." Mol. Plant Path., 5:253-265, 2005.
45. Saier and Paulsen, "Phylogeny of multidrug transporters." Semin. Cell Dev. Biol., 12:205-213, 2001.
46. Sambrook et al., "Molecular Cloning: A Laboratory Manual." Cold Spring Harbor, N.Y.: Cold Spring Harbor Laboratory Press, 1989.
47. Soundararajan et al., "Woronin body function in *Magnaporthe grisea* is essential for efficient pathogenesis and for survival during nitrogen starvation stress." Plant Cell, 16:1564-1574, 2004.
48. Stergiopoulos et al., "The ABC transporter MgAtr4 is a virulence factor of *Mycosphaerella graminicola* that affects colonization of substomatal cavities in wheat leaves." Mol. Plant-Microbe Interact., 16:689-698, 2003.
49. Talbot, "On the trail of a cereal killer: Exploring the biology of *Magnaporthe grisea*." Annu. Rev. Microbiol., 57:177-202, 2003.
50. Thompson et al., "CLUSTAL W: improving the sensitivity of progressive multiple sequence alignment through sequence weighting, positions-specific gap penalties and weight matrix choice." Nucl. Acids Res., 22:4673-4680, 1994.
51. Tobin et al., "Genes encoding multiple drug resistance-like proteins in *Aspergillus fumigatus* and *Aspergillus flavus*." Gene, 200:11-23, 1997.
52. Uhr et al., "Penetration of endogenous steroid hormones corticosterone, cortisol, aldosterone and progesterone into the brain is enhanced in mice deficient for both mdr1a and mdr1b P-glycoproteins." J. Neuroendocrinol., 14:753-759, 2002.
53. Urban et al., "An ATP-driven efflux pump is a novel pathogenicity factor in rice blast disease." EMBO J., 18:512-521, 1999.
54. Valent, "Rice blast as a model system for plant pathology." Phytopathology, 80:33-36, 1990.
55. Valent et al., "*Magnaporthe grisea* genes for pathogenicity and virulence identified through a series of backcrosses." Genetics, 127:87-101, 1991.

56. Veneault-Fourrey et al., "Autophagic fungal cell death is necessary for infection by the rice blast fungus." Science, 312:580-583, 2006.
57. Vermeulen et al., "The ABC transporter BcatrB from *Botrytis cinerea* is a determinant of the activity of the phenylpyrrole fungicide fludioxonil." Pest Manag. Sci. 57:393-402, 2001.
58. Vogel and Somerville, "Isolation and characterization of powdery mildew-resistant *Arabidopsis* mutants." Proc. Natl. Acad. Sci. USA, 97:1897-1902, 2000.
59. Zwiers et al., "ABC transporters of the wheat pathogen *Mycosphaerella graminicola* function as protectants against biotic and xenobiotic toxic compounds." Mol. Genet. Genomics, 269:499-507, 2003.

The invention claimed is:

1. An isolated nucleic acid encoding the protein-coding region of the *Magnaporthe grisea* fungal abc3 gene, which is SEQ ID NO: I, wherein the encoded ABC3 protein is required for the successful entry of the fungus into host tissue.

2. An isolated nucleic acid encoding the protein-coding region of the fungal abc3 gene corresponding to the nucleic acid of claim 1, wherein said fungal abc3 gene is selected from the group consisting of the abc3 gene of *Magnaporthe* species, *Aspergillus* species, *Ustilago* species and *Fusarium* species, wherein said nucleic acid encodes an ABC3 protein that is required for the successful entry of the fungus into host tissue.

3. An isolated *Magnaporthe grisea* fungal ABC3 protein which is SEQ ID NO: 2, wherein said ABC3 protein is required for the successful entry of the fungus into host tissue.

4. An isolated nucleic acid that encodes the ABC3 protein of claim 3.

5. A method of rendering a plant pathogenic fungal species selected from the group consisting of *Magnaporthe* species, *Aspergillus* species, *Ustilago* species and *Fusarium* species non-pathogenic to a plant, which comprises inhibiting expression of fungal ABC3 protein corresponding to the fungal ABC3 protein of claim 3, said method comprising using a replacement plasmid vector.

6. The method of claim 5 wherein said plant pathogenic fungal species is *Magnaporthe* species.

7. The method of claim 6 wherein said *Magnaporthe* species is *Magnaporthe grisea*.

8. The method of claim 5 wherein said replacement plasmid vector is pFGLabcKO.

* * * * *

SEQUENCE LISTING

```
<160> NUMBER OF SEQ ID NOS: 30

<210> SEQ ID NO 1
<211> LENGTH: 4565
<212> TYPE: DNA
<213> ORGANISM: Magnaporthe grisea

<400> SEQUENCE: 1
atgacagcgg cgacacccgc tgatggggag aagggcttca agctcaaccc gaaacatctg      60
ttggcgatac acaacttcaa ggttagtact agtctggact aaaaaaaaac ttgcaccagc     120
taacgatgtt atagaggatc ttgacatatg gcacaaaatg ggacaagata gtgttgggag     180
tttcaacggt atcgtcggtg gccacaggcc tgacgatacc cttgatggtt gtcgtctttg     240
ccaggctcat tggcatattt accgattttt atcgccaggg gtcgaccgtg actggcgccc     300
agttcagcag tcaggttaac caatgtgtat acaacatcat atacctcttc gtggccagga     360
ttatattttc ctacatctcc aatgtaagac tctctcgtcc tctcgagtat gcaatggcta     420
acaaccacag cttggctttc gcatgttctc actgcgcatc tcctccacca tccggacggt     480
ttaccttcgc tctttattcg cccttcccat ctcagtcatc gatgcaatcc cagccggaca     540
aaccgccgcc atagtcaccg gcacggcaag tctgctgcag gtcggcatat ccgaaaagct     600
gggcggtggc atcgccagct tggccagtgt cgcttctagc gtcgttgttg ccctcgtctt     660
caactggcta ctaacttttg tgaccattgc tgggttggct ttcattgcca tcgtgtacgt     720
cattttcacc cctctggttg gcaaaaaggc tctcgaggtc cacgaggccg atgtcaaggc     780
atccagcatt gccacagagg cctttacttc ggtccgcatg ctggcagcat gtggtgccga     840
gaacaaggtc gcgcgccgtt atgcagtcca tgtggatgag tcgtatcaaa agggcttgcg     900
aatggcatgg cttgtgggag tccagcagat gtttggtaag ttcccgcctc ctccttgatt     960
tagggatata ctgaccctga tagtcttctt tggcgtatac gcgacctttg ctctcgcctt    1020
ttactttgcc tttcgcatgt acaacaccag catcaccacg acccccgagg atcttatagt    1080
gtatgtatac ccatacctc atcgacaacc aaagctaact tccacagcgt ccttctctgc    1140
gtcatgatga tggcaacctc gatcggccag atcacagccc ccttggccgc tgcgcaacag    1200
gcagcagagg cttgtggcat cttccatacc atcatcgact ttccgaagcc ggtctacgga    1260
tctgccagag gagagcatga agtccgggca gatggcgaca ttgtcctcat gaatgtcaac    1320
tttgcttacc cgacccgccc agaggtcaag gttctcgata atctatctct ggtgttccct    1380
gcgggcaagg ttactgcgat cgtgggtccg tctggttcgg gcaaatccac catcgttggc    1440
atcctggagc gctggtacga gttcaatggt gatccggtct taaacccact ggtaagaaac    1500
cccaaccctc aagccttctc agctaacaag aagcaggtcc tctaccttcg caacggattt    1560
gtatctgtag gcggacgcct tctcaccgaa atcgacgtca aatggtggcg caaccagata    1620
ggcctggttc agcaagacaa tgtgctcttc aacacgacaa tttacaaaaa cgtcgagcat    1680
gggctgatcg gcacgctgtg ggagcatgag agcgacgaga aaaaggccat gctgattgag    1740
```

```
actgcatgcc gggatgcgtt tgccgacgag ttcatcaacc gtctcccaga cgtaagtatc    1800
tcactgtatc cccatgatga tctcattact gacgcacagg cagcgctacc aaacaaccgt    1860
gggtgaatca ggaatcaagc tcagtggagg tcaacgtcaa cgtctcgcca tcgcgcgcgc    1920
aatcgtcaag cagcccaaga tcctcatcct cgacgaggca acctccgcca tcgacgtgcg    1980
cagcgaacaa atcgttcaag ccgcccttga gcgggccagc cgtggacgca ccaccgtcgt    2040
gattgcccac cgtctcggca ctgtcaaaaa ggccgacaag atcatcgtgc tgagcaaagg    2100
ccaggtggtg caggagggca cgcacgacga gctgcggagg caaggggta gtgcgtacta     2160 catgctggcc aatgctcaaa gcctaaacgt ccgtcggcgc tcgagcagaa tgagcatcga    2220
ccagactccg gacgaagagg atgacagcgg ttattttagg acgacgtcga tgcacgatgg    2280
cgattctgac cacacggccc actcttccaa ctatggatcg gatgaagagg acgacttcat    2340
catggagagg cctagggtgc gtgctcgtga cgatgtgggt gtggagatgt cgaccagtac    2400
catccacacc gcgcatactc ccgtgtccga tggcccgcca gatgacgccg caaagatcca    2460
ggtggtcgag attcaagacc actggcttgg tggtttcgcc gaactgttgg cggagcaagg    2520
atcgaggtgg aagctgtatt ttgtcatcat cataggagct attggagcag gtggtaagtt    2580
gatcttgatc caatgctagg tggcgtccac tgacaaccaa cagcaagcac accggtgcaa    2640
gcatacctct tcgcaactct cctcaacctc ttttccttca gaggtccaca ggtcaaccaa    2700
ctcgccaatt tcttttgtct catgttcgtg gtgctggcag cgggcgttgg catcagtcat    2760
ttgttcctag gatggtcgac gacgcgactg ggtttcggct tgacccgctt ctaccgaaag    2820
gagtacttca agaacatgat cagccgaccg gcgtccttct tcgacgagga ggaccacaca    2880
gtgggctcgt tgacggctag gttggctaca gacccaacgc agctgcagca gctcctcggc    2940
gttaacatgg catttgtgct cgtgtccatt ttcaacgtca tcgggtgttg tatcgtcggc    3000
ttcgtgtttg gatggaaatt gacaatcgtg tctttggcgt cgacaatgcc catcatcgtg    3060
gttgctatgg cctatcgcgt gcggcatgag gtccgccttg aggctgaagc aagcaaggtt    3120
ttcgctgaag gcgcccgatt cgcatccgaa agcatcgctg cgatccggac cgtgtccagc    3180
ttgaccatgg aagacggcgt cggaaccaga tatgaggagc tgttgaacaa acacgtccgt    3240
caggctttca gcaaggccag gtggtcgctg ctgttgtttt cctttagtga cagtatttca    3300
tttctctgca tggctttcgt cttgtggtaa gtactgtcct gctgcactgg gcaatcgcga    3360
atgctgactt tttcaggtac ggtggtcgac tgctggccag tcgggagtac agccccttcc    3420
aatatggtga gttcagtctc tctgattttg ccgtgctctt actaacatac gatagtgatt    3480
gtgtacattg ccgttgttca ggtaagaatc aaaccatcac gtgcgacagc aggactttac    3540
taactccaac agggtgcaat gagtgccgga caatggttga gcttcggtcc cagtgagtaa    3600 cccccccatgt gcactccaca gcgatgcgtg ctaacttgaa cagatatcgc ccatgctacc    3660
gccgcagccg atcgggttct tgatatgcga gaagccgatg acgaactcga ccgtggcttg    3720
cctttaatcg accccaacga agatgccatg ctggaagaga agaaggtgc cgaagtagag     3780 ctgcgcgacg tgtggttcag ctaccccgacc cgacccggaa caatcctcaa aggcctagac    3840
atcaaggttg aacgtggaca gtttgctgcc atcgttggcc catccggttc aggaaagacg    3900
acagtcatct ctctgttgga gcgcttctat ggcgctgatt cgggccaggt cctgtacaac    3960
ggccacgatg tgctggacct cgagccttcg gcgtaccggt ccaacgtgtc gctcgtggca    4020
caggagccac atcttctcag tgggtcgatg cgcgataatg tactgctcgg cattgaagac    4080
gagtcgaccg tggttcatgc cgacatctac gccgcgtgtc aagaggcagg actgcacgac    4140
```

-continued

```
ttcatctcgt cgctacccga agggtattcc accgaagtcg gagcacgagg tgtggctctt   4200
tctggaggcc agaagcagcg tctttccatc gcccgtgctt tgatccgccg tccggctttg   4260
ttgctcctcg atgaggcaac cagtgccctt gacagcgaga cggagagggc ggtgcaggag   4320
acctttgaag ccaccaaagg cagcagaaca atgattgttg tcgcacatcg tttggcaaca   4380
gtcaaaaacg cagatgtcat tttcgtcatg gcggacggaa aggtcattga gcagggcgac   4440
catgtctcct tgctggaaag gagaggagtc tactatgaaa tggtaagttt tcccgtgcgt   4500
gtccaacctg ggtcaatgct aactgccggg tgtaacagtg tcaatctcaa gcattggaca   4560
ggtga                                                               4565
```

```

<210> SEQ ID NO 2
<211> LENGTH: 1321
<212> TYPE: PRT
<213> ORGANISM: Magnaporthe grisea

<400> SEQUENCE: 2

Met Thr Ala Ala Thr Pro Ala Asp Gly Glu Lys Gly Phe Lys Leu Asn
1               5                   10                  15

Pro Lys His Leu Leu Ala Ile His Asn Phe Lys Arg Ile Leu Thr Tyr
            20                  25                  30

Gly Thr Lys Trp Asp Lys Ile Val Leu Gly Val Ser Thr Val Ser Ser
        35                  40                  45

Val Ala Thr Gly Leu Thr Ile Pro Leu Met Val Val Val Phe Ala Arg
    50                  55                  60

Leu Ile Gly Ile Phe Thr Asp Phe Tyr Arg Gln Gly Ser Thr Val Thr
65                  70                  75                  80

Gly Ala Gln Phe Ser Ser Gln Val Asn Gln Cys Val Tyr Asn Ile Ile
                85                  90                  95

Tyr Leu Phe Val Ala Arg Ile Ile Phe Ser Tyr Ile Ser Asn Leu Gly
            100                 105                 110

Phe Arg Met Phe Ser Leu Arg Ile Ser Ser Thr Ile Arg Thr Val Tyr
        115                 120                 125

Leu Arg Ser Leu Phe Ala Leu Pro Ile Ser Val Ile Asp Ala Ile Pro
    130                 135                 140

Ala Gly Gln Thr Ala Ala Ile Val Thr Gly Thr Ala Ser Leu Leu Gln
145                 150                 155                 160

Val Gly Ile Ser Glu Lys Leu Gly Gly Gly Ile Ala Ser Leu Ala Ser
                165                 170                 175

Val Ala Ser Ser Val Val Val Ala Leu Val Phe Asn Trp Leu Leu Thr
            180                 185                 190

Phe Val Thr Ile Ala Gly Leu Ala Phe Ile Ala Ile Val Tyr Val Ile
        195                 200                 205

Phe Thr Pro Leu Val Gly Lys Lys Ala Leu Glu Val His Glu Ala Asp
    210                 215                 220

Val Lys Ala Ser Ser Ile Ala Thr Glu Ala Phe Thr Ser Val Arg Met
225                 230                 235                 240

Leu Ala Ala Cys Gly Ala Glu Asn Lys Val Ala Arg Arg Tyr Ala Val
                245                 250                 255

His Val Asp Glu Ser Tyr Gln Lys Gly Leu Arg Met Ala Trp Leu Val
            260                 265                 270

Gly Val Gln Gln Met Phe Val Phe Phe Gly Val Tyr Ala Thr Phe Ala
        275                 280                 285

Leu Ala Phe Tyr Phe Ala Phe Arg Met Tyr Asn Thr Ser Ile Thr Thr
    290                 295                 300
```

```
Thr Pro Glu Asp Leu Ile Val Val Leu Leu Cys Val Met Met Met Ala
305                 310                 315                 320

Thr Ser Ile Gly Gln Ile Thr Ala Pro Leu Ala Ala Gln Gln Ala
        325                 330                 335

Ala Glu Ala Cys Gly Ile Phe His Thr Ile Ile Asp Phe Pro Lys Pro
            340                 345                 350

Val Tyr Gly Ser Ala Arg Gly Glu His Glu Val Arg Ala Asp Gly Asp
                355                 360                 365

Ile Val Leu Met Asn Val Asn Phe Ala Tyr Pro Thr Arg Pro Glu Val
        370                 375                 380

Lys Val Leu Asp Asn Leu Ser Leu Val Phe Pro Ala Gly Lys Val Thr
385                 390                 395                 400

Ala Ile Val Gly Pro Ser Gly Ser Gly Lys Ser Thr Val Gly Ile
            405                 410                 415

Leu Glu Arg Trp Tyr Glu Phe Asn Gly Asp Pro Val Leu Asn Pro Leu
                420                 425                 430

Val Leu Tyr Leu Arg Asn Gly Phe Val Ser Val Gly Arg Leu Leu
        435                 440                 445

Thr Glu Ile Asp Val Lys Trp Trp Arg Asn Gln Ile Gly Leu Val Gln
450                 455                 460

Gln Asp Asn Val Leu Phe Asn Thr Thr Ile Tyr Lys Asn Val Glu His
465                 470                 475                 480

Gly Leu Ile Gly Thr Leu Trp Glu His Glu Ser Asp Glu Lys Lys Ala
            485                 490                 495

Met Leu Ile Glu Thr Ala Cys Arg Asp Ala Phe Ala Asp Glu Phe Ile
                500                 505                 510

Asn Arg Leu Pro Asp Arg Tyr Gln Thr Thr Val Gly Glu Ser Gly Ile
        515                 520                 525

Lys Leu Ser Gly Gly Gln Arg Gln Arg Leu Ala Ile Ala Arg Ala Ile
530                 535                 540

Val Lys Gln Pro Lys Ile Leu Ile Leu Asp Glu Ala Thr Ser Ala Ile
545                 550                 555                 560

Asp Val Arg Ser Glu Gln Ile Val Gln Ala Ala Leu Glu Arg Ala Ser
            565                 570                 575

Arg Gly Arg Thr Thr Val Val Ile Ala His Arg Leu Gly Thr Val Lys
                580                 585                 590

Lys Ala Asp Lys Ile Ile Val Leu Ser Lys Gly Gln Val Val Gln Glu
        595                 600                 605

Gly Thr His Asp Glu Leu Arg Arg Gln Arg Gly Ser Ala Tyr Tyr Met
610                 615                 620

Leu Ala Asn Ala Gln Ser Leu Asn Val Arg Arg Ser Ser Arg Met
625                 630                 635                 640

Ser Ile Asp Gln Thr Pro Asp Glu Glu Asp Ser Gly Tyr Phe Arg
            645                 650                 655

Thr Thr Ser Met His Asp Gly Asp Ser Asp His Thr Ala His Ser Ser
                660                 665                 670

Asn Tyr Gly Ser Asp Glu Glu Asp Phe Ile Met Glu Arg Pro Arg
        675                 680                 685

Val Arg Ala Arg Asp Asp Val Gly Val Glu Met Ser Thr Ser Thr Ile
        690                 695                 700

His Thr Ala His Thr Pro Val Ser Asp Gly Pro Pro Asp Asp Ala Ala
705                 710                 715                 720

Lys Ile Gln Val Val Glu Ile Gln Asp His Trp Leu Gly Gly Phe Ala
```

-continued

```
                725                 730                 735
Glu Leu Leu Ala Glu Gln Gly Ser Arg Trp Lys Leu Tyr Phe Val Ile
            740                 745                 750
Ile Ile Gly Ala Ile Gly Ala Gly Ala Ser Thr Pro Val Gln Ala Tyr
            755                 760                 765
Leu Phe Ala Thr Leu Leu Asn Leu Phe Ser Phe Arg Gly Pro Gln Val
            770                 775                 780
Asn Gln Leu Ala Asn Phe Phe Cys Leu Met Phe Val Val Leu Ala Ala
785                 790                 795                 800
Gly Val Gly Ile Ser His Leu Phe Leu Gly Trp Ser Thr Thr Arg Leu
                805                 810                 815
Gly Phe Gly Leu Thr Arg Phe Tyr Arg Lys Glu Tyr Phe Lys Asn Met
                820                 825                 830
Ile Ser Arg Pro Ala Ser Phe Asp Glu Glu Asp His Thr Val Gly
                835                 840                 845
Ser Leu Thr Ala Arg Leu Ala Thr Asp Pro Thr Gln Leu Gln Gln Leu
            850                 855                 860
Leu Gly Val Asn Met Ala Phe Val Leu Val Ser Ile Phe Asn Val Ile
865                 870                 875                 880
Gly Cys Cys Ile Val Gly Phe Val Phe Gly Trp Lys Leu Thr Ile Val
                885                 890                 895
Ser Leu Ala Ser Thr Met Pro Ile Ile Val Val Ala Met Ala Tyr Arg
            900                 905                 910
Val Arg His Glu Val Arg Leu Glu Ala Glu Ala Ser Lys Val Phe Ala
            915                 920                 925
Glu Gly Ala Arg Phe Ala Ser Glu Ser Ile Ala Ala Ile Arg Thr Val
            930                 935                 940
Ser Ser Leu Thr Met Glu Asp Gly Val Gly Thr Arg Tyr Glu Glu Leu
945                 950                 955                 960
Leu Asn Lys His Val Arg Gln Ala Phe Ser Lys Ala Arg Trp Ser Leu
                965                 970                 975
Leu Leu Phe Ser Phe Ser Asp Ser Ile Ser Phe Leu Cys Met Ala Phe
            980                 985                 990
Val Leu Trp Tyr Gly Gly Arg Leu  Leu Ala Ser Arg Glu  Tyr Ser Pro
            995                 1000                1005
Phe Gln  Tyr Val Ile Val Tyr  Ile Ala Val Val Gln  Gly Ala Met
    1010                1015                1020
Ser Ala  Gly Gln Trp Leu Ser  Phe Gly Pro Asn Ile  Ala His Ala
    1025                1030                1035
Thr Ala  Ala Ala Asp Arg Val  Leu Asp Met Arg Glu  Ala Asp Asp
    1040                1045                1050
Glu Leu  Asp Arg Gly Leu Pro  Leu Ile Asp Pro Asn  Glu Asp Ala
    1055                1060                1065
Met Leu  Glu Glu Lys Glu Gly  Ala Glu Val Glu Leu  Arg Asp Val
    1070                1075                1080
Trp Phe  Ser Tyr Pro Thr Arg  Pro Gly Thr Ile Leu  Lys Gly Leu
    1085                1090                1095
Asp Ile  Lys Val Glu Arg Gly  Gln Phe Ala Ala Ile  Val Gly Pro
    1100                1105                1110
Ser Gly  Ser Gly Lys Thr Thr  Val Ile Ser Leu Leu  Glu Arg Phe
    1115                1120                1125
Tyr Gly  Ala Asp Ser Gly Gln  Val Leu Tyr Asn Gly  His Asp Val
    1130                1135                1140
```

```
Leu Asp Leu Glu Pro Ser Ala Tyr Arg Ser Asn Val Ser Leu Val
1145                1150                1155

Ala Gln Glu Pro His Leu Leu Ser Gly Ser Met Arg Asp Asn Val
1160                1165                1170

Leu Leu Gly Ile Glu Asp Glu Ser Thr Val Val His Ala Asp Ile
1175                1180                1185

Tyr Ala Ala Cys Gln Glu Ala Gly Leu His Asp Phe Ile Ser Ser
1190                1195                1200

Leu Pro Glu Gly Tyr Ser Thr Glu Val Gly Ala Arg Gly Val Ala
1205                1210                1215

Leu Ser Gly Gly Gln Lys Gln Arg Leu Ser Ile Ala Arg Ala Leu
1220                1225                1230

Ile Arg Arg Pro Ala Leu Leu Leu Leu Asp Glu Ala Thr Ser Ala
1235                1240                1245

Leu Asp Ser Glu Thr Glu Arg Ala Val Gln Glu Thr Phe Glu Ala
1250                1255                1260

Thr Lys Gly Ser Arg Thr Met Ile Val Val Ala His Arg Leu Ala
1265                1270                1275

Thr Val Lys Asn Ala Asp Val Ile Phe Val Met Ala Asp Gly Lys
1280                1285                1290

Val Ile Glu Gln Gly Asp His Val Ser Leu Leu Glu Arg Arg Gly
1295                1300                1305

Val Tyr Tyr Glu Met Cys Gln Ser Gln Ala Leu Asp Arg
1310                1315                1320

<210> SEQ ID NO 3
<211> LENGTH: 26
<212> TYPE: DNA
<213> ORGANISM: Artificial
<220> FEATURE:
<223> OTHER INFORMATION: Primer for rapid amplification of complementary
      DNA

<400> SEQUENCE: 3
cggaaccaga tatgaggagc tgttga                                       26

<210> SEQ ID NO 4
<211> LENGTH: 39
<212> TYPE: DNA
<213> ORGANISM: Artificial
<220> FEATURE:
<223> OTHER INFORMATION: Primer for rapid amplification of complementary
      DNA

<400> SEQUENCE: 4
gaccacgcgt atcgatgtcg actttttttt tttttttc                          39

<210> SEQ ID NO 5
<211> LENGTH: 22
<212> TYPE: DNA
<213> ORGANISM: Artificial
<220> FEATURE:
<223> OTHER INFORMATION: Primer for rapid amplification of complementary
      DNA

<400> SEQUENCE: 5
gaccacgcgt atcgatgtcg ac                                           22

<210> SEQ ID NO 6
<211> LENGTH: 20
<212> TYPE: DNA
<213> ORGANISM: Artificial
```

-continued

```
<220> FEATURE:
<223> OTHER INFORMATION: Primer for rapid amplification of complementary
      DNA

<400> SEQUENCE: 6
tgatgctggt gttgtacatg                                              20

<210> SEQ ID NO 7
<211> LENGTH: 21
<212> TYPE: DNA
<213> ORGANISM: Artificial
<220> FEATURE:
<223> OTHER INFORMATION: Semi-quantitative RT-PCR primer

<400> SEQUENCE: 7
caagccgata gacacactga c                                            21

<210> SEQ ID NO 8
<211> LENGTH: 20
<212> TYPE: DNA
<213> ORGANISM: Artificial
<220> FEATURE:
<223> OTHER INFORMATION: Semi-quantitative RT-PCR primer

<400> SEQUENCE: 8
gaactaatcg tcctcagtgc                                              20

<210> SEQ ID NO 9
<211> LENGTH: 26
<212> TYPE: DNA
<213> ORGANISM: Artificial
<220> FEATURE:
<223> OTHER INFORMATION: Semi-quantitative RT-PCR primer

<400> SEQUENCE: 9
aaacaactgg gccaagggtc actaca                                       26

<210> SEQ ID NO 10
<211> LENGTH: 26
<212> TYPE: DNA
<213> ORGANISM: Artificial
<220> FEATURE:
<223> OTHER INFORMATION: Semi-quantitative RT-PCR primer

<400> SEQUENCE: 10
ccgatgaaag tcgacgacat cttgag                                       26

<210> SEQ ID NO 11
<211> LENGTH: 26
<212> TYPE: DNA
<213> ORGANISM: Artificial
<220> FEATURE:
<223> OTHER INFORMATION: Semi-quantitative RT-PCR primer

<400> SEQUENCE: 11
cgttatgcag tccatgtgga tgagtc                                       26

<210> SEQ ID NO 12
<211> LENGTH: 26
<212> TYPE: DNA
<213> ORGANISM: Artificial
<220> FEATURE:
<223> OTHER INFORMATION: Semi-quantitative RT-PCR primer

<400> SEQUENCE: 12
acgatttgtt cgctgcgcac gtcgat                                       26
```

```
<210> SEQ ID NO 13
<211> LENGTH: 22
<212> TYPE: DNA
<213> ORGANISM: Artificial
<220> FEATURE:
<223> OTHER INFORMATION: Semi-quantitative RT-PCR primer

<400> SEQUENCE: 13
cgcagagcaa caacagtaaa gc                                              22

<210> SEQ ID NO 14
<211> LENGTH: 20
<212> TYPE: DNA
<213> ORGANISM: Artificial
<220> FEATURE:
<223> OTHER INFORMATION: Semi-quantitative RT-PCR primer

<400> SEQUENCE: 14
acgcctatta ttggttggcg                                                 20

<210> SEQ ID NO 15
<211> LENGTH: 20
<212> TYPE: DNA
<213> ORGANISM: Artificial
<220> FEATURE:
<223> OTHER INFORMATION: Semi-quantitative RT-PCR primer

<400> SEQUENCE: 15
ctgtctttcc cagcattgta                                                 20

<210> SEQ ID NO 16
<211> LENGTH: 20
<212> TYPE: DNA
<213> ORGANISM: Artificial
<220> FEATURE:
<223> OTHER INFORMATION: Semi-quantitative RT-PCR primer

<400> SEQUENCE: 16
atcctcggtg cgacacggag                                                 20

<210> SEQ ID NO 17
<211> LENGTH: 24
<212> TYPE: DNA
<213> ORGANISM: Artificial
<220> FEATURE:
<223> OTHER INFORMATION: Primer for quantitative RT-PCR

<400> SEQUENCE: 17
atggaggtat ccaagctggc catt                                            24

<210> SEQ ID NO 18
<211> LENGTH: 24
<212> TYPE: DNA
<213> ORGANISM: Artificial
<220> FEATURE:
<223> OTHER INFORMATION: Primer for quantitative RT-PCR primer

<400> SEQUENCE: 18
gtaaggcctc tgtccgacga agtt                                            24

<210> SEQ ID NO 19
<211> LENGTH: 27
<212> TYPE: DNA
<213> ORGANISM: Artificial
<220> FEATURE:
<223> OTHER INFORMATION: Primer for quantitative RT-PCR primer
```

-continued

```
<400> SEQUENCE: 19
tagtattgtt ggccgtcctc gccacac                                          27

<210> SEQ ID NO 20
<211> LENGTH: 27
<212> TYPE: DNA
<213> ORGANISM: Artificial
<220> FEATURE:
<223> OTHER INFORMATION: Primer for quantitative RT-PCR primer

<400> SEQUENCE: 20
gatggaatga tgaagcgcat atccttc                                          27

<210> SEQ ID NO 21
<211> LENGTH: 22
<212> TYPE: DNA
<213> ORGANISM: Artificial
<220> FEATURE:
<223> OTHER INFORMATION: Primer for quantitative RT-PCR primer

<400> SEQUENCE: 21
cgcagagcaa caacagtaaa gc                                               22

<210> SEQ ID NO 22
<211> LENGTH: 20
<212> TYPE: DNA
<213> ORGANISM: Artificial
<220> FEATURE:
<223> OTHER INFORMATION: Primer for quantitative RT-PCR primer

<400> SEQUENCE: 22
acgcctatta ttggttggcg                                                  20

<210> SEQ ID NO 23
<211> LENGTH: 20
<212> TYPE: DNA
<213> ORGANISM: Artificial
<220> FEATURE:
<223> OTHER INFORMATION: Primer for quantitative RT-PCR primer

<400> SEQUENCE: 23
ctgtctttcc cagcattgta                                                  20

<210> SEQ ID NO 24
<211> LENGTH: 20
<212> TYPE: DNA
<213> ORGANISM: Artificial
<220> FEATURE:
<223> OTHER INFORMATION: Primer for quantitative RT-PCR primer

<400> SEQUENCE: 24
atcctcggtg cgacacggag                                                  20

<210> SEQ ID NO 25
<211> LENGTH: 1321
<212> TYPE: PRT
<213> ORGANISM: Magnaporthe grisea

<400> SEQUENCE: 25

Met Thr Ala Ala Thr Pro Ala Asp Gly Glu Lys Gly Phe Lys Leu Asn
1               5                   10                  15

Pro Lys His Leu Leu Ala Ile His Asn Phe Lys Arg Ile Leu Thr Tyr
            20                  25                  30

Gly Thr Lys Trp Asp Lys Ile Val Leu Gly Val Ser Thr Val Ser Ser
        35                  40                  45
```

```
Val Ala Thr Gly Leu Thr Ile Pro Leu Met Val Val Phe Ala Arg
 50                  55                  60

Leu Ile Gly Ile Phe Thr Asp Phe Tyr Arg Gln Gly Ser Thr Val Thr
 65                  70                  75                  80

Gly Ala Gln Phe Ser Ser Gln Val Asn Gln Cys Val Tyr Asn Ile Ile
                 85                  90                  95

Tyr Leu Phe Val Ala Arg Ile Ile Phe Ser Tyr Ile Ser Asn Leu Gly
                100                 105                 110

Phe Arg Met Phe Ser Leu Arg Ile Ser Ser Thr Ile Arg Thr Val Tyr
            115                 120                 125

Leu Arg Ser Leu Phe Ala Leu Pro Ile Ser Val Ile Asp Ala Ile Pro
            130                 135                 140

Ala Gly Gln Thr Ala Ala Ile Val Thr Gly Thr Ala Ser Leu Leu Gln
145                 150                 155                 160

Val Gly Ile Ser Glu Lys Leu Gly Gly Ile Ala Ser Leu Ala Ser
                165                 170                 175

Val Ala Ser Ser Val Val Ala Leu Val Phe Asn Trp Leu Leu Thr
                180                 185                 190

Phe Val Thr Ile Ala Gly Leu Ala Phe Ile Ala Ile Val Tyr Val Ile
            195                 200                 205

Phe Thr Pro Leu Val Gly Lys Lys Ala Leu Glu Val His Glu Ala Asp
210                 215                 220

Val Lys Ala Ser Ser Ile Ala Thr Glu Ala Phe Thr Ser Val Arg Met
225                 230                 235                 240

Leu Ala Ala Cys Gly Ala Glu Asn Lys Val Ala Arg Arg Tyr Ala Val
                245                 250                 255

His Val Asp Glu Ser Tyr Gln Lys Gly Leu Arg Met Ala Trp Leu Val
                260                 265                 270

Gly Val Gln Gln Met Phe Val Phe Gly Val Tyr Ala Thr Phe Ala
            275                 280                 285

Leu Ala Phe Tyr Phe Ala Phe Arg Met Tyr Asn Thr Ser Ile Thr Thr
            290                 295                 300

Thr Pro Glu Asp Leu Ile Val Val Leu Leu Cys Val Met Met Met Ala
305                 310                 315                 320

Thr Ser Ile Gly Gln Ile Thr Ala Pro Leu Ala Ala Gln Gln Ala
                325                 330                 335

Ala Glu Ala Cys Gly Ile Phe His Thr Ile Asp Phe Pro Lys Pro
            340                 345                 350

Val Tyr Gly Ser Ala Arg Gly Glu His Glu Val Arg Ala Asp Gly Asp
                355                 360                 365

Ile Val Leu Met Asn Val Asn Phe Ala Tyr Pro Thr Arg Pro Glu Val
            370                 375                 380

Lys Val Leu Asp Asn Leu Ser Leu Val Phe Pro Ala Gly Lys Val Thr
385                 390                 395                 400

Ala Ile Val Gly Pro Ser Gly Ser Gly Lys Ser Thr Ile Val Gly Ile
                405                 410                 415

Leu Glu Arg Trp Tyr Glu Phe Asn Gly Asp Pro Val Leu Asn Pro Leu
            420                 425                 430

Val Leu Tyr Leu Arg Asn Gly Phe Val Ser Val Gly Arg Leu Leu
            435                 440                 445

Thr Glu Ile Asp Val Lys Trp Trp Arg Asn Gln Ile Gly Leu Val Gln
            450                 455                 460

Gln Asp Asn Val Leu Phe Asn Thr Thr Ile Tyr Lys Asn Val Glu His
```

-continued

```
            465                 470                 475                 480
        Gly Leu Ile Gly Thr Leu Trp Glu His Glu Ser Asp Glu Lys Lys Ala
                        485                 490                 495
        Met Leu Ile Glu Thr Ala Cys Arg Asp Ala Phe Ala Asp Glu Phe Ile
                        500                 505                 510
        Asn Arg Leu Pro Asp Arg Tyr Gln Thr Thr Val Gly Glu Ser Gly Ile
                        515                 520                 525
        Lys Leu Ser Gly Gly Gln Arg Gln Arg Leu Ala Ile Ala Arg Ala Ile
                        530                 535                 540
        Val Lys Gln Pro Lys Ile Leu Ile Leu Asp Glu Ala Thr Ser Ala Ile
        545                 550                 555                 560
        Asp Val Arg Ser Glu Gln Ile Val Gln Ala Ala Leu Glu Arg Ala Ser
                        565                 570                 575
        Arg Gly Arg Thr Thr Val Val Ile Ala His Arg Leu Gly Thr Val Lys
                        580                 585                 590
        Lys Ala Asp Lys Ile Ile Val Leu Ser Lys Gly Gln Val Val Gln Glu
                        595                 600                 605
        Gly Thr His Asp Glu Leu Arg Arg Gln Arg Gly Ser Ala Tyr Tyr Met
                        610                 615                 620
        Leu Ala Asn Ala Gln Ser Leu Asn Val Arg Arg Arg Ser Ser Arg Met
        625                 630                 635                 640
        Ser Ile Asp Gln Thr Pro Asp Glu Glu Asp Ser Gly Tyr Phe Arg
                        645                 650                 655
        Thr Thr Ser Met His Asp Gly Asp Ser Asp His Thr Ala His Ser Ser
                        660                 665                 670
        Asn Tyr Gly Ser Asp Glu Glu Asp Phe Ile Met Glu Arg Pro Arg
                        675                 680                 685
        Val Arg Ala Arg Asp Asp Val Gly Val Glu Met Ser Thr Ser Thr Ile
                        690                 695                 700
        His Thr Ala His Thr Pro Val Ser Asp Gly Pro Pro Asp Asp Ala Ala
        705                 710                 715                 720
        Lys Ile Gln Val Val Glu Ile Gln Asp His Trp Leu Gly Gly Phe Ala
                        725                 730                 735
        Glu Leu Leu Ala Glu Gln Gly Ser Arg Trp Lys Leu Tyr Phe Val Ile
                        740                 745                 750
        Ile Ile Gly Ala Ile Gly Ala Gly Ala Ser Thr Pro Val Gln Ala Tyr
                        755                 760                 765
        Leu Phe Ala Thr Leu Leu Asn Leu Phe Ser Phe Arg Gly Pro Gln Val
                        770                 775                 780
        Asn Gln Leu Ala Asn Phe Phe Cys Leu Met Phe Val Val Leu Ala Ala
        785                 790                 795                 800
        Gly Val Gly Ile Ser His Leu Phe Leu Gly Trp Ser Thr Thr Arg Leu
                        805                 810                 815
        Gly Phe Gly Leu Thr Arg Phe Tyr Arg Lys Glu Tyr Phe Lys Asn Met
                        820                 825                 830
        Ile Ser Arg Pro Ala Ser Phe Phe Asp Glu Glu Asp His Thr Val Gly
                        835                 840                 845
        Ser Leu Thr Ala Arg Leu Ala Thr Asp Pro Thr Gln Leu Gln Gln Leu
                        850                 855                 860
        Leu Gly Val Asn Met Ala Phe Val Leu Val Ser Ile Phe Asn Val Ile
        865                 870                 875                 880
        Gly Cys Cys Ile Val Gly Phe Val Phe Gly Trp Lys Leu Thr Ile Val
                        885                 890                 895
```

-continued

Ser Leu Ala Ser Thr Met Pro Ile Val Val Ala Met Ala Tyr Arg
            900                 905                 910

Val Arg His Glu Val Arg Leu Glu Ala Glu Ala Ser Lys Val Phe Ala
            915                 920                 925

Glu Gly Ala Arg Phe Ala Ser Glu Ser Ile Ala Ala Ile Arg Thr Val
        930                 935                 940

Ser Ser Leu Thr Met Glu Asp Gly Val Gly Thr Arg Tyr Glu Glu Leu
945                 950                 955                 960

Leu Asn Lys His Val Arg Gln Ala Phe Ser Lys Ala Arg Trp Ser Leu
                965                 970                 975

Leu Leu Phe Ser Phe Ser Asp Ser Ile Ser Phe Leu Cys Met Ala Phe
            980                 985                 990

Val Leu Trp Tyr Gly Gly Arg Leu Leu Ala Ser Arg Glu Tyr Ser Pro
            995                 1000                1005

Phe Gln Tyr Val Ile Val Tyr Ile Ala Val Val Gln Gly Ala Met
        1010                1015                1020

Ser Ala Gly Gln Trp Leu Ser Phe Gly Pro Asn Ile Ala His Ala
        1025                1030                1035

Thr Ala Ala Ala Asp Arg Val Leu Asp Met Arg Glu Ala Asp Asp
        1040                1045                1050

Glu Leu Asp Arg Gly Leu Pro Leu Ile Asp Pro Asn Glu Asp Ala
        1055                1060                1065

Met Leu Glu Glu Lys Glu Gly Ala Glu Val Glu Leu Arg Asp Val
        1070                1075                1080

Trp Phe Ser Tyr Pro Thr Arg Pro Gly Thr Ile Leu Lys Gly Leu
        1085                1090                1095

Asp Ile Lys Val Glu Arg Gly Gln Phe Ala Ala Ile Val Gly Pro
        1100                1105                1110

Ser Gly Ser Gly Lys Thr Thr Val Ile Ser Leu Leu Glu Arg Phe
        1115                1120                1125

Tyr Gly Ala Asp Ser Gly Gln Val Leu Tyr Asn Gly His Asp Val
        1130                1135                1140

Leu Asp Leu Glu Pro Ser Ala Tyr Arg Ser Asn Val Ser Leu Val
        1145                1150                1155

Ala Gln Glu Pro His Leu Leu Ser Gly Ser Met Arg Asp Asn Val
        1160                1165                1170

Leu Leu Gly Ile Glu Asp Glu Ser Thr Val Val His Ala Asp Ile
        1175                1180                1185

Tyr Ala Ala Cys Gln Glu Ala Gly Leu His Asp Phe Ile Ser Ser
        1190                1195                1200

Leu Pro Glu Gly Tyr Ser Thr Glu Val Gly Ala Arg Gly Val Ala
        1205                1210                1215

Leu Ser Gly Gly Gln Lys Gln Arg Leu Ser Ile Ala Arg Ala Leu
        1220                1225                1230

Ile Arg Arg Pro Ala Leu Leu Leu Leu Asp Glu Ala Thr Ser Ala
        1235                1240                1245

Leu Asp Ser Glu Thr Glu Arg Ala Val Gln Glu Thr Phe Glu Ala
        1250                1255                1260

Thr Lys Gly Ser Arg Thr Met Ile Val Val Ala His Arg Leu Ala
        1265                1270                1275

Thr Val Lys Asn Ala Asp Val Ile Phe Val Met Ala Asp Gly Lys
        1280                1285                1290

Val Ile Glu Gln Gly Asp His Val Ser Leu Leu Glu Arg Arg Gly
        1295                1300                1305

```
Val Tyr Tyr Glu Met Cys Gln Ser Gln Ala Leu Asp Arg
    1310            1315            1320

<210> SEQ ID NO 26
<211> LENGTH: 1290
<212> TYPE: PRT
<213> ORGANISM: Saccharomyces cerevisiae

<400> SEQUENCE: 26

Met Asn Phe Leu Ser Phe Lys Thr Thr Lys His Tyr His Ile Phe Arg
1               5                   10                  15

Tyr Val Asn Ile Arg Asn Asp Tyr Arg Leu Leu Met Ile Met Ile Ile
            20                  25                  30

Gly Thr Val Ala Thr Gly Leu Val Pro Ala Ile Thr Ser Ile Leu Thr
        35                  40                  45

Gly Arg Val Phe Asp Leu Leu Ser Val Phe Val Ala Asn Gly Ser His
    50                  55                  60

Gln Gly Leu Tyr Ser Gln Leu Val Gln Arg Ser Met Ala Val Met Ala
65              70                  75                  80

Leu Gly Ala Ala Ser Val Pro Val Met Trp Leu Ser Leu Thr Ser Trp
                85                  90                  95

Met His Ile Gly Glu Arg Gln Gly Phe Arg Ile Arg Ser Gln Ile Leu
            100                 105                 110

Glu Ala Tyr Leu Glu Glu Lys Pro Met Glu Trp Tyr Asp Asn Asn Glu
        115                 120                 125

Lys Leu Leu Gly Asp Phe Thr Gln Ile Asn Arg Cys Val Glu Glu Leu
    130                 135                 140

Arg Ser Ser Ser Ala Glu Ala Ser Ala Ile Thr Phe Gln Asn Leu Val
145                 150                 155                 160

Ala Ile Cys Ala Leu Leu Gly Thr Ser Phe Tyr Tyr Ser Trp Ser Leu
                165                 170                 175

Thr Leu Ile Ile Leu Cys Ser Ser Pro Ile Ile Thr Phe Phe Ala Val
            180                 185                 190

Val Phe Ser Arg Met Ile His Val Tyr Ser Glu Lys Glu Asn Ser Glu
        195                 200                 205

Thr Ser Lys Ala Ala Gln Leu Leu Thr Trp Ser Met Asn Ala Ala Gln
    210                 215                 220

Leu Val Arg Leu Tyr Cys Thr Gln Arg Leu Glu Arg Lys Lys Phe Lys
225                 230                 235                 240

Glu Ile Ile Leu Asn Cys Asn Thr Phe Phe Ile Lys Ser Cys Phe Phe
                245                 250                 255

Val Ala Asn Ala Gly Ile Leu Arg Phe Leu Thr Leu Thr Met Phe
            260                 265                 270

Val Gln Gly Phe Trp Phe Gly Ser Ala Met Ile Lys Lys Gly Lys Leu
        275                 280                 285

Asn Ile Asn Asp Val Ile Thr Cys Phe His Ser Cys Ile Met Leu Gly
    290                 295                 300

Ser Thr Leu Asn Asn Thr Leu His Gln Ile Val Val Leu Gln Lys Gly
305                 310                 315                 320

Gly Val Ala Met Glu Lys Ile Met Thr Leu Leu Lys Asp Gly Ser Lys
                325                 330                 335

Arg Asn Pro Leu Asn Lys Thr Val Ala His Gln Phe Pro Leu Asp Tyr
            340                 345                 350

Ala Thr Ser Asp Leu Thr Phe Ala Asn Val Ser Phe Ser Tyr Pro Ser
        355                 360                 365
```

```
Arg Pro Ser Glu Ala Val Leu Lys Asn Val Ser Leu Asn Phe Ser Ala
    370                 375                 380

Gly Gln Phe Thr Phe Ile Val Gly Lys Ser Gly Ser Gly Lys Ser Thr
385                 390                 395                 400

Leu Ser Asn Leu Leu Leu Arg Phe Tyr Asp Gly Tyr Asn Gly Ser Ile
                405                 410                 415

Ser Ile Asn Gly His Asn Ile Gln Thr Ile Asp Gln Lys Leu Leu Ile
            420                 425                 430

Glu Asn Ile Thr Val Val Glu Gln Arg Cys Thr Leu Phe Asn Asp Thr
        435                 440                 445

Leu Arg Lys Asn Ile Leu Leu Gly Ser Thr Asp Ser Val Arg Asn Ala
    450                 455                 460

Asp Cys Ser Thr Asn Glu Asn Arg His Leu Ile Lys Asp Ala Cys Gln
465                 470                 475                 480

Met Ala Leu Leu Asp Arg Phe Ile Leu Asp Leu Pro Asp Gly Leu Glu
                485                 490                 495

Thr Leu Ile Gly Thr Gly Gly Val Thr Leu Ser Gly Gly Gln Gln Gln
            500                 505                 510

Arg Val Ala Ile Ala Arg Ala Phe Ile Arg Asp Thr Pro Ile Leu Phe
        515                 520                 525

Leu Asp Glu Ala Val Ser Ala Leu Asp Ile Val His Arg Asn Leu Leu
    530                 535                 540

Met Lys Ala Ile Arg His Trp Arg Lys Gly Lys Thr Thr Ile Ile Leu
545                 550                 555                 560

Thr His Glu Leu Ser Gln Ile Glu Ser Asp Asp Tyr Leu Tyr Leu Met
                565                 570                 575

Lys Gly Glu Val Val Glu Ser Gly Thr Gln Ser Glu Leu Leu Ala
            580                 585                 590

Asp Pro Thr Thr Thr Phe Ser Thr Trp Tyr His Leu Gln Asn Asp Tyr
        595                 600                 605

Ser Asp Ala Lys Thr Ile Val Asp Thr Glu Thr Glu Lys Ser Ile
    610                 615                 620

His Thr Val Glu Ser Phe Asn Ser Gln Leu Glu Thr Pro Lys Leu Gly
625                 630                 635                 640

Ser Cys Leu Ser Asn Leu Gly Tyr Asp Glu Thr Asp Gln Leu Ser Phe
                645                 650                 655

Tyr Glu Ala Ile Tyr Gln Lys Arg Ser Asn Val Arg Thr Arg Arg Val
            660                 665                 670

Lys Val Glu Glu Glu Asn Ile Gly Tyr Ala Leu Lys Gln Gln Lys Asn
        675                 680                 685

Thr Glu Ser Ser Thr Gly Pro Gln Leu Leu Ser Ile Ile Gln Ile Ile
    690                 695                 700

Lys Arg Met Ile Lys Ser Ile Arg Tyr Lys Lys Ile Leu Ile Leu Gly
705                 710                 715                 720

Leu Leu Cys Ser Leu Ile Ala Gly Ala Thr Asn Pro Val Phe Ser Tyr
                725                 730                 735

Thr Phe Ser Phe Leu Leu Glu Gly Ile Val Pro Ser Thr Asp Gly Lys
            740                 745                 750

Thr Gly Ser Ser His Tyr Leu Ala Lys Trp Ser Leu Leu Val Leu Gly
        755                 760                 765

Val Ala Ala Ala Asp Gly Ile Phe Asn Phe Ala Lys Gly Phe Leu Leu
    770                 775                 780

Asp Cys Cys Ser Glu Tyr Trp Val Met Asp Leu Arg Asn Glu Val Met
```

```
              785                 790                 795                 800
Glu Lys Leu Thr Arg Lys Asn Met Asp Trp Phe Ser Gly Asn Asn
                    805                 810                 815
Lys Ala Ser Glu Ile Ser Ala Leu Val Leu Asn Asp Leu Arg Asp Leu
                820                 825                 830
Arg Ser Leu Val Ser Glu Phe Leu Ser Ala Met Thr Ser Phe Val Thr
            835                 840                 845
Val Ser Thr Ile Gly Leu Ile Trp Ala Leu Val Ser Gly Trp Lys Leu
        850                 855                 860
Ser Leu Val Cys Ile Ser Met Phe Pro Leu Ile Ile Phe Ser Ala
865                 870                 875                 880
Ile Tyr Gly Gly Ile Leu Gln Lys Cys Glu Thr Asp Tyr Lys Thr Ser
                885                 890                 895
Val Ala Gln Leu Glu Asn Cys Leu Tyr Gln Ile Val Thr Asn Ile Lys
                900                 905                 910
Thr Ile Lys Cys Leu Gln Ala Glu Phe His Phe Gln Leu Thr Tyr His
                915                 920                 925
Asp Leu Lys Ile Lys Met Gln Gln Ile Ala Ser Lys Arg Ala Ile Ala
            930                 935                 940
Thr Gly Phe Gly Ile Ser Met Thr Asn Met Ile Val Met Cys Ile Gln
945                 950                 955                 960
Ala Ile Ile Tyr Tyr Tyr Gly Leu Lys Leu Val Met Ile His Glu Tyr
                965                 970                 975
Thr Ser Lys Glu Met Phe Thr Thr Phe Thr Leu Leu Leu Phe Thr Ile
                980                 985                 990
Met Ser Cys Thr Ser Leu Val Ser  Gln Ile Pro Asp Ile  Ser Arg Gly
                995                1000                1005
Gln Arg Ala Ala Ser Trp Ile  Tyr Arg Ile Leu Asp  Glu Lys His
    1010                1015                1020
Asn Thr Leu Glu Val Glu Asn  Asn Asn Ala Arg Thr  Val Gly Ile
        1025                1030                1035
Ala Gly His Thr Tyr His Gly  Lys Glu Lys Lys Pro  Ile Val Ser
        1040                1045                1050
Ile Gln Asn Leu Thr Phe Ala  Tyr Pro Ser Ala Pro  Thr Ala Phe
        1055                1060                1065
Val Tyr Lys Asn Met Asn Phe  Asp Met Phe Cys Gly  Gln Thr Leu
        1070                1075                1080
Gly Ile Ile Gly Glu Ser Gly  Thr Gly Lys Ser Thr  Leu Val Leu
        1085                1090                1095
Leu Leu Thr Lys Leu Tyr Asn  Cys Glu Val Gly Lys  Ile Lys Ile
        1100                1105                1110
Asp Gly Thr Asp Val Asn Asp  Trp Asn Leu Thr Ser  Leu Arg Lys
        1115                1120                1125
Glu Ile Ser Val Val Glu Gln  Lys Pro Leu Leu Phe  Asn Gly Thr
        1130                1135                1140
Ile Arg Asp Asn Leu Thr Tyr  Gly Leu Gln Asp Glu  Ile Leu Glu
        1145                1150                1155
Ile Glu Met Tyr Asp Ala Leu  Lys Tyr Val Gly Ile  His Asp Phe
        1160                1165                1170
Val Ile Ser Ser Pro Gln Gly  Leu Asp Thr Arg Ile  Asp Thr Thr
        1175                1180                1185
Leu Leu Ser Gly Gly Gln Ala  Gln Arg Leu Cys Ile  Ala Arg Ala
        1190                1195                1200
```

-continued

```
Leu Leu Arg Lys Ser Lys Ile Leu Ile Leu Asp Glu Cys Thr Ser
    1205                1210                1215

Ala Leu Asp Ser Val Ser Ser Ile Ile Asn Glu Ile Val Lys
    1220                1225                1230

Lys Gly Pro Pro Ala Leu Leu Thr Met Val Ile Thr His Ser Glu
    1235                1240                1245

Gln Met Met Arg Ser Cys Asn Ser Ile Ala Val Leu Lys Asp Gly
    1250                1255                1260

Lys Val Val Glu Arg Gly Asn Phe Asp Thr Leu Tyr Asn Asn Arg
    1265                1270                1275

Gly Glu Leu Phe Gln Ile Val Ser Asn Gln Ser Ser
    1280                1285                1290

<210> SEQ ID NO 27
<211> LENGTH: 1362
<212> TYPE: PRT
<213> ORGANISM: Schizosaccharomyces pombe

<400> SEQUENCE: 27

Met Ser Leu His Ser Lys Lys Ser Thr Ser Thr Val Lys Asp Asn Glu
1               5                   10                  15

His Ser Leu Asp Leu Ser Ile Lys Ser Ile Pro Ser Asn Glu Lys Asn
            20                  25                  30

Phe Ser Thr Glu Lys Ser Glu Asn Glu Ala Ser Glu Ser His Val Val
        35                  40                  45

Asp Val Val Lys Asp Pro Phe Glu Gln Tyr Thr Pro Glu Glu Gln Glu
    50                  55                  60

Ile Leu Tyr Lys Gln Ile Asn Asp Thr Pro Ala Lys Leu Ser Gly Tyr
65                  70                  75                  80

Pro Arg Ile Leu Ser Tyr Ala Asp Lys Trp Asp Ile Met Leu Gln Leu
                85                  90                  95

Ala Gly Thr Ile Thr Gly Ile Gly Ala Gly Leu Gly Met Pro Leu Met
            100                 105                 110

Ser Leu Val Ser Gly Gln Leu Ala Gln Ala Phe Thr Asp Leu Ala Ser
        115                 120                 125

Gly Lys Gly Ala Ser Ser Phe Gln His Thr Val Asp His Phe Cys Leu
    130                 135                 140

Tyr Phe Ile Tyr Ile Ala Ile Gly Val Phe Gly Cys Ser Tyr Ile Tyr
145                 150                 155                 160

Thr Val Thr Phe Ile Ile Ala Gly Glu Arg Ile Ala Arg Arg Ile Arg
                165                 170                 175

Gln Asp Tyr Leu His Ala Ile Leu Ser Gln Asn Ile Gly Tyr Phe Asp
            180                 185                 190

Arg Leu Gly Ala Gly Glu Ile Thr Thr Arg Ile Thr Thr Asp Thr Asn
        195                 200                 205

Phe Ile Gln Asp Gly Leu Gly Glu Lys Val Gly Leu Val Phe Phe Ala
    210                 215                 220

Ile Ala Thr Phe Val Ser Gly Phe Val Ile Ala Phe Ile Arg His Trp
225                 230                 235                 240

Lys Phe Thr Leu Ile Leu Ser Ser Met Phe Pro Ala Ile Cys Gly Gly
                245                 250                 255

Ile Gly Leu Gly Val Pro Phe Ile Thr Lys Asn Thr Lys Gly Gln Ile
            260                 265                 270

Ala Val Val Ala Glu Ser Ser Thr Phe Val Glu Glu Val Phe Ser Asn
        275                 280                 285
```

```
Ile Arg Asn Ala Phe Ala Phe Gly Thr Gln Asp Ile Leu Ala Lys Leu
290                 295                 300

Tyr Asn Lys Tyr Leu Ile Thr Ala Gln Arg Phe Gly Ile Asn Lys Ala
305                 310                 315                 320

Ile Ala Met Gly Leu Met Val Gly Trp Met Phe Phe Val Ala Tyr Gly
                325                 330                 335

Val Tyr Gly Leu Ala Phe Trp Glu Gly Arg Leu Leu His Ala Gly
                340                 345                 350

Asp Leu Asp Val Ser Lys Leu Ile Gly Cys Phe Phe Ala Val Leu Ile
                355                 360                 365

Ala Ser Tyr Ser Leu Ala Asn Ile Ser Pro Lys Met Gln Ser Phe Val
370                 375                 380

Ser Cys Ala Ser Ala Ala Lys Lys Ile Phe Asp Thr Ile Asp Arg Val
385                 390                 395                 400

Ser Pro Ile Asn Ala Phe Thr Pro Thr Gly Asp Val Val Lys Asp Ile
                405                 410                 415

Lys Gly Glu Ile Glu Leu Lys Asn Ile Arg Phe Val Tyr Pro Thr Arg
                420                 425                 430

Pro Glu Val Leu Val Leu Asp Asn Phe Ser Leu Val Cys Pro Ser Gly
                435                 440                 445

Lys Ile Thr Ala Leu Val Gly Ala Ser Gly Ser Gly Lys Ser Thr Ile
450                 455                 460

Ile Gly Leu Val Glu Arg Phe Tyr Asp Pro Ile Gly Gly Gln Val Phe
465                 470                 475                 480

Leu Asp Gly Lys Asp Leu Arg Thr Leu Asn Val Ala Ser Leu Arg Asn
                485                 490                 495

Gln Ile Ser Leu Val Gln Gln Glu Pro Val Leu Phe Ala Thr Thr Val
                500                 505                 510

Phe Glu Asn Ile Thr Tyr Gly Leu Pro Asp Thr Ile Lys Gly Thr Leu
                515                 520                 525

Ser Lys Glu Glu Leu Glu Arg Arg Val Tyr Asp Ala Ala Lys Leu Ala
                530                 535                 540

Asn Ala Tyr Asp Phe Ile Met Thr Leu Pro Glu Gln Phe Ser Thr Asn
545                 550                 555                 560

Val Gly Gln Arg Gly Phe Leu Met Ser Gly Gly Gln Lys Gln Arg Ile
                565                 570                 575

Ala Ile Ala Arg Ala Val Ile Ser Asp Pro Lys Ile Leu Leu Leu Asp
                580                 585                 590

Glu Ala Thr Ser Ala Leu Asp Ser Lys Ser Glu Val Leu Val Gln Lys
                595                 600                 605

Ala Leu Asp Asn Ala Ser Arg Ser Arg Thr Thr Ile Val Ile Ala His
610                 615                 620

Arg Leu Ser Thr Ile Arg Asn Ala Asp Asn Ile Val Val Val Asn Ala
625                 630                 635                 640

Gly Lys Ile Val Glu Gln Gly Ser His Asn Glu Leu Leu Asp Leu Asn
                645                 650                 655

Gly Ala Tyr Ala Arg Leu Val Glu Ala Gln Lys Leu Ser Gly Gly Glu
                660                 665                 670

Lys Asp Gln Glu Met Val Glu Glu Leu Glu Asp Ala Pro Arg Glu
                675                 680                 685

Ile Pro Ile Thr Ser Phe Gly Asp Asp Glu Asp Asn Asp Met Ala
                690                 695                 700

Ser Leu Glu Ala Pro Met Met Ser His Asn Thr Asp Thr Asp Thr Leu
705                 710                 715                 720
```

-continued

Asn Asn Lys Leu Asn Glu Lys Asp Asn Val Val Phe Glu Asp Lys Thr
              725                 730                 735

Leu Gln His Val Ala Ser Glu Ile Val Pro Asn Leu Pro Pro Ala Asp
              740                 745                 750

Val Gly Glu Leu Asn Glu Pro Lys Lys Ser Lys Lys Ser Lys Lys
              755                 760                 765

Asn Asn His Glu Ile Asn Ser Leu Thr Ala Leu Trp Phe Ile His Ser
770                 775                 780

Phe Val Arg Thr Met Ile Glu Ile Ile Cys Leu Leu Ile Gly Ile Leu
785                 790                 795                 800

Ala Ser Met Ile Cys Gly Ala Ala Tyr Pro Val Gln Ala Ala Val Phe
              805                 810                 815

Ala Arg Phe Leu Asn Ile Phe Thr Asp Leu Ser Ser Thr Asp Phe Leu
              820                 825                 830

His Lys Val Asn Val Phe Ala Val Tyr Trp Leu Ile Leu Ala Ile Val
              835                 840                 845

Gln Phe Phe Ala Tyr Ala Ile Ser Asn Phe Ala Met Thr Tyr Ala Met
850                 855                 860

Glu Ala Val Leu Gln Arg Ile Arg Tyr His Leu Phe Arg Thr Leu Leu
865                 870                 875                 880

Arg Gln Asp Val Glu Phe Phe Asp Arg Ser Glu Asn Thr Val Gly Ala
              885                 890                 895

Ile Thr Thr Ser Leu Ser Thr Lys Ile Gln Ser Leu Glu Gly Leu Ser
              900                 905                 910

Gly Pro Thr Leu Gly Thr Phe Phe Gln Ile Leu Thr Asn Ile Ile Ser
              915                 920                 925

Val Thr Ile Leu Ser Leu Ala Thr Gly Trp Lys Leu Gly Leu Val Thr
930                 935                 940

Leu Ser Thr Ser Pro Val Ile Ile Thr Ala Gly Tyr Tyr Arg Val Arg
945                 950                 955                 960

Ala Leu Asp Gln Val Gln Glu Lys Leu Ser Ala Ala Tyr Lys Glu Ser
              965                 970                 975

Ala Ala Phe Ala Cys Glu Ser Thr Ser Ala Ile Arg Thr Val Ala Ser
              980                 985                 990

Leu Asn Arg Glu Glu Asn Val Phe Ala Glu Tyr Cys Asp Ser Leu Ile
              995                 1000                 1005

Lys Pro Gly Arg Glu Ser Ala Ile Ala Ser Leu Lys Ser Gly Leu
     1010                 1015                 1020

Phe Phe Ser Ala Ala Gln Gly Val Thr Phe Leu Ile Asn Ala Leu
     1025                 1030                 1035

Thr Phe Trp Tyr Gly Ser Thr Leu Met Arg Lys Gly Glu Tyr Asn
     1040                 1045                 1050

Ile Val Gln Phe Tyr Thr Cys Phe Ile Ala Ile Val Phe Gly Ile
     1055                 1060                 1065

Gln Gln Ala Gly Gln Phe Gly Tyr Ser Ala Asp Val Thr Lys
     1070                 1075                 1080

Ala Lys Ala Ala Ala Gly Glu Ile Lys Tyr Leu Ser Glu Ser Lys
     1085                 1090                 1095

Pro Lys Ile Asp Thr Trp Ser Thr Glu Gly Lys Lys Val Glu Ser
     1100                 1105                 1110

Leu Gln Ser Ala Ala Ile Glu Phe Arg Gln Val Glu Phe Ser Tyr
     1115                 1120                 1125

Pro Thr Arg Arg His Ile Lys Val Leu Arg Gly Leu Asn Leu Thr

```
                    1130                1135                1140

Val Lys Pro Gly Gln Phe Val Ala Phe Val Gly Ser Ser Gly Cys
    1145                1150                1155

Gly Lys Ser Thr Thr Ile Gly Leu Ile Glu Arg Phe Tyr Asp Cys
    1160                1165                1170

Asp Asn Gly Ala Val Leu Val Asp Gly Val Asn Val Arg Asp Tyr
    1175                1180                1185

Asn Ile Asn Asp Tyr Arg Lys Gln Ile Ala Leu Val Ser Gln Glu
    1190                1195                1200

Pro Thr Leu Tyr Gln Gly Thr Val Arg Glu Asn Ile Val Leu Gly
    1205                1210                1215

Ala Ser Lys Asp Val Ser Glu Glu Met Ile Glu Ala Cys Lys
    1220                1225                1230

Lys Ala Asn Ile His Glu Phe Ile Leu Gly Leu Pro Asn Gly Tyr
    1235                1240                1245

Asn Thr Leu Cys Gly Gln Lys Gly Ser Ser Leu Ser Gly Gly Gln
    1250                1255                1260

Lys Gln Arg Ile Ala Ile Ala Arg Ala Leu Ile Arg Asn Pro Lys
    1265                1270                1275

Ile Leu Leu Leu Asp Glu Ala Thr Ser Ala Leu Asp Ser His Ser
    1280                1285                1290

Glu Lys Val Val Gln Glu Ala Leu Asn Ala Ala Ser Gln Gly Arg
    1295                1300                1305

Thr Thr Val Ala Ile Ala His Arg Leu Ser Ser Ile Gln Asp Ala
    1310                1315                1320

Asp Cys Ile Phe Val Phe Asp Gly Gly Val Thr Cys Glu Ala Gly
    1325                1330                1335

Thr His Ala Glu Leu Val Lys Gln Arg Gly Arg Tyr Tyr Glu Leu
    1340                1345                1350

Val Val Glu Gln Gly Leu Asn Lys Ala
    1355                1360

<210> SEQ ID NO 28
<211> LENGTH: 1511
<212> TYPE: PRT
<213> ORGANISM: Saccharomyces cerevisiae

<400> SEQUENCE: 28

Met Pro Glu Ala Lys Leu Asn Asn Val Asn Asp Val Thr Ser Tyr
1               5                   10                  15

Ser Ser Ala Ser Ser Thr Glu Asn Ala Ala Asp Leu His Asn Tyr
                20                  25                  30

Asn Gly Phe Asp Glu His Thr Ala Arg Ile Gln Lys Leu Ala Arg
            35                  40                  45

Thr Leu Thr Ala Gln Ser Met Gln Asn Ser Thr Gln Ser Ala Pro Asn
    50                  55                  60

Lys Ser Asp Ala Gln Ser Ile Phe Ser Ser Val Glu Gly Val Asn
65                  70                  75                  80

Pro Ile Phe Ser Asp Pro Glu Ala Pro Gly Tyr Asp Pro Lys Leu Asp
                85                  90                  95

Pro Asn Ser Glu Asn Phe Ser Ala Ala Trp Val Asn Met Ala
            100                 105                 110

His Leu Ser Ala Ala Asp Pro Asp Phe Tyr Lys Pro Tyr Ser Leu Gly
    115                 120                 125

Cys Ala Trp Lys Asn Leu Ser Ala Ser Gly Ala Ser Ala Asp Val Ala
```

-continued

```
            130                 135                 140
Tyr Gln Ser Thr Val Val Asn Ile Pro Tyr Lys Ile Leu Lys Ser Gly
145                 150                 155                 160

Leu Arg Lys Phe Gln Arg Ser Lys Glu Thr Asn Thr Phe Gln Ile Leu
                165                 170                 175

Lys Pro Met Asp Gly Cys Leu Asn Pro Gly Glu Leu Leu Val Val Leu
            180                 185                 190

Gly Arg Pro Gly Ser Gly Cys Thr Thr Leu Leu Lys Ser Ile Ser Ser
                195                 200                 205

Asn Thr His Gly Phe Asp Leu Gly Ala Asp Thr Lys Ile Ser Tyr Ser
            210                 215                 220

Gly Tyr Ser Gly Asp Asp Ile Lys Lys His Phe Arg Gly Glu Val Val
225                 230                 235                 240

Tyr Asn Ala Glu Ala Asp Val His Leu Pro His Leu Thr Val Phe Glu
                245                 250                 255

Thr Leu Val Thr Val Ala Arg Leu Lys Thr Pro Gln Asn Arg Ile Lys
            260                 265                 270

Gly Val Asp Arg Glu Ser Tyr Ala Asn His Leu Ala Glu Val Ala Met
                275                 280                 285

Ala Thr Tyr Gly Leu Ser His Thr Arg Asn Thr Lys Val Gly Asn Asp
            290                 295                 300

Ile Val Arg Gly Val Ser Gly Gly Glu Arg Lys Arg Val Ser Ile Ala
305                 310                 315                 320

Glu Val Ser Ile Cys Gly Ser Lys Phe Gln Cys Trp Asp Asn Ala Thr
                325                 330                 335

Arg Gly Leu Asp Ser Ala Thr Ala Leu Glu Phe Ile Arg Ala Leu Lys
            340                 345                 350

Thr Gln Ala Asp Ile Ser Asn Thr Ser Ala Thr Val Ala Ile Tyr Gln
                355                 360                 365

Cys Ser Gln Asp Ala Tyr Asp Leu Phe Asn Lys Val Cys Val Leu Asp
            370                 375                 380

Asp Gly Tyr Gln Ile Tyr Tyr Gly Pro Ala Asp Lys Ala Lys Lys Tyr
385                 390                 395                 400

Phe Glu Asp Met Gly Tyr Val Cys Pro Ser Arg Gln Thr Thr Ala Asp
                405                 410                 415

Phe Leu Thr Ser Val Thr Ser Pro Ser Glu Arg Thr Leu Asn Lys Asp
            420                 425                 430

Met Leu Lys Lys Gly Ile His Ile Pro Gln Thr Pro Lys Glu Met Asn
            435                 440                 445

Asp Tyr Trp Val Lys Ser Pro Asn Tyr Lys Glu Leu Met Lys Glu Val
        450                 455                 460

Asp Gln Arg Leu Leu Asn Asp Asp Glu Ala Ser Arg Glu Ala Ile Lys
465                 470                 475                 480

Glu Ala His Ile Ala Lys Gln Ser Lys Arg Ala Arg Pro Ser Ser Pro
                485                 490                 495

Tyr Thr Val Ser Tyr Met Met Gln Val Lys Tyr Leu Leu Ile Arg Asn
            500                 505                 510

Met Trp Arg Leu Arg Asn Asn Ile Gly Phe Thr Leu Phe Met Ile Leu
            515                 520                 525

Gly Asn Cys Ser Met Ala Leu Ile Leu Gly Ser Met Phe Phe Lys Ile
            530                 535                 540

Met Lys Lys Gly Asp Thr Ser Thr Phe Tyr Phe Arg Gly Ser Ala Met
545                 550                 555                 560
```

-continued

```
Phe Phe Ala Ile Leu Phe Asn Ala Phe Ser Ser Leu Leu Glu Ile Phe
            565                 570                 575

Ser Leu Tyr Glu Ala Arg Pro Ile Thr Glu Lys His Arg Thr Tyr Ser
        580                 585                 590

Leu Tyr His Pro Ser Ala Asp Ala Phe Ala Ser Val Leu Ser Glu Ile
    595                 600                 605

Pro Ser Lys Leu Ile Ile Ala Val Cys Phe Asn Ile Ile Phe Tyr Phe
610                 615                 620

Leu Val Asp Phe Arg Arg Asn Gly Gly Val Phe Phe Phe Tyr Leu Leu
625                 630                 635                 640

Ile Asn Ile Val Ala Val Phe Ser Met Ser His Leu Phe Arg Cys Val
            645                 650                 655

Gly Ser Leu Thr Lys Thr Leu Ser Glu Ala Met Val Pro Ala Ser Met
                660                 665                 670

Leu Leu Leu Ala Leu Ser Met Tyr Thr Gly Phe Ala Ile Pro Lys Lys
            675                 680                 685

Lys Ile Leu Arg Trp Ser Lys Trp Ile Trp Tyr Ile Asn Pro Leu Ala
        690                 695                 700

Tyr Leu Phe Glu Ser Leu Leu Ile Asn Glu Phe His Gly Ile Lys Phe
705                 710                 715                 720

Pro Cys Ala Glu Tyr Val Pro Arg Gly Pro Ala Tyr Ala Asn Ile Ser
                725                 730                 735

Ser Thr Glu Ser Val Cys Thr Val Val Gly Ala Val Pro Gly Gln Asp
            740                 745                 750

Tyr Val Leu Gly Asp Asp Phe Ile Arg Gly Thr Tyr Gln Tyr Tyr His
        755                 760                 765

Lys Asp Lys Trp Arg Gly Phe Gly Ile Gly Met Ala Tyr Val Val Phe
    770                 775                 780

Phe Phe Phe Val Tyr Leu Phe Leu Cys Glu Tyr Asn Glu Gly Ala Lys
785                 790                 795                 800

Gln Lys Gly Glu Ile Leu Val Phe Pro Arg Ser Ile Val Lys Arg Met
            805                 810                 815

Lys Lys Arg Gly Val Leu Thr Glu Lys Asn Ala Asn Asp Pro Glu Asn
                820                 825                 830

Val Gly Glu Arg Ser Asp Leu Ser Ser Asp Arg Lys Met Leu Gln Glu
            835                 840                 845

Ser Ser Glu Glu Glu Ser Asp Thr Tyr Gly Glu Ile Gly Leu Ser Lys
850                 855                 860

Ser Glu Ala Ile Phe His Trp Arg Asn Leu Cys Tyr Glu Val Gln Ile
865                 870                 875                 880

Lys Ala Glu Thr Arg Arg Ile Leu Asn Asn Val Asp Gly Trp Val Lys
            885                 890                 895

Pro Gly Thr Leu Thr Ala Leu Met Gly Ala Ser Gly Ala Gly Lys Thr
                900                 905                 910

Thr Leu Leu Asp Cys Leu Ala Glu Arg Val Thr Met Gly Val Ile Thr
            915                 920                 925

Gly Asp Ile Leu Val Asn Gly Ile Pro Arg Asp Lys Ser Phe Pro Arg
        930                 935                 940

Ser Ile Gly Tyr Cys Gln Gln Asp Leu His Leu Lys Thr Ala Thr
945                 950                 955                 960

Val Arg Glu Ser Leu Arg Phe Ser Ala Tyr Leu Arg Gln Pro Ala Glu
            965                 970                 975

Val Ser Ile Glu Glu Lys Asn Arg Tyr Val Glu Val Ile Lys Ile
                980                 985                 990
```

-continued

```
Leu Glu Met Glu Lys Tyr Ala Asp Ala Val Val Gly Val Ala Gly Glu
        995                 1000                1005

Gly Leu Asn Val Glu Gln Arg Lys Arg Leu Thr Ile Gly Val Glu
    1010                1015                1020

Leu Thr Ala Lys Pro Lys Leu Leu Val Phe Leu Asp Glu Pro Thr
    1025                1030                1035

Ser Gly Leu Asp Ser Gln Thr Ala Trp Ser Ile Cys Gln Leu Met
    1040                1045                1050

Lys Lys Leu Ala Asn His Gly Gln Ala Ile Leu Cys Thr Ile His
    1055                1060                1065

Gln Pro Ser Ala Ile Leu Met Gln Glu Phe Asp Arg Leu Leu Phe
    1070                1075                1080

Met Gln Arg Gly Gly Lys Thr Val Tyr Phe Gly Asp Leu Gly Glu
    1085                1090                1095

Gly Cys Lys Thr Met Ile Asp Tyr Phe Glu Ser His Gly Ala His
    1100                1105                1110

Lys Cys Pro Ala Asp Ala Asn Pro Ala Glu Trp Met Leu Glu Val
    1115                1120                1125

Val Gly Ala Ala Pro Gly Ser His Ala Asn Gln Asp Tyr Tyr Glu
    1130                1135                1140

Val Trp Arg Asn Ser Glu Glu Tyr Arg Ala Val Gln Ser Glu Leu
    1145                1150                1155

Asp Trp Met Glu Arg Glu Leu Pro Lys Lys Gly Ser Ile Thr Ala
    1160                1165                1170

Ala Glu Asp Lys His Glu Phe Ser Gln Ser Ile Ile Tyr Gln Thr
    1175                1180                1185

Lys Leu Val Ser Ile Arg Leu Phe Gln Gln Tyr Trp Arg Ser Pro
    1190                1195                1200

Asp Tyr Leu Trp Ser Lys Phe Ile Leu Thr Ile Phe Asn Gln Leu
    1205                1210                1215

Phe Ile Gly Phe Thr Phe Phe Lys Ala Gly Thr Ser Leu Gln Gly
    1220                1225                1230

Leu Gln Asn Gln Met Leu Ala Val Phe Met Phe Thr Val Ile Phe
    1235                1240                1245

Asn Pro Ile Leu Gln Gln Tyr Leu Pro Ser Phe Val Gln Gln Arg
    1250                1255                1260

Asp Leu Tyr Glu Ala Arg Glu Arg Pro Ser Arg Thr Phe Ser Trp
    1265                1270                1275

Ile Ser Phe Ile Phe Ala Gln Ile Phe Val Glu Val Pro Trp Asn
    1280                1285                1290

Ile Leu Ala Gly Thr Ile Ala Tyr Phe Ile Tyr Tyr Tyr Pro Ile
    1295                1300                1305

Gly Phe Tyr Ser Asn Ala Ser Ala Ala Gly Gln Leu His Glu Arg
    1310                1315                1320

Gly Ala Leu Phe Trp Leu Phe Ser Cys Ala Phe Tyr Val Tyr Val
    1325                1330                1335

Gly Ser Met Gly Leu Leu Val Ile Ser Phe Asn Gln Val Ala Glu
    1340                1345                1350

Ser Ala Ala Asn Leu Ala Ser Leu Leu Phe Thr Met Ser Leu Ser
    1355                1360                1365

Phe Cys Gly Val Met Thr Thr Pro Ser Ala Met Pro Arg Phe Trp
    1370                1375                1380

Ile Phe Met Tyr Arg Val Ser Pro Leu Thr Tyr Phe Ile Gln Ala
```

```
            1385                1390                1395

Leu Leu Ala Val Gly Val Ala Asn Val Asp Val Lys Cys Ala Asp
    1400                1405                1410

Tyr Glu Leu Leu Glu Phe Thr Pro Pro Ser Gly Met Thr Cys Gly
    1415                1420                1425

Gln Tyr Met Glu Pro Tyr Leu Gln Leu Ala Lys Thr Gly Tyr Leu
    1430                1435                1440

Thr Asp Glu Asn Ala Thr Asp Thr Cys Ser Phe Cys Gln Ile Ser
    1445                1450                1455

Thr Thr Asn Asp Tyr Leu Ala Asn Val Asn Ser Phe Tyr Ser Glu
    1460                1465                1470

Arg Trp Arg Asn Tyr Gly Ile Phe Ile Cys Tyr Ile Ala Phe Asn
    1475                1480                1485

Tyr Ile Ala Gly Val Phe Phe Tyr Trp Leu Ala Arg Val Pro Lys
    1490                1495                1500

Lys Asn Gly Lys Leu Ser Lys Lys
    1505                1510

<210> SEQ ID NO 29
<211> LENGTH: 1501
<212> TYPE: PRT
<213> ORGANISM: Candida albicans

<400> SEQUENCE: 29

Met Ser Asp Ser Lys Met Ser Ser Gln Asp Glu Ser Lys Leu Glu Lys
1               5                   10                  15

Ala Ile Ser Gln Asp Ser Ser Glu Asn His Ser Ile Asn Glu Tyr
            20                  25                  30

His Gly Phe Asp Ala His Thr Ser Glu Asn Ile Gln Asn Leu Ala Arg
        35                  40                  45

Thr Phe Thr His Asp Ser Phe Lys Asp Ser Ser Ala Gly Leu Leu
    50                  55                  60

Lys Tyr Leu Thr His Met Ser Glu Val Pro Gly Val Asn Pro Tyr Glu
65              70                  75                  80

His Glu Glu Ile Asn Asn Asp Gln Leu Asn Pro Asp Ser Glu Asn Phe
                85                  90                  95

Asn Ala Lys Phe Trp Val Lys Asn Leu Arg Lys Leu Phe Glu Ser Asp
            100                 105                 110

Pro Glu Tyr Tyr Lys Pro Ser Lys Leu Gly Ile Gly Tyr Arg Asn Leu
        115                 120                 125

Arg Ala Tyr Gly Val Ala Asn Asp Ser Asp Tyr Gln Pro Thr Val Thr
    130                 135                 140

Asn Ala Leu Trp Lys Leu Ala Thr Glu Gly Phe Arg His Phe Gln Lys
145                 150                 155                 160

Asp Asp Asp Ser Arg Tyr Phe Asp Ile Leu Lys Ser Met Asp Ala Ile
                165                 170                 175

Met Arg Pro Gly Glu Leu Thr Val Val Leu Gly Arg Pro Gly Ala Gly
            180                 185                 190

Cys Ser Thr Leu Leu Lys Thr Ile Ala Val Asn Thr Tyr Gly Phe His
        195                 200                 205

Ile Gly Lys Glu Ser Gln Ile Tyr Asp Gly Leu Ser Pro His Asp
    210                 215                 220

Ile Glu Arg His Tyr Arg Gly Asp Val Ile Tyr Ser Ala Glu Thr Asp
225                 230                 235                 240

Val His Phe Pro His Leu Ser Val Gly Asp Thr Leu Glu Phe Ala Ala
```

-continued

```
            245                 250                 255
Arg Leu Arg Thr Pro Gln Asn Arg Gly Glu Gly Ile Asp Arg Glu Thr
            260                 265                 270

Tyr Ala Lys His Met Ala Ser Val Tyr Met Ala Thr Tyr Gly Leu Ser
            275                 280             285

His Thr Arg Asn Thr Asn Val Gly Asn Asp Phe Val Arg Gly Val Ser
        290                 295                 300

Gly Gly Glu Arg Lys Arg Val Ser Ile Ala Glu Ala Ser Leu Ser Gly
305                 310                 315                 320

Ala Asn Ile Gln Cys Trp Asp Asn Ala Thr Arg Gly Leu Asp Ser Ala
                325                 330                 335

Thr Ala Leu Glu Phe Ile Arg Ala Leu Lys Thr Ser Ala Val Ile Leu
            340                 345                 350

Asp Thr Thr Pro Leu Ile Ala Ile Tyr Gln Cys Ser Gln Asp Ala Tyr
            355                 360                 365

Asp Leu Phe Asp Lys Val Val Leu Tyr Glu Gly Tyr Gln Ile Phe
            370                 375             380

Phe Gly Lys Ala Thr Lys Ala Lys Glu Tyr Phe Glu Lys Met Gly Trp
385                 390                 395                 400

Lys Cys Pro Gln Arg Gln Thr Thr Ala Asp Phe Leu Thr Ser Leu Thr
                405                 410                 415

Asn Pro Ala Glu Arg Glu Pro Leu Pro Gly Tyr Glu Asp Lys Val Pro
            420                 425                 430

Arg Thr Ala Gln Glu Phe Glu Thr Tyr Trp Lys Asn Ser Pro Glu Tyr
            435                 440                 445

Ala Glu Leu Thr Lys Glu Ile Asp Glu Tyr Phe Val Glu Cys Glu Arg
            450                 455                 460

Ser Asn Thr Arg Glu Thr Tyr Arg Glu Ser His Val Ala Lys Gln Ser
465                 470                 475                 480

Asn Asn Thr Arg Pro Ala Ser Pro Tyr Thr Val Ser Phe Phe Met Gln
                485                 490                 495

Val Arg Tyr Gly Val Ala Arg Asn Phe Leu Arg Met Lys Gly Asp Pro
            500                 505                 510

Ser Ile Pro Ile Phe Ser Val Phe Gly Gln Leu Val Met Gly Leu Ile
            515                 520                 525

Leu Ser Ser Val Phe Tyr Asn Leu Ser Gln Thr Thr Gly Ser Phe Tyr
            530                 535                 540

Tyr Arg Gly Ala Ala Met Phe Phe Ala Val Leu Phe Asn Ala Phe Ser
545                 550                 555                 560

Ser Leu Leu Glu Ile Met Ser Leu Phe Glu Ala Arg Pro Ile Val Glu
                565                 570                 575

Lys His Lys Lys Tyr Ala Leu Tyr Arg Pro Ser Ala Asp Ala Leu Ala
            580                 585                 590

Ser Ile Ile Ser Glu Leu Pro Val Lys Leu Ala Met Ser Met Ser Phe
            595                 600                 605

Asn Phe Val Phe Tyr Phe Met Val Asn Phe Arg Arg Asn Pro Gly Arg
            610                 615                 620

Phe Phe Phe Tyr Trp Leu Met Cys Ile Trp Cys Thr Phe Val Met Ser
625                 630                 635                 640

His Leu Phe Arg Ser Ile Gly Ala Val Ser Thr Ser Ile Ser Gly Ala
                645                 650                 655

Met Thr Pro Ala Thr Val Leu Leu Leu Ala Met Val Ile Tyr Thr Gly
            660                 665                 670
```

-continued

Phe Val Ile Pro Thr Pro Ser Met Leu Gly Trp Ser Arg Trp Ile Asn
        675                 680                 685

Tyr Ile Asn Pro Val Gly Tyr Val Phe Glu Ser Leu Met Val Asn Glu
    690                 695                 700

Phe His Gly Arg Glu Phe Gln Cys Ala Gln Tyr Val Pro Ser Gly Pro
705                 710                 715                 720

Gly Tyr Glu Asn Ile Ser Arg Ser Asn Gln Val Cys Thr Ala Val Gly
                725                 730                 735

Ser Val Pro Gly Asn Glu Met Val Ser Gly Thr Asn Tyr Leu Ala Gly
            740                 745                 750

Ala Tyr Gln Tyr Tyr Asn Ser His Lys Trp Arg Asn Leu Gly Ile Thr
        755                 760                 765

Ile Gly Phe Ala Val Phe Phe Leu Ala Ile Tyr Ile Ala Leu Thr Glu
    770                 775                 780

Phe Asn Lys Gly Ala Met Gln Lys Gly Glu Ile Val Leu Phe Leu Lys
785                 790                 795                 800

Gly Ser Leu Lys Lys His Lys Arg Lys Thr Ala Ala Ser Asn Lys Gly
                805                 810                 815

Asp Ile Glu Ala Gly Pro Val Ala Gly Lys Leu Asp Tyr Gln Asp Glu
            820                 825                 830

Ala Glu Ala Val Asn Asn Glu Lys Phe Thr Glu Lys Gly Ser Thr Gly
        835                 840                 845

Ser Val Asp Phe Pro Glu Asn Arg Glu Ile Phe Phe Trp Arg Asp Leu
    850                 855                 860

Thr Tyr Gln Val Lys Ile Lys Lys Glu Asp Arg Val Ile Leu Asp His
865                 870                 875                 880

Val Asp Gly Trp Val Lys Pro Gly Gln Ile Thr Ala Leu Met Gly Ala
                885                 890                 895

Ser Gly Ala Gly Lys Thr Thr Leu Leu Asn Cys Leu Ser Glu Arg Val
            900                 905                 910

Thr Thr Gly Ile Ile Thr Asp Gly Glu Arg Leu Val Asn Gly His Ala
        915                 920                 925

Leu Asp Ser Ser Phe Gln Arg Ser Ile Gly Tyr Val Gln Gln Gln Asp
    930                 935                 940

Val His Leu Pro Thr Ser Thr Val Arg Glu Ala Leu Gln Phe Ser Ala
945                 950                 955                 960

Tyr Leu Arg Gln Ser Asn Lys Ile Ser Lys Lys Glu Lys Asp Asp Tyr
                965                 970                 975

Val Asp Tyr Val Ile Asp Leu Leu Glu Met Thr Asp Tyr Ala Asp Ala
            980                 985                 990

Leu Val Gly Val Ala Gly Glu Gly Leu Asn Val Glu Gln Arg Lys Arg
        995                 1000                1005

Leu Thr Ile Gly Val Glu Leu Val Ala Lys Pro Lys Leu Leu Leu
    1010                1015                1020

Phe Leu Asp Glu Pro Thr Ser Gly Leu Asp Ser Gln Thr Ala Trp
    1025                1030                1035

Ser Ile Cys Lys Leu Met Arg Lys Leu Ala Asp His Gly Gln Ala
    1040                1045                1050

Ile Leu Cys Thr Ile His Gln Pro Ser Ala Leu Ile Met Ala Glu
    1055                1060                1065

Phe Asp Arg Leu Leu Phe Leu Gln Lys Gly Gly Arg Thr Ala Tyr
    1070                1075                1080

Phe Gly Glu Leu Gly Glu Asn Cys Gln Thr Met Ile Asn Tyr Phe
    1085                1090                1095

```
        Glu Lys Tyr Gly Ala Asp Pro Cys Pro Lys Glu Ala Asn Pro Ala
            1100                1105                1110

Glu Trp Met Leu Gln Val Val Gly Ala Ala Pro Gly Ser His Ala
            1115                1120                1125

Lys Gln Asp Tyr Phe Glu Val Trp Arg Asn Ser Ser Glu Tyr Gln
            1130                1135                1140

Ala Val Arg Glu Glu Ile Asn Arg Met Glu Ala Glu Leu Ser Lys
            1145                1150                1155

Leu Pro Arg Asp Asn Asp Pro Glu Ala Leu Leu Lys Tyr Ala Ala
            1160                1165                1170

Pro Leu Trp Lys Gln Tyr Leu Leu Val Ser Trp Arg Thr Ile Val
            1175                1180                1185

Gln Asp Trp Arg Ser Pro Gly Tyr Ile Tyr Ser Lys Ile Phe Leu
            1190                1195                1200

Val Val Ser Ala Ala Leu Phe Asn Gly Phe Ser Phe Phe Lys Ala
            1205                1210                1215

Lys Asn Asn Met Gln Gly Leu Gln Asn Gln Met Phe Ser Val Phe
            1220                1225                1230

Met Phe Phe Ile Pro Phe Asn Thr Leu Val Gln Gln Met Leu Pro
            1235                1240                1245

Tyr Phe Val Lys Gln Arg Asp Val Tyr Glu Val Arg Glu Ala Pro
            1250                1255                1260

Ser Arg Thr Phe Ser Trp Phe Ala Phe Ile Ala Gly Gln Ile Thr
            1265                1270                1275

Ser Glu Ile Pro Tyr Gln Val Ala Val Gly Thr Ile Ala Phe Phe
            1280                1285                1290

Cys Trp Tyr Tyr Pro Leu Gly Leu Tyr Asn Asn Ala Thr Pro Thr
            1295                1300                1305

Asp Ser Val Asn Pro Arg Gly Val Leu Met Trp Met Leu Val Thr
            1310                1315                1320

Ala Phe Tyr Val Tyr Thr Ala Thr Met Gly Gln Leu Cys Met Ser
            1325                1330                1335

Phe Ser Glu Leu Ala Asp Asn Ala Ala Asn Leu Ala Thr Leu Leu
            1340                1345                1350

Phe Thr Met Cys Leu Asn Phe Cys Gly Val Leu Ala Gly Pro Asp
            1355                1360                1365

Val Leu Pro Gly Phe Trp Ile Phe Met Tyr Arg Cys Asn Pro Phe
            1370                1375                1380

Thr Tyr Leu Val Gln Ala Met Leu Ser Thr Gly Leu Ala Asn Thr
            1385                1390                1395

Phe Val Lys Cys Ala Glu Arg Glu Tyr Val Ser Val Lys Pro Pro
            1400                1405                1410

Asn Gly Glu Ser Cys Ser Thr Tyr Leu Asp Pro Tyr Ile Lys Phe
            1415                1420                1425

Ala Gly Gly Tyr Phe Glu Thr Arg Asn Asp Gly Ser Cys Ala Phe
            1430                1435                1440

Cys Gln Met Ser Ser Thr Asn Thr Phe Leu Lys Ser Val Asn Ser
            1445                1450                1455

Leu Tyr Ser Glu Arg Trp Arg Asn Phe Gly Ile Phe Ile Ala Phe
            1460                1465                1470

Ile Ala Ile Asn Ile Ile Leu Thr Val Ile Phe Tyr Trp Leu Ala
            1475                1480                1485

Arg Val Pro Lys Gly Asn Arg Glu Lys Lys Asn Lys Lys
```

<210> SEQ ID NO 30
<211> LENGTH: 1619
<212> TYPE: PRT
<213> ORGANISM: Magnaporthe grisea

<400> SEQUENCE: 30

Met Ser Gln Pro Val Glu Asp Pro Ser His Asp Gln Ala Arg Asn Asp
1               5                   10                  15

Asn Ala Gln Thr Thr Thr Asp Thr Gly Asn Ala Ser Met Pro Lys Thr
            20                  25                  30

Asn Gly His Asp Gln Glu Ser Ser Ala Thr Gly Ile Ser Ser Ser Pro
        35                  40                  45

Ala Asp Thr Leu Met Asp Lys Glu Lys Gln Ala Ala Pro Thr Pro Glu
50 55 60

Pro Ser Thr Glu Lys Ala Ala Val Pro Asp Pro Ala Ala Ser Val Ala
65 70 75 80

Ser Asp Thr Ala Glu Asp Glu Phe Phe Asp Asp Asn Asp Ser Glu Gln
85 90 95

Arg Arg Arg Asn Glu Met Val Gln Gln Leu Ala Arg Thr Tyr Thr Ser
100 105 110

Arg Ser Asn Ala Ser Ala Ala Ala Asp Glu Tyr Gly Asn Ala Asn Pro
115 120 125

Phe Leu Ile Ala Ser Glu Asp Pro Asp Ser Pro Leu Asn Pro Ser Gly
130 135 140

Asn Asn Phe Lys Ala Tyr Ala Trp Ala Lys Ala Ile Ala Gly Met Val
145 150 155 160

Ala Ala Glu Gly Gly Ser Phe Arg Thr Ile Gly Ile Cys Phe Gln Asn
165 170 175

Met Asn Val Phe Gly Phe Gly Ala Ala Thr Asp Phe Gln Lys Thr Val
180 185 190

Ser Asn Val Trp Leu Glu Ala Ala Asn Met Leu Arg Thr Ala Val Gly
195 200 205

Met Gly Lys Thr Thr Arg Ile Asp Ile Leu Arg Gly Phe Asn Gly Val
210 215 220

Val Arg Asn Gly Glu Met Leu Val Val Leu Gly Pro Pro Gly Ser Gly
225 230 235 240

Cys Ser Thr Phe Leu Lys Thr Ile Ala Gly Glu Thr Asn Gly Leu Asn
245 250 255

Val Asp Gln Ser Ala Tyr Phe Asn Tyr Gln Gly Leu Ser Ala Glu Glu
260 265 270

Met His Lys Arg His Arg Gly Glu Ala Ile Tyr Thr Ala Glu Val Asp
275 280 285

Val His Phe Pro Gln Leu Ser Val Gly Asp Thr Leu Thr Phe Ala Ala
290 295 300

Asn Ala Arg Ala Pro Arg Arg Ala Pro Pro Gly Val Ser Lys Thr Leu
305 310 315 320

Phe Ala Asn His Ile Arg Asp Val Val Met Ala Ile Phe Gly Ile Ser
325 330 335

His Thr Ile Asn Thr Arg Val Gly Asn Glu Tyr Ile Arg Gly Val Ser
340 345 350

Gly Gly Glu Arg Lys Arg Val Thr Ile Ala Glu Ala Ala Leu Ser Gly
355 360 365

Ala Pro Leu Gln Cys Trp Asp Asn Ser Thr Arg Gly Leu Asp Ser Ala

-continued

```
            370                 375                 380
Asn Ala Ile Glu Phe Cys Lys Thr Leu Arg Val Cys Thr Arg Leu Phe
385                 390                 395                 400
Gln Thr Thr Ala Cys Val Ser Ile Tyr Gln Ala Pro Gln Ser Ala Tyr
                    405                 410                 415
Asp Met Phe Asp Lys Ala Val Val Leu Tyr Glu Gly Tyr Gln Ile Tyr
                    420                 425                 430
Phe Gly Pro Ala Asp Glu Ala Lys Gln Tyr Phe Val Asn Leu Gly Phe
                    435                 440                 445
Glu Cys Pro Ala Arg Thr Thr Pro Asp Phe Leu Thr Ser Met Thr Ala
450                 455                 460
Pro His Glu Arg Ile Val Arg Pro Gly Phe Glu Gly Lys Ala Pro Arg
465                 470                 475                 480
Thr Pro Glu Glu Phe Ala Ile Ala Trp Glu Asn Ser Ala Glu Tyr Thr
                    485                 490                 495
Ala Leu Gln Ala Asp Ile Glu Glu Tyr Lys Ser Ser His Pro Ile Asn
                    500                 505                 510
Gly Pro Asp Ala Glu Ala Phe Arg Lys Ser Arg Ala Ala Gln Gln Gly
                    515                 520                 525
Arg Gly Gln Arg Pro Asn Ser Pro Tyr Thr Leu Ser Phe Tyr Gln Gln
530                 535                 540
Thr Lys Leu Cys Leu Trp Arg Gly Trp Lys Arg Leu Leu Gly Asp Pro
545                 550                 555                 560
Thr Leu Thr Val Gly Ala Leu Phe Ala Asn Thr Leu Met Ala Leu Val
                    565                 570                 575
Ile Ser Ser Ile Phe Phe Asn Leu Gln Met Thr Thr Ser Ser Phe Phe
                    580                 585                 590
Gln Arg Gly Ala Leu Leu Phe Phe Ala Cys Leu Leu Asn Gly Phe Ala
                    595                 600                 605
Ala Ala Leu Glu Ile Leu Ile Leu Phe Ala Gln Arg Pro Ile Val Glu
610                 615                 620
Lys His Asp Arg Tyr Ala Leu Tyr His Pro Ser Ala Glu Ala Val Ala
625                 630                 635                 640
Ser Met Leu Cys Asp Met Pro Tyr Lys Val Phe Asn Ala Ile Val Phe
                    645                 650                 655
Asn Leu Val Leu Tyr Phe Met Ala Asn Leu Arg Arg Glu Pro Gly Ala
                    660                 665                 670
Phe Phe Phe Tyr Leu Leu Ile Ser Phe Ala Thr Val Leu Ala Met Ser
                    675                 680                 685
Met Met Phe Arg Thr Ile Ala Ser Met Ser Arg Ser Leu Ser Gln Ala
                    690                 695                 700
Met Val Pro Ala Ala Ile Ile Leu Ile Leu Ile Ile Phe Thr Gly
705                 710                 715                 720
Phe Val Ile Pro Leu Asp Tyr Met Leu Pro Trp Cys Arg Trp Leu Asn
                    725                 730                 735
Tyr Ile Asp Ile Leu Ala Tyr Ser Phe Glu Ser Leu Leu Ile Asn Glu
                    740                 745                 750
Phe Ala Gly Gln Arg Tyr Thr Cys Thr Glu Phe Val Pro Arg Ala Glu
                    755                 760                 765
Phe Pro Gly Tyr Gly Asp Leu Ser Gly Thr Asn Arg Val Cys Gln Ala
                    770                 775                 780
Val Gly Ser Val Ala Gly Gln Pro Phe Val Lys Gly Glu Asp Tyr Leu
785                 790                 795                 800
```

-continued

Tyr Ser Ser Phe Arg Tyr Glu Ser Ala Asn Lys Trp Arg Asn Phe Gly
            805                 810                 815

Ile Leu Ile Ala Phe Met Ile Phe Phe Cys Ser Arg Thr Trp Leu Arg
            820                 825                 830

Pro Arg Met Cys Glu Arg Lys Lys Ser Lys Gly Glu Val Leu Val Phe
            835                 840                 845

Arg Arg Gly Gln Arg Pro Ala Ala Ile Lys Asp Ala Lys Thr Asp Pro
            850                 855                 860

Glu Ala Gly Pro Pro Lys Val Gly Gly Ala Val Val Ala Ala Asn Met
865                 870                 875                 880

Thr Gly Glu Asn Ala Gly Phe Ile Gln Arg Gln Thr Ser Thr Phe Gly
            885                 890                 895

Trp Arg Asp Val Cys Tyr Glu Val Gln Ile Lys Lys Glu Thr Arg Arg
            900                 905                 910

Ile Leu Asp His Val Asp Gly Trp Val Lys Pro Gly Thr Leu Thr Ala
            915                 920                 925

Leu Met Gly Val Ser Gly Ala Gly Lys Thr Thr Leu Leu Asp Cys Leu
            930                 935                 940

Ala Asp Arg Thr Ser Met Gly Val Ile Thr Gly Glu Met Leu Val Asp
945                 950                 955                 960

Gly His Gln Arg Asp Ala Ser Phe Gln Arg Lys Thr Gly Tyr Val Gln
            965                 970                 975

Gln Gln Asp Leu His Leu Gln Thr Thr Thr Val Arg Glu Ala Leu Asn
            980                 985                 990

Phe Ser Ala Leu Leu Arg Gln Pro Ala His Val Pro Arg Ala Glu Lys
            995                 1000                1005

Leu Ala Tyr Val Asp Glu Val Ile Arg Leu Leu Asp Met Gln Glu
            1010                1015                1020

Tyr Ala Asp Ala Val Val Gly Val Pro Gly Glu Gly Leu Asn Val
            1025                1030                1035

Glu Gln Arg Lys Arg Leu Thr Ile Gly Val Glu Leu Ala Ala Lys
            1040                1045                1050

Pro Pro Leu Leu Leu Phe Val Asp Glu Pro Thr Ser Gly Leu Asp
            1055                1060                1065

Ser Gln Thr Ser Trp Ala Ile Leu Asp Leu Leu Glu Lys Leu Thr
            1070                1075                1080

Lys Ser Gly Gln Ala Ile Leu Cys Thr Ile His Gln Pro Ser Ala
            1085                1090                1095

Met Leu Phe Gln Arg Phe Asp Arg Leu Leu Phe Leu Ala Lys Gly
            1100                1105                1110

Gly Lys Thr Val Tyr Phe Gly Asp Ile Gly Glu Asn Ser Lys Ile
            1115                1120                1125

Met Thr Asp Tyr Phe Glu Arg Asn Gly Gly Phe Pro Cys Pro His
            1130                1135                1140

Asp Ala Asn Pro Ala Glu Trp Met Leu Glu Val Ile Gly Ala Ser
            1145                1150                1155

Pro Gly Thr Thr Ser Asp Ile Asp Trp His Gln Ala Trp Arg Glu
            1160                1165                1170

Ser Pro Glu Cys Ala Asp Val His Ala Glu Leu Asp Arg Leu Lys
            1175                1180                1185

-continued

Glu Gln Val Pro Asn Thr Pro Pro Thr Glu Asp Lys Ala Ser
1190            1195            1200

Tyr Arg Glu Phe Ala Ala Pro Phe His Gln Gln Ile Tyr Ala Val
1205            1210            1215

Thr His Arg Val Phe Gln Gln Tyr Trp Arg Thr Pro Ser Tyr Ile
1220            1225            1230

Tyr Ala Lys Ala Ala Leu Cys Ala Val Thr Ala Leu Phe Ile Gly
1235            1240            1245

Phe Val Phe Tyr Asp Ala Pro Asn Thr Gln Gln Gly Leu Gln Asn
1250            1255            1260

Gln Met Phe Ala Ile Phe Asn Ile Leu Thr Val Phe Gly Gln Leu
1265            1270            1275

Val Gln Gln Thr Met Pro His Phe Val Ile Gln Arg Asp Leu Tyr
1280            1285            1290

Glu Val Arg Glu Arg Pro Ser Lys Val Tyr Ser Trp Lys Val Phe
1295            1300            1305

Met Leu Ser Gln Ile Ile Val Glu Ile Pro Trp Asn Ser Leu Met
1310            1315            1320

Ala Val Ile Met Phe Phe Cys Trp Tyr Tyr Pro Val Gly Leu Glu
1325            1330            1335

Arg Asn Ala Ile Leu Ala Asp Gln Val Thr Glu Arg Gly Ala Leu
1340            1345            1350

Ala Phe Leu Tyr Leu Trp Gly Phe Leu Ile Phe Thr Ser Thr Phe
1355            1360            1365

Thr Asp Leu Met Ile Ala Gly Phe Glu Thr Ala Glu Ala Gly Gly
1370            1375            1380

Asn Ile Ala Asn Leu Phe Phe Ser Leu Cys Leu Ile Phe Cys Gly
1385            1390            1395

Val Leu Ala Asn Pro Asp Thr Met Pro Arg Phe Trp Ile Phe Met
1400            1405            1410

Tyr Arg Val Ser Pro Phe Thr Tyr Ile Val Ser Gly Leu Leu Ser
1415            1420            1425

Val Ala Val Ala Asn Ser Glu Val Arg Cys Ala Ser Asn Glu Phe
1430            1435            1440

Leu His Phe Asp Pro Leu Asn Gly Thr Cys Ala Glu Phe Met Arg
1445            1450            1455

Asn Tyr Ile Asn Gly Thr Thr Ile Pro Gly Leu Gly Arg Ile Pro
1460            1465            1470

Gly Ala Gly Gly Tyr Leu Arg Pro Asp Thr Glu Ser Ser Arg Ser
1475            1480            1485

Asn Cys Ala Phe Cys Pro Ile Lys Asp Thr Asn Ile Phe Leu Gln
1490            1495            1500

Gly Ala His Ala Asn Tyr Asn Asp Arg Trp Arg Asn Phe Gly Leu
1505            1510            1515

Ile Phe Val Tyr Ile Ile Phe Asn Ile Ile Ala Ala Leu Phe Val
1520            1525            1530

Tyr Trp Ala Val Arg Val Pro Lys Lys Lys Leu Gly Gly Lys Asp
1535            1540            1545

Ala Ala Ala Gly Val Gly Ala Gly Ala Gly Ala Ala Arg Ala Ser
1550            1555            1560

Ala Ser Asn Glu Lys Gly Lys Met Gln Arg Glu Lys Gly Glu Val
1565            1570            1575

-continued

```
Glu Gly Leu Thr Thr Ala Val Leu Gly Thr Ser Val Ala Gly Ser
    1580                1585                1590

Asp Ala Pro Met Thr Thr Thr Thr Glu Gly Glu Gly Glu Arg Ala
    1595                1600                1605

Lys Arg Arg Thr Ser Gly Asp Glu Val Val Arg
    1610                1615
```